US008901279B2

(12) United States Patent
Clarke et al.

(10) Patent No.: US 8,901,279 B2
(45) Date of Patent: *Dec. 2, 2014

(54) HUMANIZED ANTIBODIES WITH ANTI-TUMOR ACTIVITY

(71) Applicant: Teva Pharmaceuticals Australia Pty Ltd, Macquarie Park (AU)

(72) Inventors: Adam W. Clarke, Macquarie Park (AU); Anthony G. Doyle, Macquarie Park (AU); Philip A. Jennings, Macquarie Park (AU); Norbert Kienzle, Macquarie Park (AU); Matthew Pollard, Macquarie Park (AU)

(73) Assignee: Teva Pharmaceuticals Australia Pty Ltd, Macquarie Park, NSW (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/898,666

(22) Filed: May 21, 2013

(65) Prior Publication Data
US 2013/0280246 A1 Oct. 24, 2013

Related U.S. Application Data

(63) Continuation of application No. 12/725,192, filed on Mar. 16, 2010, now Pat. No. 8,470,320.

(60) Provisional application No. 61/160,682, filed on Mar. 16, 2010, provisional application No. 61/258,517, filed on Nov. 5, 2009.

(30) Foreign Application Priority Data

Mar. 16, 2009 (AU) .................. 2009901129

(51) Int. Cl.
*A61K 39/00* (2006.01)
*C07K 16/30* (2006.01)
*C07K 16/18* (2006.01)
*G01N 33/574* (2006.01)
*C07K 16/46* (2006.01)

(52) U.S. Cl.
CPC ............ *C07K 16/18* (2013.01); *C07K 16/3076* (2013.01); *A61K 2039/505* (2013.01); *G01N 33/57438* (2013.01); *G01N 33/57423* (2013.01); *C07K 2317/565* (2013.01); *C07K 2317/24* (2013.01); *C07K 2317/732* (2013.01); *G01N 33/57449* (2013.01); *C07K 2317/73* (2013.01); *C07K 2317/41* (2013.01); *C07K 2317/72* (2013.01); *C07K 2317/567* (2013.01); *G01N 33/57419* (2013.01); *C07K 16/464* (2013.01); *C07K 2317/734* (2013.01)
USPC ..................................................... 530/387.1

(58) Field of Classification Search
None
See application file for complete search history.

(56) References Cited

U.S. PATENT DOCUMENTS

| 5,225,539 | A | 7/1993 | Winter |
| 5,530,101 | A | 6/1996 | Queen et al. |
| 6,180,370 | B1 | 1/2001 | Queen et al. |
| 6,277,375 | B1 | 8/2001 | Ward |
| 6,423,511 | B1 | 7/2002 | Nakamura et al. |
| 6,602,684 | B1 | 8/2003 | Umana et al. |
| 6,821,505 | B2 | 11/2004 | Ward |
| 6,872,392 | B2 | 3/2005 | Nakamura et al. |
| 7,083,784 | B2 | 8/2006 | Dall'Acqua et al. |
| 7,217,797 | B2 | 5/2007 | Hinton et al. |
| 7,326,681 | B2 | 2/2008 | Gerngross |
| 7,388,081 | B2 | 6/2008 | Seki et al. |
| 7,915,387 | B2 | 3/2011 | Durrant et al. |
| 2009/0068175 | A1 | 3/2009 | Lazar et al. |
| 2009/0092599 | A1 | 4/2009 | Lazar et al. |
| 2009/0142340 | A1 | 6/2009 | Lazar et al. |

FOREIGN PATENT DOCUMENTS

| WO | WO0042072 A2 | 7/2000 |
| WO | WO2005108430 A2 | 11/2005 |
| WO | WO2008006554 A2 | 1/2008 |

OTHER PUBLICATIONS

Mariuzza et al. (Annu. Rev. Biophys. Biophys. Chem., 16: 139-159, 1987).*
Rudikoff, et al. (Proc. Natl. Acad. Sci. USA, 79(6):1979-1983, 1982, in IDS from Sep. 9, 2013).*
McCarthy and Hill (J. Immunol. Methods, 251(1-2):137-149, 2001).*
Benhar, I. (2007). "Design of synthetic antibody libraries." Expert Opin Biol Ther 7(5): 763-79.
Brekke, O. H., B. Bremnes, et al. (1993). "Human IgG3 can adopt the disulfide bond pattern characteristic for IgG1 without resembling it in complement mediated cell lysis." Mol Immunol 30(16): 1419-25.
Christensen, P. A., A. Danielczyk, et al. (2009). "Modifying antibody specificity by chain shuffling of V / V between antibodies with related specificities." Scand J Immunol 69(1): 1-10.
Dall'Acqua, W. F., K. E. Cook, et al. (2006). "Modulation of the effector functions of a human IgG1 through engineering of its hinge region." J Immunol 177(2): 1129-38.
Dall'Acqua, W. F., P. A. Kiener, et al. (2006). "Properties of human IgGIs engineered for enhanced binding to the neonatal Fc receptor (FcRn)." J Biol Chem 281(33): 23514-24.
Dall'Acqua, W. F., R. M. Woods, et al. (2002). "Increasing the affinity of a human IgGI for the neonatal Fc receptor: biological consequences." J Immunol 169(9): 5171-80.

(Continued)

*Primary Examiner* — Misook Yu
*Assistant Examiner* — Nelson B Moseley, II
(74) *Attorney, Agent, or Firm* — Stradley Ronon Stevens & Young, LLP

(57) ABSTRACT

The present invention provides humanised antibodies and binding domains thereof with anti-tumor activity. In particular the humanised antibodies have specific binding to and direct killing of human colon tumor cells and display potent immune-mediated cytotoxic activity against human colon cancer cells in vitro using antibody-dependent cell-mediated cytotoxicity (ADCC) and complement dependent cytotoxicity (CDC) assays and in vivo using mouse tumor models.

27 Claims, 18 Drawing Sheets

(56) References Cited

OTHER PUBLICATIONS

Durrant, L. G., S. J. Harding, et al. (2006). "A new anticancer glycolipid monoclonal antibody, SC104, which directly induces tumor cell apoptosis." Cancer Res 66(11): 5901-9.

Ferrara, C, P. Brunker, et al. (2006). "Modulation of therapeutic antibody effector functions by glycosylation engineering: influence of Golgi enzyme localization domain and co-expression of heterologous betel, 4-N-acetylglucosaminyltransferase III and Golgi alpha-mannosidase II." Biotechnol Bioeng 93(5): 851-61.

Fishburn, C. S. (2008). "The pharmacology of PEGylation: balancing PD with PK to generate novel therapeutics." J Pharm Sci 97(10): 4167-83.

Gavel, Y. and G. von Heijne (1990). "Sequence differences between glycosylated and non-glycosylated Asn-X-Thr/Ser acceptor sites: implications for protein engineering." Protein Eng 3(5): 433-42.

Hinton, P. R., M. G. Johlfs, et al. (2004). "Engineered human IgG antibodies with longer serum half-lives in primates." J Biol Chem 279(8): 6213-6.

Hinton, P. R., J. M. Xiong, et al. (2006). "An engineered human IgGI antibody with longer serum half-life." J Immunol 176(1): 346-56.

Idusogie, E. E., P. Y. Wong, et al. (2001). "Engineered antibodies with increased activity to recruit complement." J Immunol 166(4): 2571-5.

Jones, A. J., D. I. Papac, et al. (2007). "Selective clearance of glycoforms of a complex glycoprotein pharmaceutical caused by terminal N-acetylglucosamine is similar in humans and cynomolgus monkeys." Glycobiology 17(5): 529-40.

Kanda, Y., T. Yamada, et al. (2007). "Comparison of biological activity among nonfucosylated therapeutic IgGI antibodies with three different N-linked Fc oligosaccharides: the high-mannose, hybrid, and complex types." Glycobiology 17(1): 104-18.

Kaneko, Y., F. Nimmerjahn, et al. (2006). "Anti-inflammatory activity of immunoglobulin G resulting from Fc sialylation." Science 313(5787): 670-3.

Kolkman, J. A. and W. P. Stemmer (2001). "Directed evolution of proteins by exon shuffling." Nat Biotechnol 19(5): 423-8.

Kopsidas, G., A. S. Roberts, et al. (2006). "In vitro improvement of a shark IgNAR antibody by Qbeta replicase mutation and ribosome display mimics in vivo affinity maturation." Immunol Lett 107(2): 163-8.

Lazar, G. A., W. Dang, et al. (2006). "Engineered antibody Fc variants with enhanced effector function." Proc Natl Acad Sci U S A 103(11): 4005-10.

Li, H., N. Sethuraman, et al. (2006). "Optimization of humanized IgGs in glycoengineered *Pichia pastoris*." Nat Biotechnol 24(2): 210-5.

Loo, D., N. Pryer, et al. (2007). "The glycotope-specific RAV12 monoclonal antibody induces oncosis in vitro and has antitumor activity against gastrointestinal adenocarcinoma tumor xenografts in vivo." Mol Cancer Ther 6(3): 856-65.

Michaelsen, T. E., A. Aase, et al. (1990). "Enhancement of complement activation and cytolysis of human IgG3 by deletion of hinge exons." Scand J Immunol 32(5): 517-28.

Natsume, A., M. In, et al. (2008). "Engineered antibodies of IgGI/IgG3 mixed isotype with enhanced cytotoxic activities." Cancer Res 68(10): 3863-72.

Norderhaug, L., O. H. Brekke, et al. (1991). "Chimeric mouse human IgG3 antibodies with an IgG4-like hinge region induce complement-mediated lysis more efficiently than IgG3 with normal hinge." Eur J Immunol 21(10): 2379-84.

Nozawa, S., D. Aoki, et al. (2004). "HMMC-1: a humanized monoclonal antibody with therapeutic potential against Mullerian duct-related carcinomas." Clin Cancer Res 10(20): 7071-8.

Peled, J. U., F. L. Kuang, et al. (2008). "The biochemistry of somatic hypermutation." Annu Rev Immunol 26: 481-511.

Petkova, S. B., S. Akilesh, et al. (2006). "Enhanced half-life of genetically engineered human IgGI antibodies in a humanized FcRn mouse model: potential application in 15 humorally mediated autoimmune disease." Int Immunol 18(12): 1759-69.

Queen, C, W. P. Schneider, et al. (1989). "A humanized antibody that binds to the interleukin 2 receptor." Proc Natl Acad Sci U S A 86(24): 10029-33.

Rammensee, H., J. Bachmann, et al. (1999). "SYFPEITHI: database for MHC ligands and peptide motifs." Immunogenetics 50(3-4): 213-9.

Shields, R. L., A. K. Namenuk, et al. (2001). "High resolution mapping of the binding site on human IgGI for Fc gamma RI, Fc gamma RII, Fc gamma RIII, and FcRn and design of IgGI variants with improved binding to the Fc gamma R." J Biol Chem 276(9): 6591-604.

Shinkawa, T., K. Nakamura, et al. (2003). "The absence of fucose but not the presence of galactose or bisecting N-acetylglucosamine of human IgGI complex-type oligosaccharides shows the critical role of enhancing antibody-dependent cellular cytotoxicity." J Biol Chem 278(5): 3466-73.

Stavenhagen, J. B., S. Gorlatov, et al. (2007). "Fc optimization of therapeutic antibodies enhances their ability to kill tumor cells in vitro and controls tumor expansion in vivo via low-affinity activating Fcgamma receptors." Cancer Res 67 (18): 8882-90.

Tan, L. K., R. J. Shopes, et al. (1990). "Influence of the hinge region on complement activation, Clq binding, and segmental flexibility in chimeric human immunoglobulins." Proc Natl Acad Sci U S A 87(1): 162-6.

Thie, FL, B. Voedisch, et al. (2009). "Affinity maturation by phage display." Methods Mol Biol 525: 309-22, xv.

Zhou, Q., S. Shankara, et al. (2008). "Development of a simple and rapid method for producing non-fucosylated oligomannose containing antibodies with increased effector function." Biotechnol Bioeng 99(3): 652-65.

Tempest, P.R., et al., "Identification of framework residues required to restore antigen binding during reshaping of a monoclonal antibody against the glycoprotein gB of human cytomegalovirus", Int. J. Biol. Macromol., vol. 17, No. 1 (1995), pp. 37-42.

Kettelborough, C.A., et al., "Humanization of a mouse monoclonal antibody by CDR-grafting: the importance of framework residues on loop conformation", Protein Engineering, vol. 4, No. 7 (1991), pp. 773-783.

Dall'Acqua, W.F., et al., "Antibody humanization by framework shuffling", Methods, vol. 26 (2005), pp. 43-60.

Holmes, M.A., et al., "Structural Effects of Framework Mutations on a Humanized Anti-Lysozyme Antibody", J. Immunol., vol. 167 (2001), pp. 296-301.

Vajdos, F.F., et al., "Comprehensive Functional Maps of the Antigen-binding Site of an Anti-ErbB2 Antibody Obtained with Shotgun Scanning Mutagenesis", J. Mol. Biol. (2002) 320, 415-428.

DePascalis, R., et al., "Grafting of 'Abbreviated' Complementarity-Determining Regions Containing Specificity-Determining Residues Essential for Ligand Contact to Engineer a Less Immunogenic Humanized Monoclonal Antibody", J. Immonol., (2002) 169, pp. 3076-3084.

Rudikoff, S., et al., "Single amino acid substitution altering antigen-binding specificity", Proc. Natl. Acad. Sci. USA, vol. 79, Mar., 1982, pp. 1979-1983.

Chen, Y., et al., "Selection and Analysis of an Optimized Anti-VEGF Antibody: Crystal Structure of an Affinity-Matured Fab in Complex with Antigen", J. Mol. Biol., (1999) 293, pp. 865-881.

Lamminmaeki, U., et al., "Crystal Structure of a Recombinant Anti-estradiol Fab Fragment in Complex with 17B-Estradiol", J. Biol. Chem., vol. 276, No. 39, Sep. 28, 2001, pp. 36687-36694.

MacCallum, R. M., et al., Antibody-antigen Interactions: Contact Analysis and Binding Site Topography, J. Mol. Biol. (1996) 262, pp. 732-745.

Padlan, E.A., et al., "Structure of an antibody-antigen complex: Crystal structure of the HyHEL-10 Fab-lysozyme complex", Proc. Natl. Acad. Sci. USA, vol. 86, Aug. 1989, pp. 5938-5942.

Wu, H., et al., "Humanization of a Murine Monoclonal Antibody by Simultaneous Optimization of Framework and CDR Residues", J. Mol. Biol. (1999) 294, pp. 151-162.

Shields, R., et al., "Lack of Fucose on Human IgGI N-Linked Oligosaccharide Improves Binding to Human FcγRIII and Antibody-dependent Cellular Toxicity", J. Biol. Chem., vol. 277, No. 30, Jul. 26, 2002, pp. 26733-26740.

Casset, F., et al., "A peptide mimetic of an anti-CD4 monoclonal antibody by rational design", Biochemical and Biophysical Research Communications, 307 (2003), pp. 198-205.

* cited by examiner

HUMANIZED ANTIBODIES WITH ANTI-TUMOR ACTIVITY

CROSS REFERENCE TO RELATED APPLICATIONS

This application is a continuation of U.S. application Ser. No. 12/725,192, which was filed on Mar. 16, 2010 and issued as U.S. Pat. No. _____ on _____, 2013, and claims priority to Australian Patent Application No. 2009901129 filed on Mar. 16, 2009, U.S. Provisional Application No. 61/160,682 filed on Mar. 16, 2009, and U.S. Provisional Application No. 61/258,517 filed on Nov. 5, 2009, the entire contents of each of these applications is incorporated herein by reference.

REFERENCE TO A SEQUENCE LISTING

This application includes a Sequence Listing submitted electronically as a text file named Humanized SC104 SEQ.txt, created on May 20, 2013 with a size of 370,000 bytes. The Sequence Listing is incorporated by reference herein.

FIELD OF THE INVENTION

The present invention relates to humanised antibodies with potent anti-tumour activity. In particular the humanised antibodies have specific binding to and direct killing of human colon tumour cells and display potent immune-mediated cytotoxic activity against human colon cancer cells in antibody-dependent cell-mediated cytotoxicity (ADCC) and complement dependent cytotoxicity (CDC) assays. In addition the present invention relates to the use of these humanised antibodies in therapy and diagnosis.

BACKGROUND

Carbohydrate structures can be tumour-specific or tumour-associated antigens and are thus the focus of many antibody-generating immunization strategies. However, generating anti-carbohydrate specific antibodies is a challenging task as they may lack specificity, affinity or are only of the IgM class (Christensen et al., 2009). Moreover, generating humanised anti-carbohydrate antibodies that have the capacity to kill cancer cells is a challenging task, a fact that is reflected in the rare number of reports on such antibodies. There is only one example of an anti-glycolipid antibody that has been successfully humanised; the antibody recognises the ganglioside GM2 and kills human tumour cells in vitro and in vivo (U.S. Pat. Nos. 6,423,511 and 6,872,392). Although not humanised there are two other examples of carbohydrate-binding antibodies that have been engineered for human administration. Firstly, anti-carbohydrate antibody RAV-12 is a chimeric mouse-human $IgG_1$ that shows in vitro and in vivo efficacy against human colon cancer cells (Loo et al., 2007). Secondly, anti-carbohydrate antibody HMMC-1 has shown in vitro efficacy against human ovarian cancer. HMMC-I is a fully human antibody generated by transchromosomal KM mice (Nozawa et al., 2004).

International patent application No. WO 2005/108430 discloses an anti-cancer mouse monoclonal antibody which is designated SC104. The disclosure of this application is incorporated herein by reference. The exact nature of antigen to which SC104 binds is unclear but WO2005/108430 suggests that the antigen is a sialyltetraosyl carbohydrate. It is also disclosed that SC104 is capable of directly inducing cell death without the need for immune effector cells.

SUMMARY OF THE INVENTION

In a first aspect the present invention provides a $V_H$ antibody binding domain, the binding domain comprising, in sequence, a first framework region (FR1), a first CDR (CDR1), a second framework region (FR2), a second CDR (CDR2), a third framework region (FR3), a third CDR (CDR3) and a fourth framework region (FR4), wherein:

the sequence of FR1 is $X_1$VQLQESGPGLVKPSETLSLTCTV$X_2$GYS$X_3X_4$ (SEQ ID NO: 95) wherein;
$X_1$ is Q or E
$X_2$ is S or T
$X_3$ is I, L or V
$X_4$ is S or T
or a sequence at least 90% or at least 95% similar, preferably at least 90% or at least 95% identical, thereto
the sequence of CDR1 is SGYSWH (SEQ ID NO: 96) or a sequence at least 80% similar, preferably at least 80% identical, thereto
the sequence of FR2 is WIRQ$X_5$PGKGL$X_6$W$X_7$G (SEQ ID NO: 97) wherein
$X_5$ is S or P
$X_6$ is Q or E
$X_7$ is M or I
or a sequence at least 90% similar, preferably at least 90% identical, thereto
the sequence of CDR2 is HIH$X_8$SGRPTY$X_9$PSL$X_{10}$S (SEQ ID NO: 98) wherein
$X_8$ is F, Y or W
$X_9$ is N or D
$X_{10}$ is K, L, H, F, R or S
or a sequence at least 90% similar, preferably at least 90% identical, thereto
the sequence of FR3 is R$X_{11}X_{12}$IS$X_{13}X_{14}$TAKNQFSLKLTSMTAADTAVYYCAR (SEQ ID NO: 99) wherein
$X_{11}$ is V or I
$X_{12}$ is T or S
$X_{13}$ is R or K
$X_{14}$ is E or D
or a sequence at least 90% or at least 95% similar, preferably at least 90% or at least 95% identical, thereto with the proviso that the residue at position 6 must be R or K
the sequence of CDR3 is KGKGSDDGLNY (SEQ ID NO: 100) or a sequence at least 90% similar, preferably at least 90% identical, thereto
the sequence of FR4 is WGQGTLVTVSS (SEQ ID NO: 101) or a sequence at least 90% similar, preferably at least 90% identical, thereto.

In a second aspect the present invention provides a $V_H$ antibody binding domain, the binding domain comprising a framework sequence and a first, second and third CDR positioned within the framework sequence in which the sequence of the framework regions is at least 90%, preferably at least 95%, identical to the sequence QVQLQESGPGLVKPSETLSLTCTVSGYS$X_3$SWIRQPPGKGLQWIGRVTIS$X_{13}$ETAKN QFSLKLTSMTAADTAVYYCARWGQGTLVTVSS (SEQ ID NO: 102);
wherein $X_3$ is I, L or V and $X_{13}$ is R or K;
and the sequence of CDR1 is SGYSWH (SEQ ID NO: 96) or a sequence at least 80% similar, preferably at least 80% identical, thereto;

the sequence of CDR2 is HIHX$_8$SGRPTYX$_9$PSLX$_{10}$S (SEQ ID NO: 98) wherein
X$_8$ is F, Y or W
X$_9$ is N or D
X$_{10}$ is K, L, H, F, R or S
or a sequence at least 90% similar, preferably at least 90% identical, thereto and; the sequence of CDR3 is KGKGS-DDGLNY (SEQ ID NO: 100) or a sequence at least 90% similar, preferably at least 90% identical, thereto.

In a third aspect the present invention provides a V$_L$ antibody binding domain, the binding domain comprising, in sequence, a first framework region (FR1), a first CDR (CDR1), a second framework region (FR2), a second CDR (CDR2), a third framework region (FR3), a third CDR (CDR3) and a fourth framework region (FR4), wherein:
the sequence of FR1 is EX$_{15}$VLTQSPGTLSLSX$_{16}$GERATLSC (SEQ ID NO: 187) wherein,
X$_{15}$ is I or N
X$_{16}$ is A or P
or a sequence at least 90% or at least 95% similar, preferably at least 90% or at least 95% identical, thereto
the sequence of CDR1 is SASSSLSYIH (SEQ ID NO: 188) or a sequence at least 90% similar, preferably at least 90% identical, thereto
the sequence of FR2 is WYQQKPGQAPRLLIY (SEQ ID NO: 189) or a sequence at least 90% similar, preferably at least 90% identical, thereto
the sequence of CDR2 is DTSNLAS (SEQ ID NO: 190) or a sequence at least 80% similar, preferably at least 80% identical, thereto
the sequence of FR3 is GIPDRFSGSGSGX$_{17}$DFTLTISRVEPEDFAVYYC (SEQ ID NO: 191) wherein,
X$_{17}$ is T or N
or a sequence at least 90% or at least 95% similar, preferably at least 90% or at least 95% identical, thereto
the sequence of CDR3 is FQGSEYPLT (SEQ ID NO: 192) or a sequence at least 80% similar, preferably at least 80% identical, thereto
the sequence of FR4 is FGQGTKLEIKR (SEQ ID NO: 193) or a sequence at least 90% similar, preferably at least 90% identical, thereto.

In a fourth aspect the present invention provides a V$_L$ antibody binding domain, the binding domain comprising a framework sequence and a first, second and third CDR positioned within the framework sequence in which the sequence of the framework regions is at least 90%, preferably at least 95% identical to the sequence EIVLTQSPGTLSLSPGER-ATLSCWYQQKPGQAPRLLIYGIPDRF-SGSGSGTDFTLTISR VEPEDFAVYYCFGQGTKLEIKR (SEQ ID NO: 194) and the sequence of CDR1 is SASSSL-SYIH (SEQ ID NO: 188) or a sequence at least 90% similar, preferably at least 90% identical, thereto;
the sequence of CDR2 is DTSNLAS (SEQ ID NO: 190) or a sequence at least 80% similar, preferably at least 80% identical, thereto and;
the sequence of CDR3 is FQGSEYPLT (SEQ ID NO: 192) or a sequence at least 80% similar, preferably at least 80% identical.

In a fifth aspect the present invention provides a V$_H$ antibody binding domain, the binding domain comprising, in sequence, a first framework region (FR1), a first CDR (CDR1), a second framework region (FR2), a second CDR (CDR2), a third framework region (FR3), a third CDR (CDR3) and a fourth framework region (FR4), wherein:

the sequence of FR1 is EVQLQQWGAGLLKPSETLSLTCAVYGYSX$_{18}$X$_{19}$ (SEQ ID NO: 201) wherein;
X$_{18}$ is I, L or V
X$_{19}$ is S or T
or a sequence at least 90% or at least 95% similar, preferably at least 90% or at least 95% identical, thereto
the sequence of CDR1 is SGYSWH (SEQ ID NO: 96) or a sequence at least 80% similar, preferably at least 80% identical, thereto
the sequence of FR2 is WIRQPPGKGLEWX$_{20}$G (SEQ ID NO: 202) wherein X$_{20}$ is M or I
or a sequence at least 90% similar, preferably at least 90% identical, thereto
the sequence of CDR2 is HIHX$_{21}$SGRPTYX$_{22}$PSLX$_{23}$S (SEQ ID NO: 98) wherein
X$_{21}$ is F, Y or W
X$_{22}$ is N or D
X$_{23}$ is K, L, H, F, R or S
or a sequence at least 90% similar, preferably at least 90% identical, thereto
the sequence of FR3 is RX$_{24}$X$_{25}$ISX$_{26}$DTSKNQFSLKLSSVTAADTAVYYCAR (SEQ ID NO: 203) wherein
X$_{24}$ is V or I
X$_{25}$ is S or T
X$_{26}$ is R or K
or a sequence at least 90% or at least 95% similar, preferably at least 90% or at least 95% identical, thereto with the proviso that the residue at position 6 must be R or K
the sequence of CDR3 is KGKGSDDGLNY (SEQ ID NO: 100) or a sequence at least 90% similar, preferably at least 90% identical, thereto
the sequence of FR4 is WGQGTLVTVSS (SEQ ID NO: 101) or a sequence at least 90% similar, preferably at least 90% identical, thereto.

In a sixth aspect the present invention provides a V$_H$ antibody binding domain, the binding domain comprising a framework sequence and a first, second and third CDR positioned within the framework sequence in which the sequence of the framework regions is at least 90%, preferably at least 95%, identical to the sequence EVQLQQWGAGLLKPSETLSLTCAVYGYSX$_{18}$SWIRQP PGKGLEWIGRVTISX$_{26}$DTSK NQFSLKLSSVTAAD-TAVYYCARWGQGTLVTVSS (SEQ ID NO: 204)
wherein X$_{18}$ is I, L or V and X$_{26}$ is R or K
and the sequence of CDR1 is SGYSWH (SEQ ID NO: 96) or a sequence at least 80% similar, preferably at least 80% identical, thereto;
the sequence of CDR2 is HIHX$_{21}$SGRPTYX$_{22}$PSLX$_{23}$S (SEQ ID NO: 98) wherein
X$_{21}$ is F, Y or W
X$_{22}$ is N or D
X$_{23}$ is K, L, H, F, R or S
or a sequence at least 90% similar, preferably at least 90% identical, thereto and; the sequence of CDR3 is KGKGS-DDGLNY (SEQ ID NO: 10) or a sequence at least 90% similar, preferably at least 90% identical, thereto.

In a seventh aspect the present invention provides a V$_L$ antibody binding domain, the binding domain comprising, in sequence, a first framework region (FR1), a first CDR (CDR1), a second framework region (FR2), a second CDR (CDR2), a third framework region (FR3), a third CDR (CDR3) and a fourth framework region (FR4), wherein:
the sequence of FR1 is EX$_{27}$VLTQSPATLSLSPGERATLSC (SEQ ID NO: 211) wherein, X$_{27}$ is I or N or a sequence at least 90% or at least 95% similar, preferably at least 90% or at least 95% identical, thereto the sequence of CDR1 is SASSSLSYIH (SEQ ID NO: 188) or a sequence at least 90% similar, preferably at least 90% identical, thereto the sequence of FR2 is WYQQKPGQAPRLLIY (SEQ ID NO: 189) or a sequence at least 90% similar, preferably at least 90% identical, thereto the sequence of CDR2 is DTSNLAS (SEQ ID NO: 190) or a sequence at least 80% similar, preferably at least 90% identical, thereto the sequence of FR3 is GIPDRFSGSGSGX$_{28}$DFTLTISRLEPEDFAVYYC (SEQ ID NO: 212) wherein, X$_{28}$ is T or N or a sequence at least 90% or at least 95% similar, preferably at least 90% or at least 95% identical, thereto the sequence of CDR3 is FQGSEYPLT (SEQ ID NO: 192) or a sequence at least 80% similar, preferably at least 80% identical, thereto the sequence of FR4 is FGGGTKVEIKR (SEQ ID NO: 193) or a sequence at least 90% similar, preferably at least 90% identical, thereto.

In an eighth aspect the present invention provides a V$_L$ antibody binding domain, the binding domain comprising a framework sequence and a first, second and third CDR positioned within the framework sequence in which the sequence of the framework regions is at least 90%, preferably at least 95%, identical to the sequence EIVLTQSPATLSLSPGER-ATLSCWYQQKPGQAPRLLIYGIPDRF-SGSGSGTDFTLTISR LEPEDFAVYYCFGGGTKVEIKR (SEQ ID NO: 213)

and the sequence of CDR1 is SASSSLSYIH (SEQ ID NO: 188) or a sequence at least 90% similar, preferably at least 90% identical, thereto;

the sequence of CDR2 is DTSNLAS (SEQ ID NO: 190) or a sequence at least 80% similar, preferably at least 80% identical, thereto and;

the sequence of CDR3 is FQGSEYPLT (SEQ ID NO: 192) or a sequence at least 80% similar, preferably at least 80% identical.

The binding domains of the present invention, when presented as part of an antibody, will bind the human colon cancer cell line Colo205. As will be understood the antibody will consist of two heavy chains, each comprising variable and constant regions, and two light chains each comprising variable and constant regions. When the claimed binding domain is a V$_H$ binding domain the antibody which binds human colon cancer cell line Colo205 will consist of two of the claimed V$_H$ binding domains, two light chains of SEQ ID NO. 7 and two heavy chain constant domains of SEQ ID NO. 92 or SEQ ID NO. 52. In a similar manner when the claimed binding domain is a V$_L$ binding domain the antibody which binds human colon cancer cell line Colo205 will consist of two of the claimed V$_L$ binding domains, two of V$_L$ constant domains of SEQ ID NO. 93 and two heavy chains of SEQ ID NO. 94 or SEQ ID NO.50.

A: Grafts containing Kabat CDR-H1; SEQ ID NO:9 is the unsubstituted V$_H$, SEQ ID NO:15 contains V$_H$ substitutions Q1E, Q46E, I48M, V67I, T68S, V71R and E72D, SEQ ID NO:7 refers to V$_L$ incorporating a single substitution A15P whilst SEQ ID NO:16 refers to a V$_L$ containing three substitutions I2N, A15P and T69N.

B: Grafts containing AbM CDR-H1; SEQ ID NO:11 refers to a V$_H$ containing no substitutions, SEQ ID NO:13 contains the V$_H$ substitutions Q1E, Q46E, I48M, V67I, T68S, V71R and E72D, SEQ ID NO:7 refers to V$_L$ incorporating a single substitution A15P and SEQ ID NO:16 refers to a V$_L$ containing three substitutions I2N, A15P and T69N.

Heavy chain amino acid substitution(s) (-□- or -○-) enhance the binding activity of 1U6A-humanised SC104 antibody variants to the antigen positive cell line C170. In comparison, the light chain amino acid substitutions appear less important in enhancing the binding activity of humanised SC104.

Figure 5:
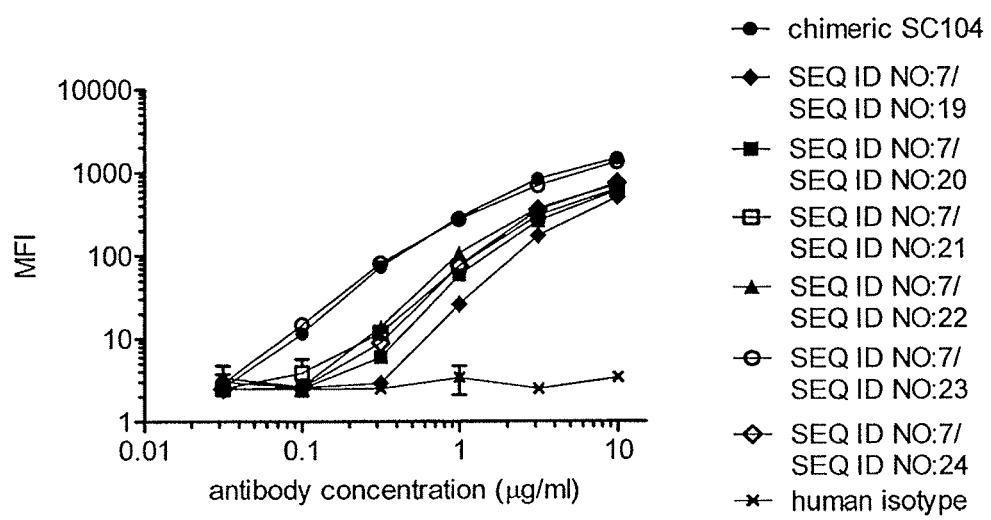

FIG. 5—Analysis of six individual V$_H$ substitutions incorporated in 1U6A-humanised antibodies containing and AbM-defined CDR-H1. The influence of the substitutions was analysed by binding activity assays to the antigen positive cell line C170 by flow cytometry. These changes were either Q46E or I48M or V67I or T68S or V71R or E72D and are described by SEQ ID NOs:19 through 24 respectively. Substitution R71 (SEQ ID NO:23) (-○-) was most advantageous in enhancing the binding potency of humanised SC104. The chimeric SC104 antibody (SEQ ID NO:4/SEQ ID NO:2) is shown as a comparator along with human IgG$_1$ isotype as a negative control. Each point represents mean±SD of three replicate samples.

Figure 6:
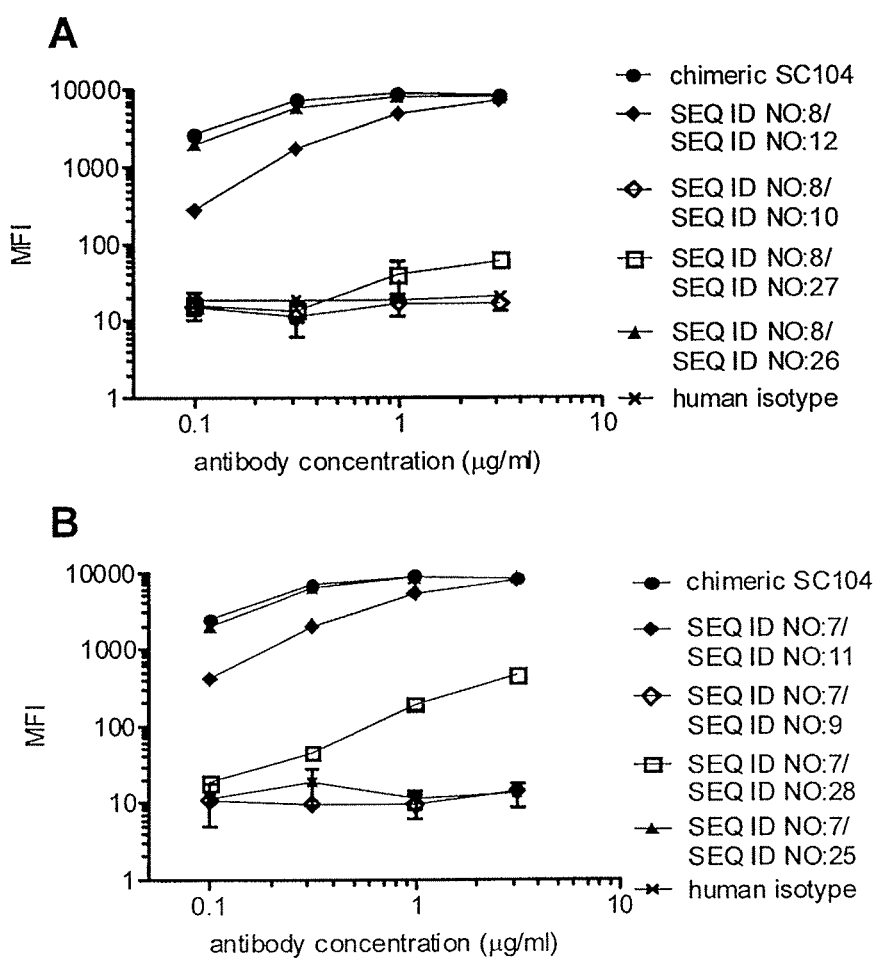

FIG. 6—V$_H$ substitution R71 (-□- or -▲-) enhances the binding activity of both AbM- and Kabat-defined CDR-H1 antibody variants to the antigen positive cell line C170 as determined by flow cytometry. The chimeric SC104 antibody (SEQ ID NO:4/SEQ ID NO:2) is shown as a comparator and the human IgG$_1$ isotype is used as a negative control. Each point represents mean±SD of three replicate samples.

A: 1QLR-based SC104 variants±V71R substitution; AbM-defined CDR-H1 grafts: SEQ ID NO:12 (−R) and SEQ ID NO:26 (+R); Kabat-defined CDR-H1 grafts: SEQ ID NO:10 (−R) and SEQ ID NO:27 (+R).

B: 1U6A-based SC 104 variants±V71R substitution. AbM-defined CDR-H1 grafts: SEQ ID NO:11 (−R) and SEQ ID NO:25 (+R); Kabat-defined CDR-H1 grafts: SEQ ID NO:9 (−R) and SEQ ID NO:28 (+R).

Figure 7:
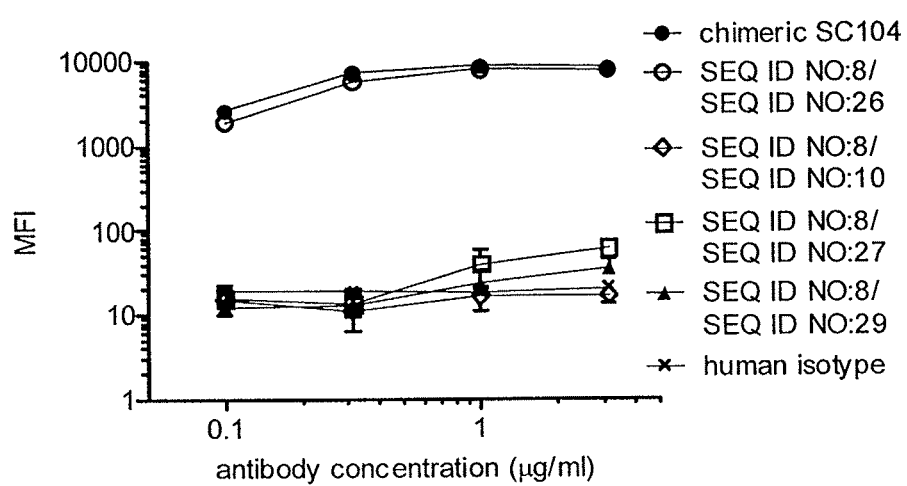

FIG. 7—Effect on binding activity of V$_H$ substitution G27Y in 1QLR-humanised SC104 variants with a Kabat-defined CDR-H1. This substitution does not enhance the binding activity of 1QLR-humanised SC104 (SEQ ID NO:27 (+R) and SEQ ID NO:29 (+R+Y) (-□- or -▲-) vs AbM-CDR-H1 containing V$_H$ SEQ ID NO:26) when examined in flow cytometry-based binding assays to the SC104 antigen positive cell line C170. For comparison, the 1QLR humanised variant incorporating a Kabat-defined CDR-H1 without R71 is shown, SEQ ID NO:10. The chimeric SC104 antibody (SEQ ID NO:4/SEQ ID NO:2) is shown as a comparator and the human IgG$_1$ isotype is used as a negative control. Each point represents mean±SD of three replicate samples.

Figure 8:
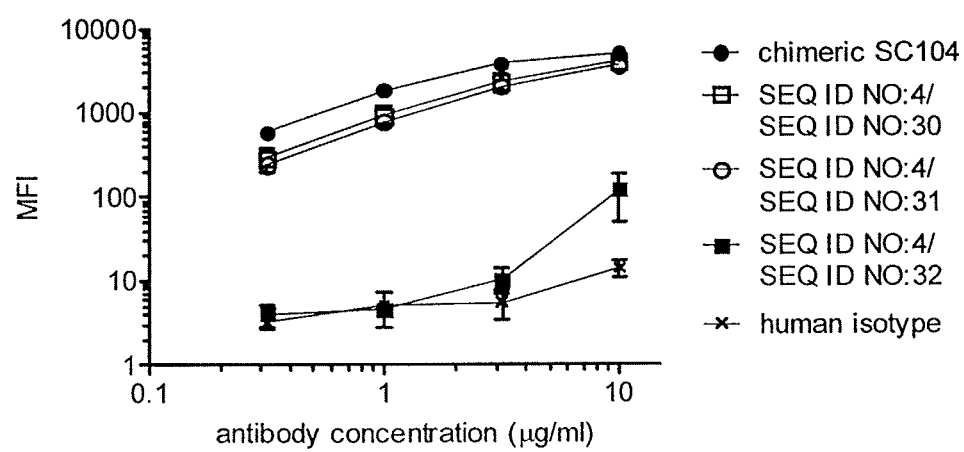

FIG. 8—Flow cytometry-based binding assay demonstrating the impact on binding activity upon removal of a predicted strong MHC class II binding peptide sequence from the framework 2:CDR-H2 boundary through substitution of F53 within CDR-H2 of chimeric SC104. Switching F53 to another aromatic residue such as W (SEQ ID NO:30) or Y (SEQ ID NO:31) (-□- or -○-) has negligible impact on binding activity whilst substitution to the preferred residue P (SEQ ID NO:32) dramatically reduces binding activity to the SC104 antigen positive cell line C170. The chimeric SC104 antibody (SEQ ID NO:4/SEQ ID NO:2) is shown as a comparator along with a human IgG$_1$ isotype negative control. Each point represents mean±SD of three replicate samples.

Figure 9:
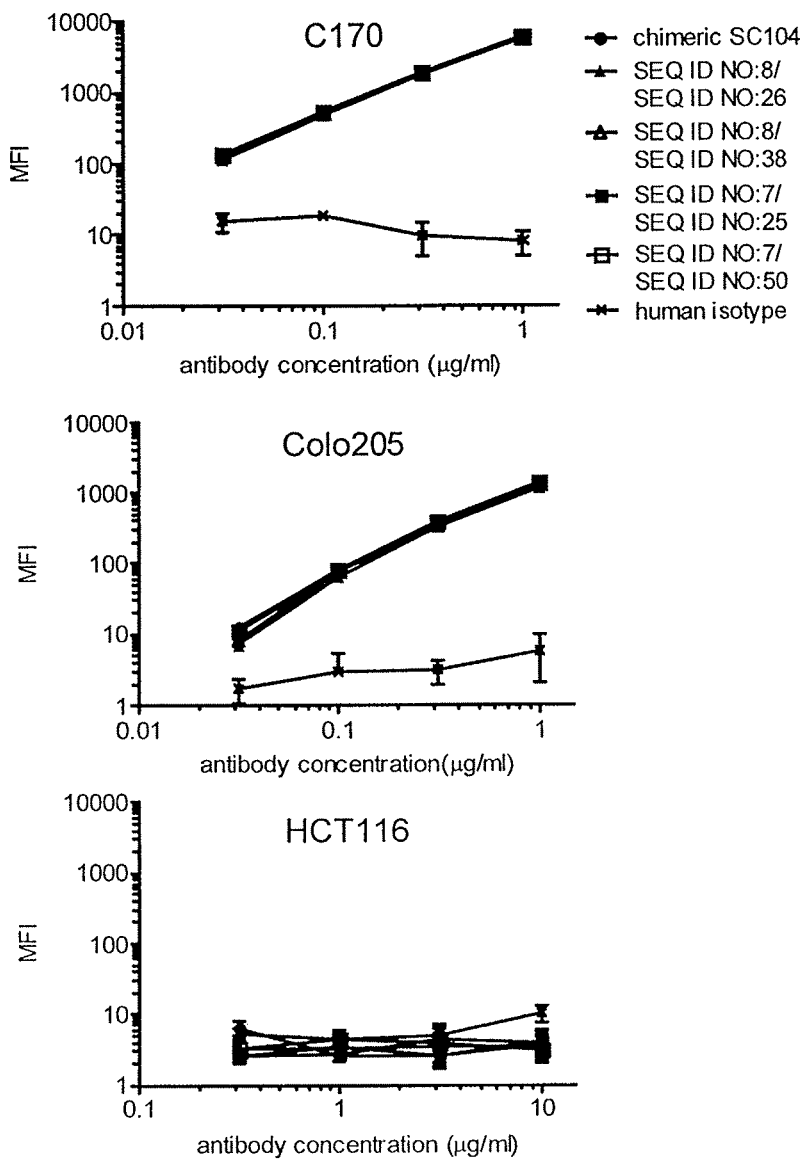

FIG. 9—Humanised SC104 variants with lower predicted immunogenicity (1U6A V$_L$/V$_H$ SEQ ID NO:7/SEQ ID NO:50; 1QLR V$_L$/V$_H$ SEQ ID NO:8/SEQ ID NO:38) are comparable to humanised antibody variants with higher predicted immunogenicity (1U6A V$_L$/V$_H$ SEQ ID NO:7/SEQ ID NO:25; 1QLR V$_L$/V$_H$ SEQ ID NO:8/SEQ ID NO:26) in terms of specificity and binding activity to antigen positive (C170, Colo205) or antigen negative (HCT-116) human colon cancer cell lines as determined by flow cytometry. The chimeric SC104 antibody (SEQ ID NO:4/SEQ ID NO:2) is shown as a comparator along with a human IgG$_1$ isotype negative control. Each point represents mean±SD of three replicate samples.

Figure 10:
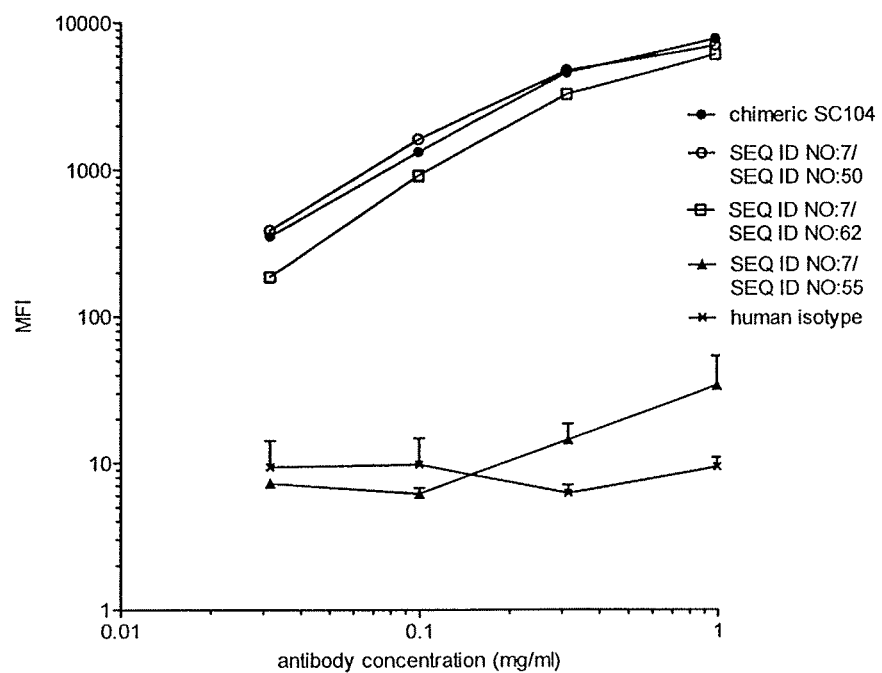

FIG. 10—Flow cytometry-based binding assay demonstrating that residues I (-○-) (SEQ ID NO:50) and L (-□-) (SEQ ID NO:62) but not C (-▲-) (SEQ ID NO:55), at position 29 in 1U6A framework 1 of variable heavy chain confer highest binding activity of humanised SC104 antibody variants with lower predicted immunogenicity to SC104 antigen positive human colon cancer cell line C170. The chimeric SC104 antibody (SEQ ID NO:4/SEQ ID NO:2) is shown as a comparator along with a human IgG$_1$ isotype negative control. Each point represents mean±SD of three replicate samples.

Figure 11:
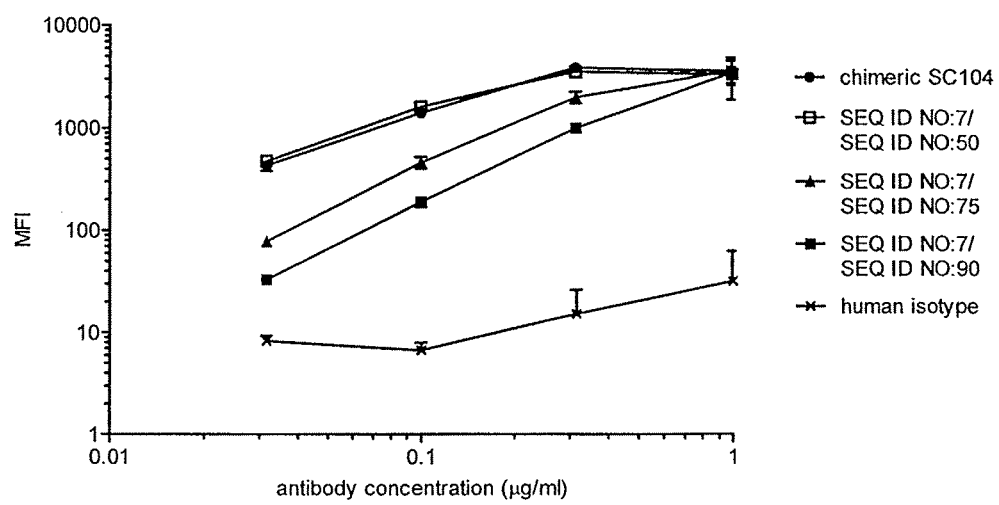

FIG. 11—Flow cytometry-based binding assay demonstrating that positive charged residues R (SEQ ID NO:50) (-□-), but not negative charged residue D (SEQ ID NO:75) (-▲-) or neutral residue W (SEQ ID NO:90) (-■-), at position 71 in 1U6A framework 3 of variable heavy chain confer highest binding activity of humanised SC 104 antibody variants with lower predicted immunogenicity to SC104 antigen positive human colon cancer cell line C170. The chimeric SC104 antibody (SEQ ID NO:4/SEQ ID NO:2) is shown as a comparator along with a human IgG$_1$ isotype negative control. Each point represents mean±SD of three replicate samples.

Figure 12:
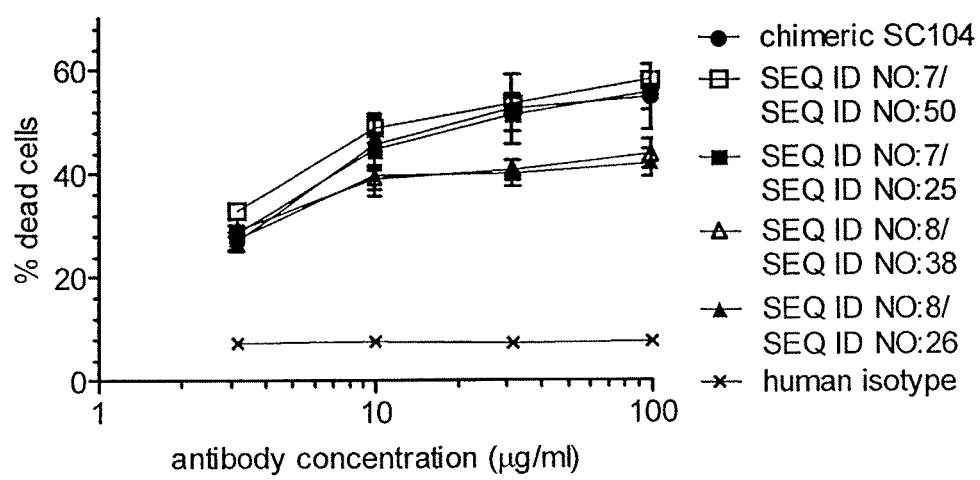

FIG. 12—SC104 antibody variants incorporating the 1U6A framework (V$_L$/V$_H$ SEQ ID NO:7/SEQ ID NO:50 and SEQ ID NO:7/SEQ ID NO:25) (-□- or -■-) have more potent direct killing activity compared with the corresponding 1QLR-derived SC104 variants (V$_L$/V$_H$ SEQ ID NO:8/SEQ ID NO:38 and SEQ ID NO:8/SEQ ID NO:26) as determined by flow cytometry using the SC104 antigen positive human colon cancer cell line C170. The chimeric SC104 antibody (SEQ ID NO:4/SEQ ID NO:2) is shown as a comparator along with a human IgG$_1$ isotype negative control. Each point represents mean±SD of three replicate samples.

Figure 13:
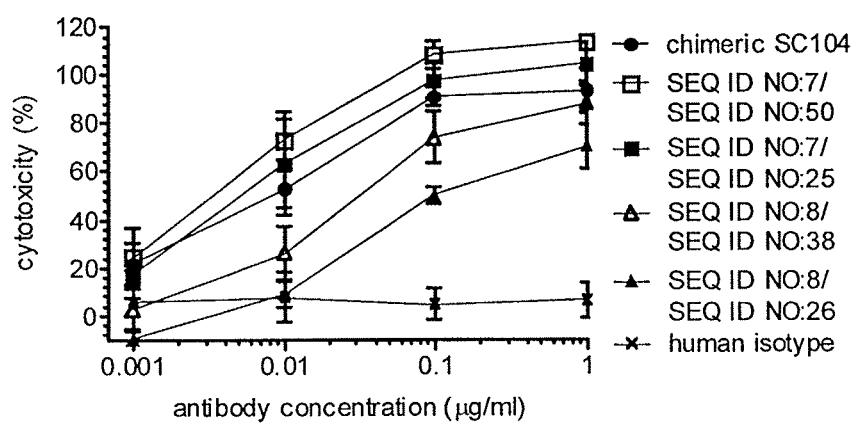

FIG. 13—Humanised SC104 antibody variants incorporating the 1U6A framework (V$_L$N$_H$ SEQ ID NO:7/SEQ ID NO:50 and SEQ ID NO:7/SEQ ID NO:25) (-□- or -■-) have higher antibody-dependent cell-mediated cytotoxicity activity compared with the corresponding 1QLR-derived SC104 variants (V$_L$/V$_H$ SEQ ID NO:8/SEQ ID NO:38 and SEQ ID NO:8/SEQ ID NO:26) as determined by LDH release assays using the SC104 antigen positive human colon cancer cell line C170. The chimeric SC104 antibody (SEQ ID NO:4/SEQ ID NO:2) is shown as a comparator and the human IgG$_1$ isotype is used as a negative control. Each point represents mean±SD of three replicate samples.

Figure 14:
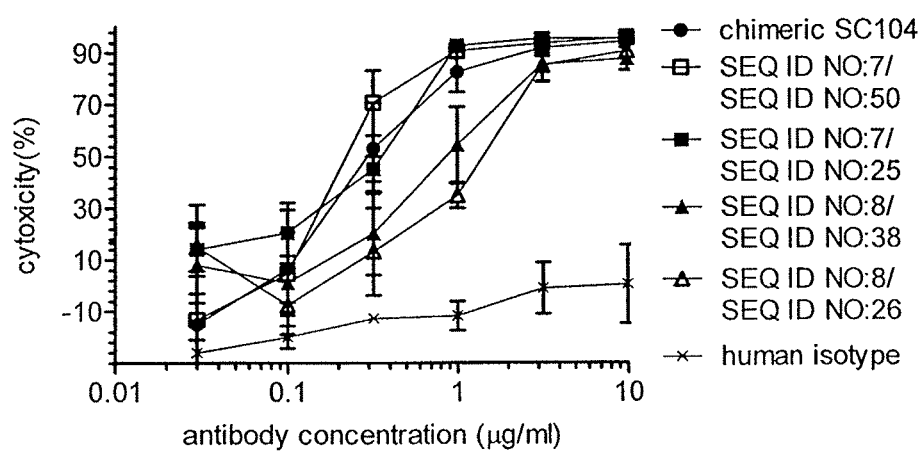

FIG. 14—SC104 antibody variants incorporating the 1U6A framework (V$_L$N$_H$ SEQ ID NO:7/SEQ ID NO:50 and SEQ ID NO:7/SEQ ID NO:25) (-□- or -■-) have more potent complement-dependent cytotoxicity compared with the corresponding 1 QLR-derived SC104 antibody variants (V$_L$N$_H$ SEQ ID NO:8/SEQ ID NO:38 and SEQ ID NO:8/SEQ ID NO:26) as determined by cell viability assays using the SC104 antigen positive human colon cancer cell line Colo205. The chimeric SC104 antibody (SEQ ID NO:4/SEQ ID NO:2) is shown as a comparator along with a human IgG$_1$ isotype negative control. Each point represents mean±SD of three replicate samples.

Figure 15:
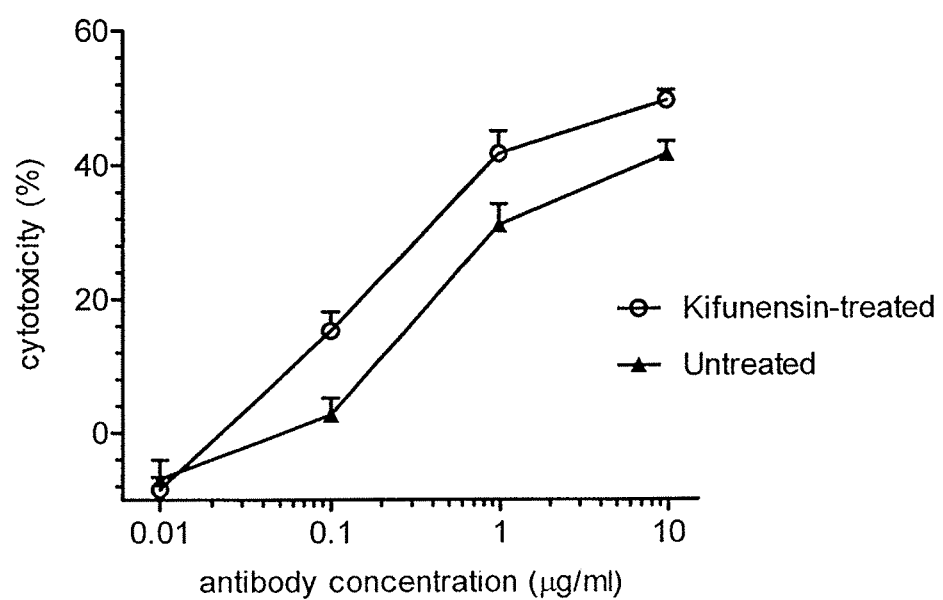

FIG. 15—Kifunensin-treated humanised SC104 antibody with lower predicted immunogenicity (SEQ ID NO:7/SEQ ID NO:50) (-○-) has higher antibody-dependent cell-mediated cytotoxicity activity compared with untreated antibody (-▲-) as assessed by LDH release assays using the SC104 antigen positive WiDr human colon cancer cell line. Each point represents mean±SD of three replicate samples.

Figure 16:
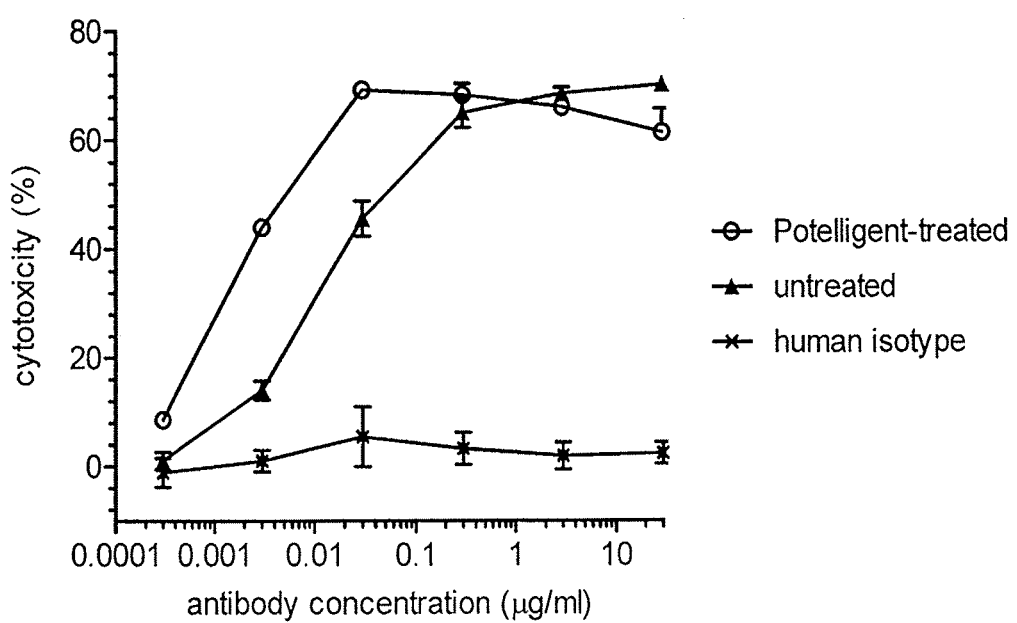

FIG. 16—Potelligent®-engineered humanised SC104 antibody with lower predicted immunogenicity (SEQ ID NO:7/SEQ ID NO:94) (-○-) has higher antibody-dependent cell-mediated cytotoxicity activity compared with untreated (SEQ ID NO:7/SEQ ID NO:50) antibody as assessed by LDH release assays using the SC104 antigen positive Colo201 human colon cancer cell line. Each point represents mean±SD of three replicate samples.

Figure 17:
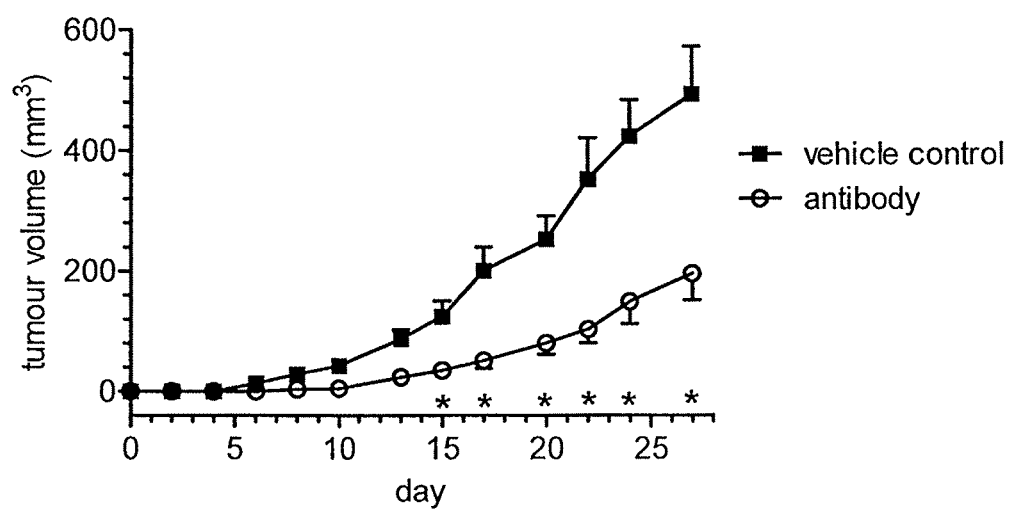
Figure 17:
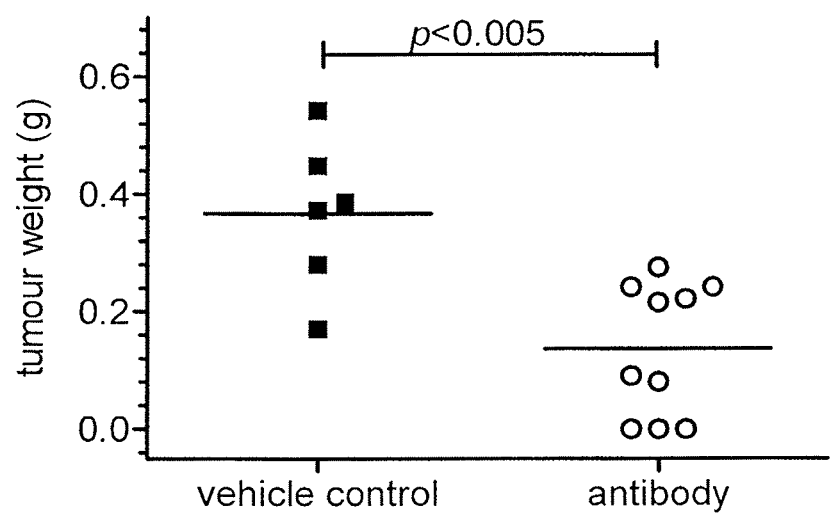

FIG. 17—Treatment of HT29 xenograft tumour-bearing mice with humanised SC104 antibody with lower predicted immunogenicity (-○-) (SEQ ID NO:7/SEQ ID NO:50) leads to significant reduced growth compared with vehicle control treatment. Top panel: mean±SEM tumour volume in groups of 6-10 mice. Asterisks indicate significant differences between treatment groups, $p<0.05$ Mann-Whitney test. Bottom panel: mean and individual tumour weight at end of study. P value as determined by Mann-Whitney test.

Figure 18:
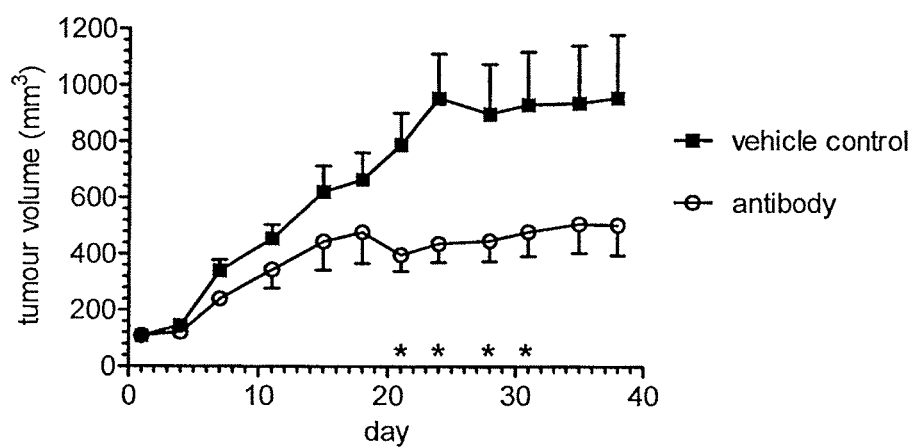

FIG. 18—Treatment of Colo201 xenograft tumour-bearing mice with Potelligent®-engineered humanised SC104 antibody with lower predicted immunogenicity (-○-) (SEQ ID NO:7/SEQ ID NO:94) leads to significant reduced tumour volume compared with vehicle control treatment. Mean±SEM in groups of 10 mice. Asterisks indicate significant differences between treatment groups, $p<0.05$ t-test.

DETAILED DESCRIPTION OF THE INVENTION

The present invention relates to humanised anti-cancer binding domains. These binding domains are based on the mouse antibody SC104 (WO 2005/108430) and comprise modified human framework sequences to increase binding and activity, and decrease predicted immunogenicity. As will be appreciated by people skilled in the art, the sequences developed and described herein may be further modified to increase binding by affinity maturation and to increase Fc-mediated effector function. The binding domains described herein can be used either alone or in combination for diagnosis and/or treatment of human cancers, for example colorectal, pancreatic, ovarian and lung cancer.

In a first aspect the present invention provides a $V_H$ antibody binding domain, the binding domain comprising, in sequence, a first framework region (FR1), a first CDR (CDR1), a second framework region (FR2), a second CDR (CDR2), a third framework region (FR3), a third CDR (CDR3) and a fourth framework region (FR4), wherein:

the sequence of FR1 is $X_1$VQLQESGPGLVKPSETLSLTCTV$X_2$GYS$X_3X_4$ (SEQ ID NO: 95) wherein;
$X_1$ is Q or E
$X_2$ is S or T
$X_3$ is I, L or V
$X_4$ is S or T
or a sequence at least 90% or at least 95% similar, preferably at least 90% or at least 95% identical, thereto
the sequence of CDR1 is SGYSWH (SEQ ID NO: 96) or a sequence at least 80% similar, preferably at least 80% identical, thereto
the sequence of FR2 is WIRQ$X_5$PGKGL$X_6$W$X_7$G (SEQ ID NO: 97) wherein
$X_5$ is S or P
$X_6$ is Q or E
$X_7$ is M or I
or a sequence at least 90% similar, preferably at least 90% identical, thereto
the sequence of CDR2 is HIH$X_8$SGRPTY$X_9$PSL$X_{10}$S (SEQ ID NO: 98) wherein
$X_8$ is F, Y or W
$X_9$ is N or D
$X_{10}$ is K, L, H, F, R or S
or a sequence at least 90% similar, preferably at least 90% identical, thereto
the sequence of FR3 is RX$_{11}$X$_{12}$ISX$_{13}$X$_{14}$TAKNQFSLKLTSMTAADTAVYYCAR (SEQ ID NO: 99) wherein
$X_{11}$ is V or I
$X_{12}$ is T or S
$X_{13}$ is R or K
$X_{14}$ is E or D
or a sequence at least 90% or at least 95% similar, preferably at least 90% or at least 95% identical, thereto with the proviso that the residue at position 6 must be R or K
the sequence of CDR3 is KGKGSDDGLNY (SEQ ID NO: 100) or a sequence at least 90% similar, preferably at least 90% identical, thereto
the sequence of FR4 is WGQGTLVTVSS (SEQ ID NO: 101) or a sequence at least 90% similar, preferably at least 90% identical, thereto.

In a second aspect the present invention provides a $V_H$ antibody binding domain, the binding domain comprising a framework sequence and a first, second and third CDR positioned within the framework sequence in which the sequence of the framework regions is at least 90%, preferably at least 95%, identical to the sequence QVQLQESGPGLVKPSETLSLTCTVSGYS$X_3$SWIRQPPGKGLQWIGRVTIS$X_{13}$ETAKN QFSLKLTSMTAADTAVYYCARWGQGTLVTVSS (SEQ ID NO: 102);
wherein $X_3$ is I, L or V and $X_{13}$ is R or K;
and the sequence of CDR1 is SGYSWH (SEQ ID NO: 96) or a sequence at least 80% similar, preferably at least 80% identical, thereto;
the sequence of CDR2 is HIH$X_8$SGRPTY$X_9$PSL$X_{10}$S (SEQ ID NO: 98) wherein
$X_8$ is F, Y or W
$X_9$ is N or D
$X_{10}$ is K, L, H, F, R or S
or a sequence at least 90% similar, preferably at least 90% identical, thereto and;
the sequence of CDR3 is KGKGSDDGLNY (SEQ ID NO: 100) or a sequence at least 90% similar, preferably at least 90% identical, thereto.

Preferred sequences for FR1, CDR1, FR2, CDR2, FR3, CDR3, and FR4 are as follows:—

FR1 is selected from the group consisting of QVQLQESGPGLVKPSETLSLTCTVSGYSIS (SEQ ID NO: 103), QVQLQESGPGLVKPSETLSLTCTVSGYSIT (SEQ ID NO: 104), QVQLQESGPGLVKPSETLSLTCTVSGYSLS (SEQ ID NO: 105), QVQLQESGPGLVKPSETLSLTCTVSGYSLT (SEQ ID NO: 106), QVQLQESGPGLVKPSETLSLTCTVSGYSVS (SEQ ID NO: 107), QVQLQESGPGLVKPSETLSLTCTVSGYSVT (SEQ ID NO: 108), QVQLQESGPGLVKPSETLSLTCTVTGYSIS (SEQ ID NO: 109), QVQLQESGPGLVKPSETLSLTCTVTGYSIT (SEQ ID NO: 110), QVQLQESGPGLVKPSETLSLTCTVTGYSLS (SEQ ID NO: 111), QVQLQESGPGLVKPSETLSLTCTVTGYSLT (SEQ ID NO: 112), QVQLQESGPGLVKPSETLSLTCTVTGYSVS (SEQ ID NO: 113), QVQLQESGPGLVKPSETLSLTCTVTGYSVT (SEQ ID NO: 114), EVQLQESGPGLVKPSETLSLTCTVSGYSIS (SEQ ID NO: 115), EVQLQESGPGLVKPSETLSLTCTVSGYSIT (SEQ ID NO: 116), EVQLQESGPGLVKPSETLSLTCTVSGYSLS (SEQ ID NO: 117), EVQLQESGPGLVKPSETLSLTCTVSGYSLT (SEQ ID NO: 118), EVQLQESGPGLVKPSETLSLTCTVSGYSVS (SEQ ID NO: 119), EVQLQESGPGLVKPSETLSLTCTVSGYSVT (SEQ ID NO: 120), EVQLQESGPGLVKPSETLSLTCTVTGYSIS (SEQ ID NO: 121), EVQLQESGPGLVKPSETLSLTCTVTGYSIT (SEQ ID NO: 122), EVQLQESGPGLVKPSETLSLTCTVTGYSLS (SEQ ID NO: 123), EVQLQESGPGLVKPSETLSLTCTVTGYSLT (SEQ ID NO: 124), EVQLQESGPGLVKPSETLSLTCTVSTGYSVS (SEQ ID NO: 125), and EVQLQESG-PGLVKPSETLSLTCTVTGYSVT (SEQ ID NO: 126);

CDR1 is SGYSWH (SEQ ID NO: 96);

FR2 is selected from the group consisting of WIRQSPGKGLQWMG (SEQ ID NO: 127), WIRQSPGKGLQWMG (SEQ ID NO: 128), WIRQSPGKGLEWIG (SEQ ID NO: 129), WIRQSPGKGLEWMG (SEQ ID NO: 130), WIRQPPGKGLQWIG (SEQ ID NO: 131), WIRQPPGKGLQWMG (SEQ ID NO: 132), WIRQPPGKGLEWIG (SEQ ID NO: 133), and WIRQPPGKGLEWMG (SEQ ID NO: 134);

CDR2 is selected from the group consisting of HIHFSGRPTYNPSLSS (SEQ ID NO: 135), HIHFSGRPTYNPSLKS (SEQ ID NO: 136), HIHFSGRPTYNPSLLS (SEQ ID NO: 137), HIHFSGRPTYNPSLHS (SEQ ID NO: 138), HIHFSGRPTYNPSLFS (SEQ ID NO: 139), HIHFSGRPTYNPSLRS (SEQ ID NO: 140), HIHWSGRPTYNPSLSS (SEQ ID NO: 141), HIHWSGRPTYNPSLKS (SEQ ID NO: 142), HIHWSGRPTYNPSLLS (SEQ ID NO: 143), HIHWSGRPTYNPSLHS (SEQ ID NO: 144), HIHWSGRPTYNPSLFS (SEQ ID NO: 145), HIHWSGRPTYNPSLRS (SEQ ID NO: 146), HIHYSGRPTYNPSLSS (SEQ ID NO: 147), HIHYSGRPTYNPSLKS (SEQ ID NO: 148), HIHYSGRPTYNPSLLS (SEQ ID NO: 149), HIHYSGRPTYNPSLHS (SEQ ID NO: 150), HIHYSGRPTYNPSLFS (SEQ ID NO: 151), HIHYSGRPTYNPSLRS (SEQ ID NO: 152), HIHFSGRPTYDPSLSS (SEQ ID NO: 153), HIHFSGRPTYDPSLKS (SEQ ID NO: 154), HIHFSGRPTYDPSLLS (SEQ ID NO: 155), HIHFSGRPTYDPSLHS (SEQ ID NO: 156), HIHFSGRPTYDPSLFS (SEQ ID NO: 157), HIHFSGRPTYDPSLRS (SEQ ID NO: 158), HIHWSGRPTYDPSLSS (SEQ ID NO: 159), HIHWSGRPTYDPSLKS (SEQ ID NO: 160), HIHWSGRPTYDPSLLS (SEQ ID NO: 161), HIHWSGRPTYDPSLHS (SEQ ID NO: 162), HIHWSGRPTYDPSLFS (SEQ ID NO: 163), HIHWSGRPTYDPSLRS (SEQ ID NO: 164), HIHYSGRPTYDPSLSS (SEQ ID NO: 165), HIHYSGRPTYDPSLKS (SEQ ID NO: 166), HIHYSGRPTYDPSLLS (SEQ ID NO: 167), HIHYSGRPTYDPSLHS (SEQ ID NO: 168), HIHYSGRPTYDPSLFS (SEQ ID NO: 169), and HIHYSGRPTYDPSLRS (SEQ ID NO: 170);

FR3 is selected from the group consisting of RVTISRETAKNQFSLKLTSMTAADTAVYYCAR (SEQ ID NO: 171), RVTISRDTAKNQFSLKLTSMTAADTAVYYCAR (SEQ ID NO: 172), RVTISKETAKNQFSLKLTSMTAADTAVYYCAR (SEQ ID NO: 173), RVTISKDTAKNQFSLKLTSMTAADTAVYYCAR (SEQ ID NO: 174), RVSISRETAKNQFSLKLTSMTAADTAVYYCAR (SEQ ID NO: 175), RVSISRDTAKNQFSLKLTSMTAADTAVYYCAR (SEQ ID NO: 176), RVSISKETAKNQFSLKLTSMTAADTAVYYCAR (SEQ ID NO: 177), RVSISKDTAKNQFSLKLTSMTAADTAVYYCAR (SEQ ID NO: 178), RITISRETAKNQFSLKLTSMTAADTAVYYCAR (SEQ ID NO: 179), RITISRDTAKNQFSLKLTSMTAADTAVYYCAR (SEQ ID NO: 180), RITISKETAKNQFSLKLTSMTAADTAVYYCAR (SEQ ID NO: 181), RITISKDTAKNQFSLKLTSMTAADTAVYYCAR (SEQ ID NO: 182), RISISRETAKNQFSLKLTSMTAADTAVYYCAR (SEQ ID NO: 183), RISISRDTAKNQFSLKLTSMTAADTAVYYCAR (SEQ ID NO: 184), RISISKETAKNQFSLKLTSMTAADTAVYYCAR (SEQ ID NO: 185), and RISISKDTAKNQFSLKLTSMTAADTAVYYCAR (SEQ ID NO: 186);

CDR3 is KGKGSDDGLNY (SEQ ID NO: 100); and

FR4 is WGQGTLVTVSS (SEQ ID NO: 101).

In a third aspect the present invention provides a VL antibody binding domain, the binding domain comprising, in sequence, a first framework region (FR1), a first CDR (CDR1), a second framework region (FR2), a second CDR (CDR2), a third framework region (FR3), a third CDR (CDR3) and a fourth framework region (FR4), wherein:

the sequence of FR1 is $EX_{15}VLTQSPGTLSLSX_{16}GERATLSC$ (SEQ ID NO: 187) wherein, $X_{15}$ is I or N $X_{16}$ is A or P or a sequence at least 90% or at least 95% similar, preferably at least 90% or at least 95% identical, thereto the sequence of CDR1 is SASSSLSYIH (SEQ ID NO: 188) or a sequence at least 90% similar, preferably at least 90% identical, thereto the sequence of FR2 is WYQQKPGQAPRLLIY (SEQ ID NO: 189) or a sequence at least 90% similar, preferably at least 90% identical, thereto the sequence of CDR2 is DTSNLAS (SEQ ID NO: 190) or a sequence at least 80% similar, preferably at least 80% identical, thereto the sequence of FR3 is $GIPDRFSGSGSGX_{17}DFTLTISRVEPEDFAVYYC$ (SEQ ID NO: 191) wherein, $X_{17}$ is T or N or a sequence at least 90% or at least 95% similar, preferably at least 90% or at least 95% identical, thereto the sequence of CDR3 is FQGSEYPLT (SEQ ID NO: 192) or a sequence at least 80% similar, preferably at least 80% identical, thereto the sequence of FR4 is FGQGTKLEIKR (SEQ ID NO: 193) or a sequence at least 90% similar, preferably at least 90% identical, thereto.

In a fourth aspect the present invention provides a $V_L$ antibody binding domain, the binding domain comprising a framework sequence and a first, second and third CDR positioned within the framework sequence in which the sequence of the framework regions is at least 90%, preferably at least 95% identical to the sequence EIVLTQSPGTLSLSPGERATLSCWYQQKPGQAPRLLIYGIPDRFSGSGSGTDFTLTISR VEPEDFAVYYCFGQGTKLEIKR (SEQ ID NO: 194)

and the sequence of CDR1 is SASSSLSYIH (SEQ ID NO: 188) or a sequence at least 90% similar, preferably at least 90% identical, thereto;

the sequence of CDR2 is DTSNLAS (SEQ ID NO: 190) or a sequence at least 80% similar, preferably at least 80% identical, thereto and;

the sequence of CDR3 is FQGSEYPLT (SEQ ID NO: 192) or a sequence at least 80% similar, preferably at least 80% identical.

Preferred sequences for FR1, CDR1, FR2, CDR2, FR3, CDR3, and FR4 are as follows:—

FR1 is selected from the group EIVLTQSPGTLSLSPGERATLSC (SEQ ID NO: 195), EIVLTQSPGTLSLSAGERATLSC (SEQ ID NO: 196), ENVLTQSPGTLSLSPGERATLSC (SEQ ID NO: 197), and ENVLTQSPGTLSLSAGERATLSC (SEQ ID NO: 198).

CDR1 is SASSSLSYIH (SEQ ID NO: 188);

FR2 is WYQQKPGQAPRLLIY (SEQ ID NO: 189);

CDR2 is DTSNLAS (SEQ ID NO: 190);
FR3 is GIPDRFSGSGSGTDFTLTISRVEPEDFAVYYC (SEQ ID NO: 199) or GIPDRFSGSGSGNDFTLTISRVEPEDFAVYYC (SEQ ID NO: 200);
CDR3 is FQGSEYPLT (SEQ ID NO: 192); and
FR4 is FGQGTKLEIKR (SEQ ID NO: 193).

In a fifth aspect the present invention provides a VH antibody binding domain, the binding domain comprising, in sequence, a first framework region (FR1), a first CDR (CDR1), a second framework region (FR2), a second CDR (CDR2), a third framework region (FR3), a third CDR (CDR3) and a fourth framework region (FR4), wherein:
the sequence of FR1 is EVQLQQWGAGLLKPSETLSLTCAVYGYSX$_{18}$X$_{19}$ (SEQ ID NO: 201) wherein;
X$_{18}$ is I, L or V
X$_{19}$ is S or T
or a sequence at least 90% or at least 95% similar, preferably at least 90% or at least 95% identical, thereto
the sequence of CDR1 is SGYSWH (SEQ ID NO: 96) or a sequence at least 80% similar, preferably at least 80% identical, thereto
the sequence of FR2 is WIRQPPGKGLEWX$_{20}$G (SEQ ID NO: 202) wherein
X$_{20}$ is M or I
or a sequence at least 90% similar, preferably at least 90% identical, thereto
the sequence of CDR2 is HIHX$_{21}$SGRPTYX$_{22}$PSLX$_{23}$S (SEQ ID NO: 98) wherein
X$_{21}$ is F, Y or W
X$_{22}$ is N or D
X$_{23}$ is K, L, H, F, R or S
or a sequence at least 90% similar, preferably at least 90% identical, thereto
the sequence of FR3 is RX$_{24}$X$_{25}$ISX$_{26}$DTSKNQFSLKLSSVTAADTAVYYCAR (SEQ ID NO: 203) wherein
X$_{24}$ is V or I
X$_{25}$ is S or T
X$_{26}$ is R or K
or a sequence at least 90% or at least 95% similar, preferably at least 90% or at least 95% identical, thereto with the proviso that the residue at position 6 must be R or K
the sequence of CDR3 is KGKGSDDGLNY (SEQ ID NO: 100) or a sequence at least 90% similar, preferably at least 90% identical, thereto
the sequence of FR4 is WGQGTLVTVSS (SEQ ID NO: 101) or a sequence at least 90% similar, preferably at least 90% identical, thereto.

In a sixth aspect the present invention provides a V$_H$ antibody binding domain, the binding domain comprising a framework sequence and a first, second and third CDR positioned within the framework sequence in which the sequence of the framework regions is at least 90%, preferably at least 95%, identical to the sequence EVQLQQWGAGLLKPSETLSLTCAVYGYSX$_{18}$SWIRQPPGKGLEWIGRVTISX$_{26}$DTSK NQFSLKLSSVTAADTAVYYCARWGQGTLVTVSS (SEQ ID NO: 204)
wherein X$_{18}$ is I, L or V and X$_{26}$ is R or K
and the sequence of CDR1 is SGYSWH (SEQ ID NO: 96) or a sequence at least 80% similar, preferably at least 80% identical, thereto;
the sequence of CDR2 is HIHX$_{21}$SGRPTYX$_{22}$PSLX$_{23}$S (SEQ ID NO: 98) wherein
X$_{21}$ is F, Y or W
X$_{22}$ is N or D
X$_{23}$ is K, L, H, F, R or S
or a sequence at least 90% similar, preferably at least 90% identical, thereto and;
the sequence of CDR3 is KGKGSDDGLNY (SEQ ID NO: 100) or a sequence at least 90% similar, preferably at least 90% identical, thereto.

Preferred sequences for FR1, CDR1, FR2, CDR2, FR3, CDR3, and FR4 are as follows:—
FR1 is selected from the group consisting of EVQLQQWGAGLLKPSETLSLTCAVYGYSIS (SEQ ID NO: 205), EVQLQQWGAGLLKPSETLSLTCAVYGYSIT (SEQ ID NO: 206), EVQLQQWGAGLLKPSETLSLTCAVYGYSLS (SEQ ID NO: 207), EVQLQQWGAGLLKPSETLSLTCAVYGYSLT (SEQ ID NO: 208), EVQLQQWGAGLLKPSETLSLTCAVYGYSVS (SEQ ID NO: 209), and EVQLQQWGAGLLKPSETLSLTCAVYGYSVT (SEQ ID NO: 210);
CDR1 is SGYSWH (SEQ ID NO: 96);
FR2 is WIRQPPGKGLEWIG (SEQ ID NO: 133) or WIRQPPGKGLEWMG (SEQ ID NO: 134);
CDR2 is selected from the group consisting of HIHFSGRPTYNPSLSS (SEQ ID NO: 135), HIHFSGRPTYNPSLKS (SEQ ID NO: 136), HIHFSGRPTYNPSLLS (SEQ ID NO: 137), HIHFSGRPTYNPSLHS (SEQ ID NO: 138), HIHFSGRPTYNPSLFS (SEQ ID NO: 139), HIHFSGRPTYNPSLRS (SEQ ID NO: 140), HIHWSGRPTYNPSLSS (SEQ ID NO: 141), HIHWSGRPTYNPSLKS (SEQ ID NO: 142), HIHWSGRPTYNPSLLS (SEQ ID NO: 143), HIHWSGRPTYNPSLHS (SEQ ID NO: 144), HIHWSGRPTYNPSLFS (SEQ ID NO: 145), HIHWSGRPTYNPSLRS (SEQ ID NO: 146), HIHYSGRPTYNPSLSS (SEQ ID NO: 147), HIHYSGRPTYNPSLKS (SEQ ID NO: 148), HIHYSGRPTYNPSLLS (SEQ ID NO: 149), HIHYSGRPTYNPSLHS (SEQ ID NO: 150), HIHYSGRPTYNPSLFS (SEQ ID NO: 151), HIHYSGRPTYNPSLRS (SEQ ID NO: 152), HIHFSGRPTYDPSLSS (SEQ ID NO: 153), HIHFSGRPTYDPSLKS (SEQ ID NO: 154), HIHFSGRPTYDPSLLS (SEQ ID NO: 155), HIHFSGRPTYDPSLHS (SEQ ID NO: 156), HIHFSGRPTYDPSLFS (SEQ ID NO: 157), HIHFSGRPTYDPSLRS (SEQ ID NO: 158), HIHWSGRPTYDPSLSS (SEQ ID NO: 159), HIHWSGRPTYDPSLKS (SEQ ID NO: 160), HIHWSGRPTYDPSLLS (SEQ ID NO: 161), HIHWSGRPTYDPSLHS (SEQ ID NO: 162), HIHWSGRPTYDPSLFS (SEQ ID NO: 163), HIHWSGRPTYDPSLRS (SEQ ID NO: 164), HIHYSGRPTYDPSLSS (SEQ ID NO: 165), HIHYSGRPTYDPSLKS (SEQ ID NO: 166), HIHYSGRPTYDPSLLS (SEQ ID NO: 167), HIHYSGRPTYDPSLHS (SEQ ID NO: 168), HIHYSGRPTYDPSLFS (SEQ ID NO: 169), and HIHYSGRPTYDPSLRS (SEQ ID NO: 170);
FR3 is selected from the group consisting of RVTISRDTSKNQFSLKLSSVTAADTAVYYCAR (SEQ ID NO: 218), RVTISKDTSKNQFSLKLSSVTAADTAVYYCAR (SEQ ID NO: 219), RVSISRDTSKNQFSLKLSSVTAADTAVYYCAR (SEQ ID NO: 220), RVSISKDTSKNQFSLKLSSVTAADTAVYYCAR (SEQ ID NO: 221), RITISRDTSKNQFSLKLSSVTAADTAVYYCAR (SEQ ID NO: 222), RITISKDTSKNQFSLKLSSVTAADTAVYYCAR (SEQ ID NO: 223), RISISRDTSKNQFSLKLSSVTAADTAVYYCAR (SEQ ID NO: 224), RISISKDTSKNQFSLKLSSVTAADTAVYYCAR (SEQ ID NO: 225).
CDR3 is KGKGSDDGLNY (SEQ ID NO: 100).
FR4 is WGQGTLVTVSS (SEQ ID NO: 101).

In a seventh aspect the present invention provides a V$_L$ antibody binding domain, the binding domain comprising, in sequence, a first framework region (FR1), a first CDR (CDR1), a second framework region (FR2), a second CDR (CDR2), a third framework region (FR3), a third CDR (CDR3) and a fourth framework region (FR4), wherein:
the sequence of FR1 is EX$_{27}$VLTQSPATLSLSPGERATLSC (SEQ ID NO: 211) wherein,
X$_{27}$ is I or N
or a sequence at least 90% or at least 95% similar, preferably at least 90% or at least 95% identical, thereto
the sequence of CDR1 is SASSSLSYIH (SEQ ID NO: 188) or a sequence at least 90% similar, preferably at least 90% identical, thereto
the sequence of FR2 is WYQQKPGQAPRLLIY (SEQ ID NO: 189) or a sequence at least 90% similar, preferably at least 90% identical, thereto
the sequence of CDR2 is DTSNLAS (SEQ ID NO: 190) or a sequence at least 80% similar, preferably at least 90% identical, thereto
the sequence of FR3 is GIPDRFSGSGSGX$_{28}$DFTLTISRLEPEDFAVYYC (SEQ ID NO: 212) wherein,
X$_{28}$ is T or N
or a sequence at least 90% or at least 95% similar, preferably at least 90% or at least 95% identical, thereto
the sequence of CDR3 is FQGSEYPLT (SEQ ID NO: 192) or a sequence at least 80% similar, preferably at least 80% identical, thereto
the sequence of FR4 is FGGGTKVEIKR (SEQ ID NO: 193) or a sequence at least 90% similar, preferably at least 90% identical, thereto.

In an eighth aspect the present invention provides a V$_L$ antibody binding domain, the binding domain comprising a framework sequence and a first, second and third CDR positioned within the framework sequence in which the sequence of the framework regions is at least 90%, preferably at least 95%, identical to the sequence EIVLTQSPATLSLSPGER-ATLSCWYQQKPGQAPRLLIYGIPDRF-SGSGSGTDFTLTISR LEPEDFAVYYCFGGGTKVEIKR (SEQ ID NO: 213)
and the sequence of CDR1 is SASSSLSYIH (SEQ ID NO: 188) or a sequence at least 90% similar, preferably at least 90% identical, thereto;
the sequence of CDR2 is DTSNLAS (SEQ ID NO: 190) or a sequence at least 80% similar, preferably at least 80% identical, thereto and;
the sequence of CDR3 is FQGSEYPLT (SEQ ID NO: 192) or a sequence at least 80% similar, preferably at least 80% identical.

Preferred sequences for FR1, CDR1, FR2, CDR2, FR3, CDR3, and FR4 are as follows:—
FR1 is selected from the group EIVLTQSPATLSLSPGER-ATLSC (SEQ ID NO: 214) or ENVLTQSPATLSLSPGER-ATLSC (SEQ ID NO: 215).
CDR1 is SASSSLSYIH (SEQ ID NO: 188).
FR2 is WYQQKPGQAPRLLIY (SEQ ID NO: 189).
CDR2 is DTSNLAS (SEQ ID NO: 190).
FR3 is GIPDRFSGSGSGTDFTLTISRLEPEDFAVYYC (SEQ ID NO: 216) or GIPDRFSGSGSGNDFTLTISR-LEPEDFAVYYC (SEQ ID NO: 217).
CDR3 is FQGSEYPLT (SEQ ID NO: 192).
FR4 is FGGGTKVEIKR (SEQ ID NO: 193).

In preferred embodiments of the present invention the V$_H$ and V$_L$ antibody binding domains of the present invention further comprise a constant domain. The constant domain may be a human or non-human primate, preferably human, constant region. In one embodiment the sequence of the heavy chain constant domain is (SEQ ID NO: 52)
ASTKNPDVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPGK;
or (SEQ ID NO: 92)
ASTKGPSVFPLAPSSKSTSGGTAALGCLVKDYFPEPVTVSWNSGALTSGV
HTFPAVLQSSGLYSLS SVVTVPSSSLGTQTYICNVNHKPSNTKVDKKVE
PKSCDKTHTCPPCPAPELLGGP SVFLFPPKPKDTLMISRTPEVTCVVVD
VSHEDPEVKFNWYVDGVEVHNAKTKPREEQYNSTYRVVSVLTVLHQDWLN
GKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKS
RWQQGNVFSCSVMHEALHNHYTQKSLSLSPGK;
or (SEQ ID NO: 53)
ASTKNPDVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPDVFLFPPKPKDTLMISRTPEVTCVVVDVS
HEDPEVKFNWYVDGVEVHNAKTKPREEQYNATYRVVSVLTVLHQDWLNGK
EYKCKVSNKALPAPEEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPGK;
and the sequence of light chain constant domain is (SEQ ID NO: 93)
TVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKS
FNRGEC.

In a further preferred embodiment of the present invention there is provided an antibody comprising the V$_H$ of the first aspect and the V$_L$ of the second aspect or the V$_H$ of the third aspect and the V$_L$ of the fourth aspect.

The binding domains and antibodies of the present invention specifically bind cancer cells which express the antigen bound by SC104, in particular colorectal cancer and non-colorectal cancers such as ovary, pancreas, prostate and lung cancer. Accordingly in another aspect the present invention provides a method of treating cancer in a subject wherein the cancer is selected from colorectal, ovarian, pancreatic, prostate and lung, the method comprising administering to the subject a therapeutically effective amount of the binding domain or antibody according to the present invention.

The present invention also provides a method of detecting the presence of cancer cells in a sample, the method comprising contacting the cell sample with a binding domain or antibody according to the present invention and detecting binding of the binding domain or antibody according to the present invention to the cells.

As will be appreciated the sequences developed and described in the present invention may be modified using methods well known in the art to increase binding, by for example, affinity maturation, or to decrease immunogenicity by removing predicted MHC class II-binding motifs. The therapeutic utility of the sequences developed and described herein can be further enhanced by modulating their functional characteristics, such as antibody-dependent cell-mediated cytotoxicity (ADCC), complement-dependent cytotoxicity (CDC), serum half-life, biodistribution and binding to Fc receptors or the combination of any of these. This modulation can be achieved by protein-engineering, glyco-engineering or chemical methods. Depending on the therapeutic application required, it could be advantageous to either increase or decrease any of these activities.

Numerous methods for affinity maturation of antibodies are known in the art. Many of these are based on the general strategy of generating panels or libraries of variant proteins by mutagenesis followed by selection and/or screening for improved affinity. Mutagenesis is often performed at the DNA level, for example by error prone PCR (Thie, Voedisch et al. 2009), by gene shuffling (Kolkman and Stemmer 2001), by use of mutagenic chemicals or irradiation, by use of 'mutator' strains with error prone replication machinery (Greener 1996) or by somatic hypermutation approaches that harness natural affinity maturation machinery (Peled, Kuang et al. 2008). Mutagenesis can also be performed at the RNA level, for example by use of Qβ replicase (Kopsidas, Roberts et al. 2006). Library-based methods allowing screening for improved variant proteins can be based on various display technologies such as phage, yeast, ribosome, bacterial or mammalian cells, and are well known in the art (Benhar 2007). Affinity maturation can be achieved by more directed/predictive methods for example by site-directed mutagenesis or gene synthesis guided by findings from 3D protein modeling (see for example Queen, Schneider et al. 1989 or U.S. Pat. No. 6,180,370 or U.S. Pat. No. 5,225,539).

Methods of increasing ADCC have been described by Ferrara, Brunker et al. 2006; Li, Sethuraman et al. 2006; Stavenhagen, Gorlatov et al. 2007; Shields, Namenuk et al. 2001; Shinkawa, Nakamura et al. 2003; and WO 2008/006554. In a preferred form the antibodies of the present invention have a decreased level of fucose.

Methods of increasing CDC have been described by Idusogie, Wong et al. 2001; Dall'Acqua, Cook et al. 2006; Michaelsen, Aase et al. 1990; Brekke, Bremnes et al. 1993; Tan, Shopes et al. 1990; Norderhaug, Brekke et al. 1991.

References describing methods of increasing ADCC and CDC include Natsume, In et al. 2008. The disclosure of each of these references is included herein by cross reference.

A number of methods for modulating antibody serum half-life and biodistribution are based on modifying the interaction between antibody and the neonatal Fc receptor (FcRn), a receptor with a key role in protecting IgG from catabolism, and maintaining high serum antibody concentration. Dall'Acqua et al describe substitutions in the Fc region of IgG1 that enhance binding affinity to FcRn, thereby increasing serum half-life (Dall'Acqua, Woods et al. 2002) and further demonstrate enhanced bioavailability and modulation of ADCC activity with triple substitution of M252Y/S254T/T256E (Dall'Acqua, Kiener et al. 2006). See also U.S. Pat. Nos. 6,277,375; 6,821,505; and 7,083,784. Hinton et al have described constant domain amino acid substitutions at positions 250 and 428 that confer increased in vivo half-life (Hinton, Johlfs et al. 2004). (Hinton, Xiong et al. 2006). See also U.S. Pat. No. 7,217,797. Petkova et al have described constant domain amino acid substitutions at positions 307, 380 and 434 that confer increased in vivo half-life (Petkova, Akilesh et al. 2006). See also Shields et al (Shields, Namenuk et al. 2001) and WO 2000/42072. Other examples of constant domain amino acid substitutions which modulate binding to Fc receptors and subsequent function mediated by these receptors, including FcRn binding and serum half-life, are described in U.S Pat. Application Nos 20090142340; 20090068175; and 20090092599.

The glycans linked to antibody molecules are known to influence interactions of antibody with Fc receptors and glycan receptors and thereby influence antibody activity, including serum half-life (Kaneko, Nimmerjahn et al. 2006; Jones, Papac et al. 2007; and Kanda, Yamada et al. 2007). Hence, certain glycoforms that modulate desired antibody activities can confer therapeutic advantage. Methods for generating engineered glycoforms are known in the art and include but are not limited to those described in U.S. Pat. Nos. 6,602,684; 7,326,681; 7,388,081; and WO 2008/006554.

Extension of half-life by addition of polyethylene glycol (PEG) has been widely used to extend the serum half-life of proteins, as reviewed, for example, by Fishburn (Fishburn 2008).

As will be recognised it is possible to make conservative amino acid substitutions within the sequences of the current invention. By "conservative substitution" is meant amino acids having similar properties. As used in this specification the following groups of amino acids are to be seen to be conservative substitutions:

H, R and K;
D, E, N and Q;
V, I and L;
C and M;
S, T, P, A and G; and
F, Y and W.

As will be seen the current specification uses the terms "% similar" and "% identical" to describe a number of sequences. As would be understood the term "% identical" means that in a comparison of two sequences over the specified region the two sequences have the specified number of identical residues in the same position. The term "% similar" has a similar meaning but in addition to the number of identical amino acids between the two sequences regard is also had to where the amino acids are not identical but are conservative substitutions as defined above.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

In order that the nature of the present invention may be better understood preferred forms thereof will now be described by reference to the following Examples.

Example 1

Generation of Chimeric SC104 Antibody

The murine SC104 heavy chain variable region ($V_H$), SEQ ID NO:1, was formatted in silico onto a human IgG1 backbone (human IgG1 heavy chain CH1, hinge, CH2 & CH3 domains such as NCBI accession number AAH72419 and derivatives thereof) to yield the chimeric SC104 heavy chain, SEQ ID NO:2. Similarly, the SC104 light chain variable region ($V_L$), SEQ ID NO:3, was formatted in silico onto a human IgG1 backbone (such as NCBI accession number P01834 and derivatives thereof) to form the corresponding chimeric SC104 light chain, SEQ ID NO:4.

Formatting and Production of DNA Constructs

The resulting heavy- and light chain amino acid sequences were back-translated into DNA sequences. The 5'-$V_H$-specific restriction site AscI was included upstream in the nucleotide sequence encoding the heavy chain polypeptide signal sequence, SEQ ID NO:5. A Tth111I restriction site was introduced into the polynucleotide sequence encoding the 3'-$V_H$ region amino acids TVSS. The 5'-$V_L$-specific restriction site BsiWI was incorporated upstream of the nucleotide sequence encoding the light chain polypeptide signal sequence, SEQ ID NO:6. An RsrII restriction site was included at the 3'-end of the nucleic acid sequence encoding the amino acids RT located at the C-terminal end of the $V_L$ region. These sequences were then optimised for expression in CHO cells using GeneOptimizer® technology (GeneArt, Germany).

The variable regions were subsequently synthesised de novo by assembly of synthetic oligonucleotides (GeneArt, Germany). The added restriction sites were used to clone the variable regions into the Glutamine Synthetase (GS) Chinese Hamster Ovary (CHO)-based gene expression system vectors (Lonza, UK) containing the appropriate IgG 1 constant regions. The resulting heavy chain-containing and light-chain-containing vectors were used to co-transfect CHO-K1SV cells to produce antibodies.

Cell Culture and Transient Expression of Antibody Constructs

CHO-K1SV (Lonza, UK) cells were cultured at $2\times10^5$ cells/ml-$4\times10^6$ cells/ml in Freestyle™ CHO chemically defined cell growth media (Invitrogen™) and cultures supplemented with 6 mM final concentration of L-glutamine (Invitrogen™). Cells were cultured at 36.5° C., 10% $CO_2$ and 140 rpm. On the day before transfection, 100 ml culture volumes were seeded at $5\times10^5$ cells/ml in 500 ml vented Erlenmeyer flasks (Corning®). The next day 4 mL of OptiPRO™ SFM (Invitrogen™) was prepared in a 15 mL Corning@ tube and mixed with 100 µg of each antibody chain. The resulting mixture was filtered through a 0.2 µm 13 mm syringe-end filter unit (Millipore®) into a fresh 15 mL Corning® tube containing 200 µl of Freestyle™ Max reagent (Invitrogen™). This mixture was incubated for 10 minutes at room temperature prior to addition to the CHO-K1SV cells seeded previously. After 7 days the supernatant was harvested by centrifugation at 3000 g for 10 mins prior to filtration through a 0.2 µm membrane into a sterile receptacle (Corning® filter unit).

Purification of Antibodies

Supernatants harvested from transfected CHO cells were adjusted to pH 7.4 before being loaded onto a HiTrap™ Protein A column (1 mL, GE® Healthcare). The column was washed with 30 mL of 1×PBS (pH 7.4). Elution was performed using 0.1M citric acid pH 3. The eluted antibody was desalted using Zeba™ desalting columns (Pierce®) into 1×PBS (pH 7.4). Antibody concentration was determined by $A_{280}$ value.

Flow Cytometry-Based Binding Assays

Viable tumour cells and control cells ($2\times10^5$, as judged by trypan blue exclusion) were incubated in triplicate with mouse SC104, chimeric SC104 or humanised variants, and human $IgG_1$ isotype (Sigma-Aldrich®) at various concentrations in 100 µl of buffer (PBS plus 1% FCS) in 96 V-well plates (Eppendorf) for 20 min on ice in the dark. Cells were washed twice with buffer before incubation for 20 min in 100 µl of buffer containing goat anti-human IgG (Fc-specific, Sigma-Aldrich®, conjugated to FITC) or goat anti-mouse IgG (Fc-specific, Sigma-Aldrich®, conjugated to FITC) for detecting chimeric or mouse antibodies, respectively. After washing cells were resuspended in buffer and analysed for antibody binding by flow cytometry on a Cell Lab Quanta™ SC MPL (Beckman Coulter) using EV, side scatter and FL-1 gating; during acquisition the cells in the 96-well plate were cooled by underlying a cool pack (Eppendorf). Results were expressed as mean fluorescent intensity (MFI); curve slope values were calculated using non-linear regression analysis by GraphPad Prism® software.

Flow Cytometry-Based Direct Killing Assays

Viable tumour cells ($2\times10^5$, as judged by trypan blue exclusion) were incubated in triplicate with mouse SC104, chimeric SC104 or humanised variants, and human $IgG_1$ isotype (Sigma-Aldrich®) at various concentrations in 80 µl of buffer (PBS plus 1% FCS) in 96 V-well plates (Eppendorf) for 2.5 to 3 hours at room temperature in the dark. To each well was added 0.15 g of 7AAD (BD® Biosciences) in 20 µl of buffer, and cells were incubated for further 20 min before cell viability was assayed by flow cytometry on a Cell Lab Quanta™ SC MPL (Beckman Coulter) using EV, side scatter and FL-3 gating; during acquisition the cells in the 96-well plate were cooled by underlying a cool pack (Eppendorf). Results were expressed as percentage of 7AAD$^+$ cells; curve slope values were calculated using non-linear regression analysis by GraphPad Prism® software

Figure 1:
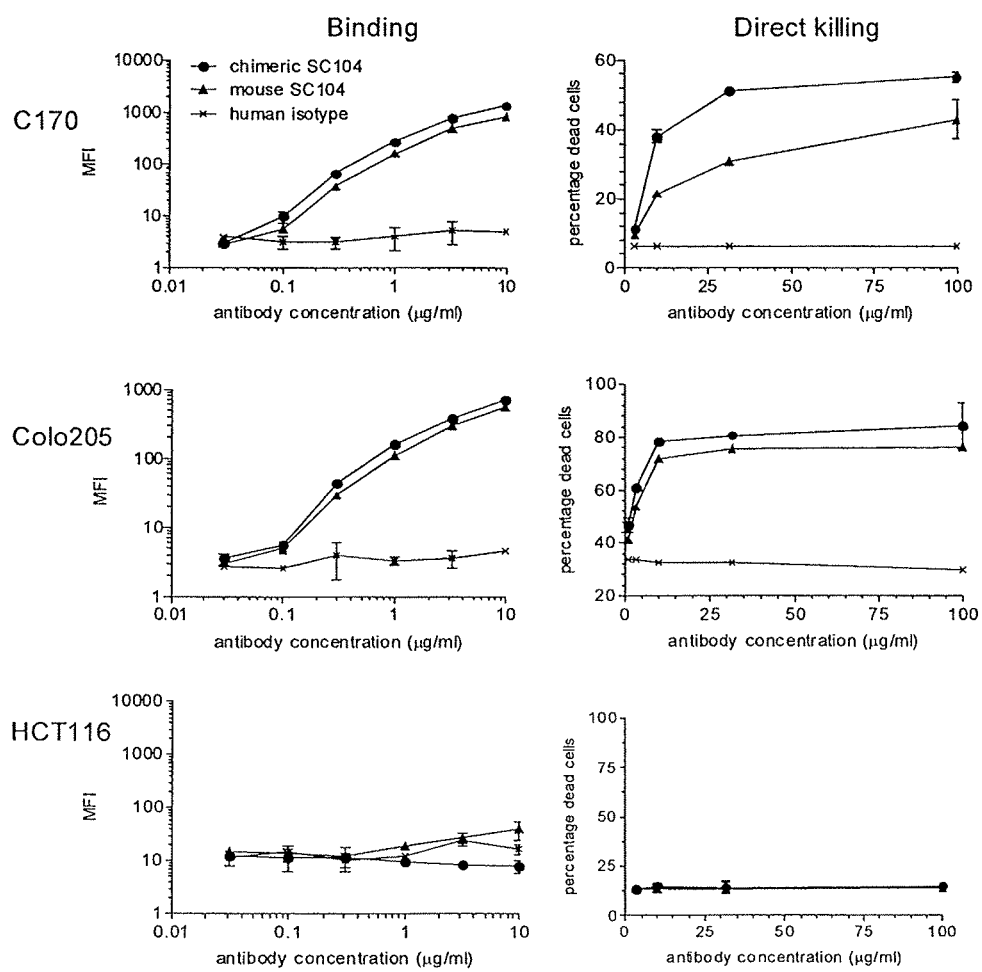
FIG. 1—Binding (left hand panels) and direct killing (right hand panels) activities of mouse SC104 (variable regions listed in SEQ ID NO:3/SEQ ID NO:1) and chimeric SC 104 (SEQ ID NO:4/SEQ ID NO:2) antibodies and the human IgG1 isotype control to SC104 antigen positive (C170, Colo205) and SC104 antigen negative (HCT-116) human colon cancer cell lines as shown by flow cytometry; sequence IDs refer to the sequence listing. Chimeric SC104 and murine SC104 antibodies exhibit comparable selective binding to- and direct killing activity of antigen positive human colon cancer cell lines. Both antibodies do not bind to- and directly kill antigen negative human colon cancer cell lines. Each point represents mean±SD of three replicate samples.

Chimeric SC104 Antibody has Potent and Specific Binding to and Direct Killing Activity of Human Colon Tumour Cells The chimeric and mouse parental SC104 antibodies were tested for binding to human colon cancer cell lines C170 (ECACC accession number 97071507) and Colo205 (ATCC accession number CCL-222); the mouse SC104 antibody was previously shown to bind strongly to these cell lines using flow cytometry assays (Durrant, Harding et al. 2006). FIG. 1 (left hand panels) shows binding of the SC 104 antibodies, but not of the human $IgG_1$ isotype control, to C170 and Colo205, with both the mouse and chimeric SC104 antibody displaying similar binding strength over a range of antibody concentrations. In contrast none of the antibodies bound to the human colon cancer line HCT-116 (ATCC accession number CCL-247) which was thus defined as SC104 antigen negative.

The mouse SC 104 antibody is known to induce direct killing of colon tumour cells without the need for immune effector cells or complement (Durrant, Harding et al. 2006). Indeed both the mouse and chimeric SC104 antibodies, but not the human $IgG_1$ isotype control, showed potent direct killing of the antigen positive cells C170 and Colo205; in contrast, the antibodies did not show above background killing of the antigen negative cells HCT-116 (FIG. 1, right hand panels).

Other experiments with different antigen negative human colorectal tumour cells (HCT15, ATCC accession number CCL-225), human non-tumour cells (MRCS, ATCC accession number CCL-171) or peripheral blood mononuclear cells from normal human donors displayed no binding and no direct killing activities for mouse and/or chimeric SC104 antibodies (data not shown). Taken together the chimeric SC104 antibody had similar potency and specificity when compared with parental mouse SC104 antibody. Hence chimeric SC104 antibody was used as a reference to test the activity of subsequently generated humanised SC104 antibody variants.

Example 2

Humanisation of SC104

Selection of Suitable Human Framework Acceptors by 3D Modelling

Independent 3D models of the murine SC104 heavy chain variable region ($V_H$) and light chain variable region ($V_L$) were constructed using the database of crystal structures (see for example the Research Collaboratory for Structural Bioinformatics (RCSB) protein data bank, http://www.rcsb.org/pdb/home/home.do; part of the Worldwide Protein Data Bank, http://www.wwpdb.org) and software package Discovery Studio v1.7 (Accelrys®, USA). Briefly, the protein data bank database was interrogated by Basic Local Alignment Search Tool (BLAST) searches using either the murine SC104 heavy chain variable region or light chain variable region to identify antibodies of similar polypeptide sequence with accompanying crystal structure information. These structures were subsequently used to build homology models based on the amino acid sequence homology shared by the murine SC104 variable regions and that of the identified crystal structures. Using these murine $V_H$ and $V_L$ models, suitable human $V_H$ and $V_L$ acceptor frameworks were independently identified from the protein data bank that shared framework structural homology with those of the murine antibody. To ensure correct heavy- and light-chain pairing $V_H$ and $V_L$ human acceptor frameworks of same antibody crystal structure were progressed through the humanisation process. Human acceptor antibodies with better murine-human heavy chain framework region structural homology were preferred over those with better murine-human light chain framework homology. These include pdb accession codes 1U6A and 1QLR. Human framework acceptors were assessed to test whether these structures are capable of supporting the SC104 CDRs appropriately.

Formatting of Humanised Antibody Constructs

Initially, the murine SC104 complementarity determining regions (CDRs) were defined according to the method of Kabat (see (Kabat 1991) given that CDR grafting technologies (see for example (Queen, Schneider et al. 1989) or U.S. Pat. No. 6,180,370 or U.S. Pat. No. 5,225,539) are based on this categorisation. In later humanisation attempts, the CDR1 of the heavy chain (CDR-H1) was defined using the AbM nomenclature (see for example (Dübel 2007) and references incorporated therein), Table 1. The CDRs were formatted in silico onto the selected human frameworks using the DNAStar® software package (version 8; Lasergene®, USA). $V_H$ regions were formatted onto a human IgG1 heavy chain containing CH1, hinge, CH2 & CH3 domains (such as NCBI accession number AAH72419 and derivatives thereof). Concomitantly, $V_L$ regions were formatted using the corresponding human IgG1 light chain constant region (such as NCBI accession number P01834 and derivatives thereof).

Figure 2:
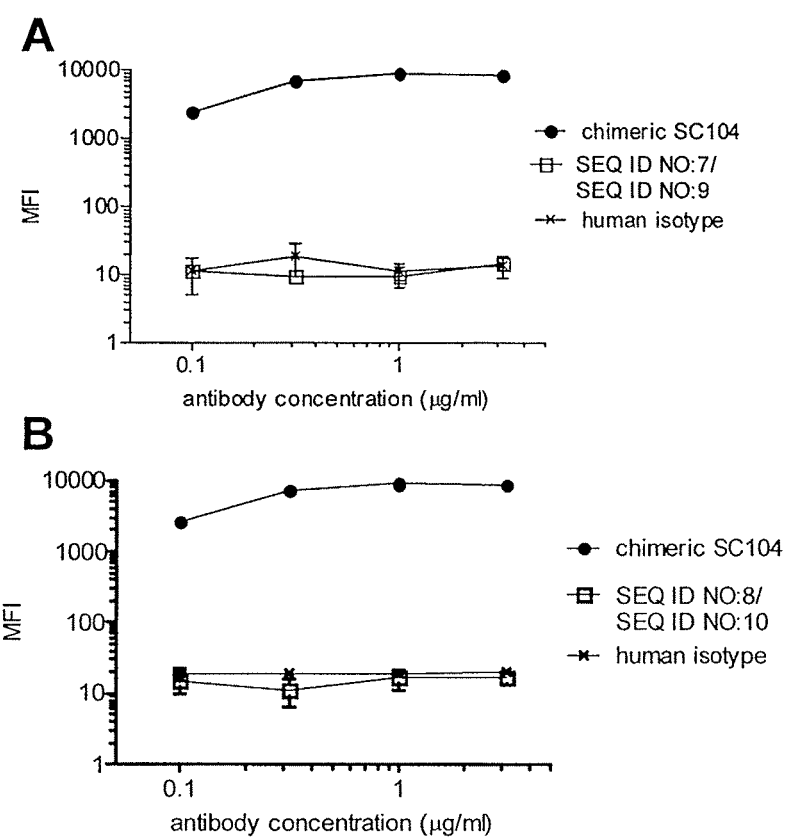
FIG. 2—Humanisation of SC104 on human acceptor framework 1U6A or 1QLR incorporating a Kabat-defined CDR-H1 (-□-) yields non functional antibody variants that do not bind to the SC104 antigen positive human colon cancer cell line C170. The binding activities of humanised SC104 variants using a Kabat-defined CDR-H1 grafted either to the human acceptor 1U6A (SEQ ID NO:7/SEQ ID NO:9, panel A) or 1QLR (SEQ ID NO:8/SEQ ID NO:10, panel B); were assessed by flow cytometry using the antigen positive cell line C170. The chimeric SC104 antibody (SEQ ID NO:4/SEQ ID NO:2) is shown as a comparator along with a human IgG$_1$ isotype negative control. Each point represents mean±SD of three replicate samples.

Humanised SC104 Variants Incorporating a Kabat-Defined CDR-H1 Unexpectedly Yield Non Functional Antibody Human acceptor frameworks 1U6A and 1QLR were used for SC104 humanisation. The murine SC 104 light chain CDRs were formatted onto the 1U6A and 1 QLR light chain framework regions. An uncommon alanine residue at position 15 in the 1U6A framework sequence was removed by substitution with proline (A15P), yielding SEQ ID NO:7. The 1QLR-based humanised SC104 light chain was formatted as described above to yield SEQ ID NO:8. The corresponding 1U6A-based SC104 heavy chains were formatted containing a Kabat-defined CDR-H1, SEQ ID NO:9. Concomitantly the 1QLR-based SC104 heavy chains were formatted containing a Kabat-defined CDR-H1, SEQ ID NO:10. 1U6A-based light- and heavy-chain combinations SEQ ID NO:7 and SEQ ID NO:9 were co-expressed in CHO cells. 1QLR-based light- and heavy-chain combinations SEQ ID NO:8 and SEQ ID NO:10 were also co-expressed in CHO cells. The resulting antibodies were purified by protein A affinity chromatography and tested for live-cell binding activity using flow cytometry. Surprisingly, these humanised antibody variants, both incorporating a Kabat-defined CDR-H1, failed to bind to SC104 antigen positive cells (FIG. 2).

Humanised SC104 Variants Incorporating an AbM-Defined CDR-H1 Surprisingly Yield Functional Antibody Following the unexpected failure upon humanisation incorporating a Kabat-defined CDR-H1, the AbM-defined CDR-H1 nomenclature was applied (Table 1). Subsequently, 1U6A- and 1QLR-based SC104 heavy chains were formatted to incorporate and AbM-defined CDR-H1, SEQ ID NOs:11 and 12 respectively. 1U6A-based light- and heavy-chain combinations SEQ ID NO:7 and SEQ ID NO:11 were co-expressed in CHO cells. 1QLR-based light- and heavy-chain combinations SEQ ID NO:8 and SEQ ID NO:12 were also co-expressed in CHO cells. The resulting antibodies were purified by protein A affinity chromatography and tested for live-cell binding activity using flow cytometry. Surprisingly, these humanised antibody variants, both incorporating an AbM-defined CDR-H1, bound to SC104 antigen positive cells (FIG. 3).

Increasing the Binding Activity of Humanised SC104

Figure 3:
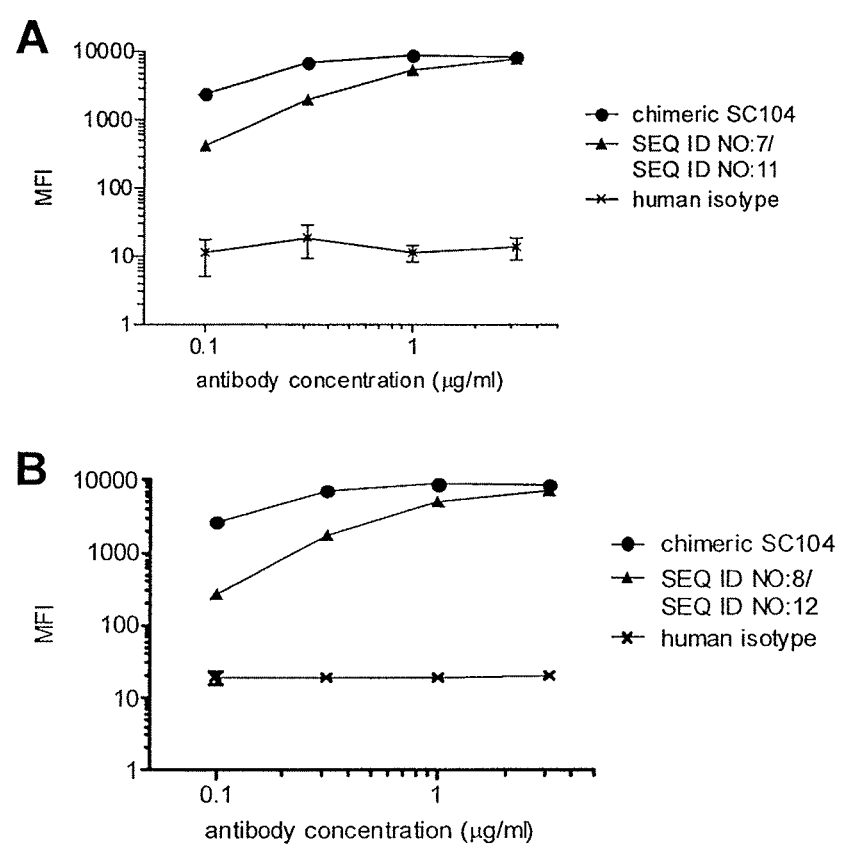
FIG. 3—Humanisation of SC104 on human acceptor framework 1U6A or 1QLR incorporating an AbM-defined CDR-H1 (-▲-) generates antibody variants that bind to the SC104 antigen positive human colon cancer cell line C170. The binding activities of humanised SC104 variants incorporating an AbM-defined CDR-H1 grafted either to the human acceptor 1U6A (SEQ ID NO:7/SEQ ID NO:11, panel A) or 1QLR (SEQ ID NO:8/SEQ ID NO:12, panel B); were assessed by flow cytometry using the antigen-positive cell line C170. The chimeric SC104 antibody (SEQ ID NO:4/ SEQ ID NO:2) is shown as a comparator along with a human IgG$_1$ isotype negative control. Each point represents mean±SD of three replicate samples.

FIG. 3 indicates that the humanised SC104 antibodies had suboptimal binding activity compared to that observed with the chimeric SC104. These data imply that one or more framework amino acid substitutions are important in order to humanise SC104 with little resultant loss in binding activity. To address this issue, the framework polypeptide sequences of murine SC104 and 1U6A were compared. Amino acid differences between the frameworks were flagged and scrutinized in silico using murine SC104 variable region 3D models. Six $V_H$ and three $V_L$ amino acids (including the substitution A15P to remove an uncommon alanine residue in this position found in the 1U6A acceptor framework) were identified for further in vitro investigation to test their contributions to the binding activity of the humanised antibodies. A similar analysis was performed using 1QLR-humanised SC104 whereby four $V_H$ and two $V_L$ amino acids were flagged for testing in vitro. All of the positions flagged for in vitro investigation in 1QLR-humanised SC 104 were identical to those already identified in 1U6A humanised SC104. Subsequently attempts were focussed on identifying the residue(s) critical in enhancing the potency of humanised SC104 using only the 1U6A acceptor.

Predicted Substitution(s) Required in the Humanised $V_H$ Frameworks are More Important for Enhancing Binding Activity than Those Predicted in the Humanised $V_L$ The genes encoding both AbM- and Kabat-defined CDR-H1 variants of the 1U6A-based SC104 heavy chains were resynthesised to incorporate a total of six amino acid residue substitutions—Q46E, 148M, V67I, T68S, V71R, E72D (Kabat numbering). This yielded SEQ ID NOs: 13 (AbM CDR-H1) and 15 (Kabat CDR-H1) respectively. An additional two amino acid substitutions—Q1E and S25T-flagged as lower priority than the aforementioned six by the processes outlined above where also introduced into SEQ ID NO:13 to yield SEQ ID NO:14, an AbM-defined CDR-H1 variant containing a total of eight amino acid substitutions. The corresponding AbM- and Kabat-grafted heavy chain sequences—SEQ ID NOs:11 and 9 respectively were used as non-substituted controls.

Figure 4:
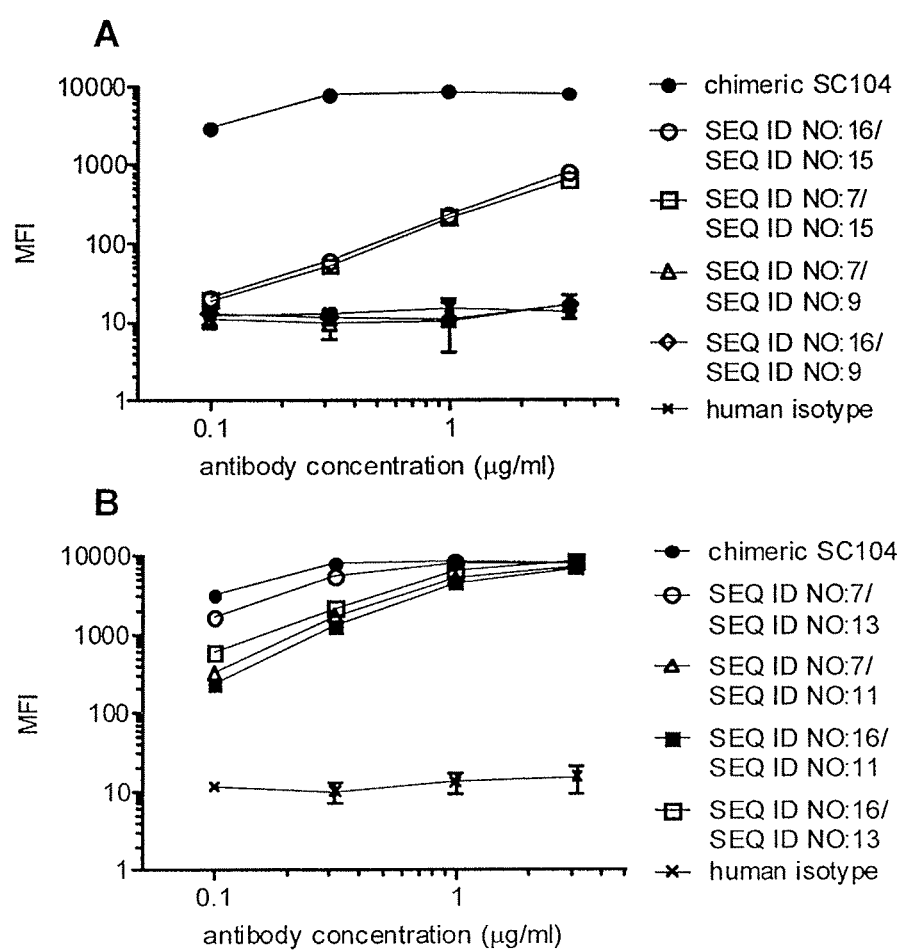
FIG. 4—Analysis of light chain and heavy chain amino acid substitution(s) towards enhancing the binding activity of 1U6A humanised SC104. The influence of the substitutions in each chain was analysed by binding activity assays to the antigen positive cell line C170 by flow cytometry. The chimeric SC104 antibody (SEQ ID NO:4/SEQ ID NO:2) is shown as a comparator along with a human IgG$_1$ isotype negative control. Each point represents mean±SD of three replicate samples.

The 1U6A-based light chain was formatted incorporating three substitutions—I2N, A15P, T69N (Kabat numbering)—to create SEQ ID NO:16. The corresponding light chain sequence SEQ ID NO:7 was used as a minimally substituted control. Substituted and non- or minimally substituted combinations of heavy- and light chains were co-expressed and their activity in flow cytometry based cell binding assays assessed. In grafts containing a Kabat-defined CDR-H1, both humanised SC 104 antibody variants SEQ ID NO:7/SEQ ID NO:15 and SEQ ID NO:16/SEQ ID NO:15 shared the same heavy chain (SEQ ID NO:15) incorporating the aforementioned six amino acid substitutions. These antibodies displayed similar positive binding activity irrespective of whether paired with either the substitution-containing (SEQ ID NO:16) or minimally-substituted (SEQ ID NO:7) light chains. In contrast, changing the heavy chain to one containing a Kabat-defined CDR-H1 and no amino acid substitutions, such as SEQ ID NO:9, abolished binding irrespective of whether light chain SEQ ID NO:7 or SEQ ID NO:16 was used, FIG. 4A. Similarly, light chains containing either a single or all three substitutions (SEQ ID NOs:7 and 16 respectively) did not markedly affect the potent binding activity of humanised SC104 antibody variants when paired with a heavy chain comprising an AbM-defined CDR-H1 (see for example SEQ ID Nos: 11 and 13 representing unsubstituted and substitution-containing heavy chains respectively), FIG. 4B. A similar trend to that of FIG. 4B was observed when heavy chain SEQ ID NO:13 was switched for heavy chain SEQ ID NO:14 and an identical flow cytometry-based binding assay with chimeric SC 104 (SEQ ID NO:4/SEQ ID NO:2) was performed, results not shown. This data indicated substitutions Q1E and S25T were not responsible for the potent binding activity shown by heavy chain SEQ ID NOs: 13 and 14 compared with their unsubstituted counterpart, SEQ ID NO:11. Consequently substitutions Q1E and S25T were not investigated further. Moreover, these data demonstrate the importance of one or more substitutions in the 1U6A heavy chain to generate a humanised SC104 variant with enhanced binding activity.

Substitutions in the heavy chain of 1U6A-humanised SC104 were introduced into the Kabat-grafted 1QLR heavy chain sequence (SEQ ID NO:10) at positions—I48M, V67I, T68S and V71R—yielding SEQ ID NO:17. Similarly, substitutions were made in the 1QLR-humanised SC104 light chain—I2N and T69N—to give SEQ ID NO:18. The activity of antibodies containing an AbM-defined CDR-H1 (SEQ ID NO:12) was not significantly affected when expressed with either an unsubstituted (SEQ ID NO:8) or substitution-containing (SEQ ID NO:18) light chain. Expressing the 1QLR-SC104 variant with a Kabat-defined CDR-H1 containing the aforementioned substitutions (SEQ ID NO:17) with the non-substituted 1QLR partner SEQ ID NO:8 yielded a humanised variant with low binding activity. The negligible binding activity observed with the antibody produced upon co-expression of SEQ ID NO:17 with the fully substituted light chain SEQ ID NO:18 is suggestive that the substitutions in the light chain are deleterious to the binding activity of 1QLR-humanised SC104. The binding data of these antibody variants in addition to those described previously is summarised in Table 2.

Presence of R71 in the $V_H$ Framework is Important to Yield Highly Active Humanised SC104

Individual 1U6A heavy chain variable region framework substitutions Q46E, 148M, V67I, T68S, V71R and E72D were formatted along with Q1E into SEQ ID NO:11, to yield SEQ ID NOs:19 through 24. The resulting heavy chains were co-expressed with light chain SEQ ID NO:7, and the resulting humanised SC104 variants compared by flow cytometry-based binding assays. The humanised SC104 antibody variants with Q46E, 148M, V67I, T68S and E72D displayed similar binding activity to each other but markedly lower activity when compared with chimeric SC 104 antibody, FIG. 5. In contrast the humanised SC104 antibody variant carrying the V71R substitution (encoded by SEQ ID NO:23) showed enhanced binding activity similar to the chimeric SC104 antibody. These data indicate that R71 in addition to an AbM-defined CDR-H1 is important for highly potent humanised forms of SC104. Reformatting the R71-containing heavy chain to incorporate the substitution E1Q, SEQ ID NO:25, did not alter the high levels of binding activity of the resulting antibody upon co-expression with light chain SEQ ID NO:7 (not shown).

R71 Enhances the Binding Activity of SC104 Humanised Variants Comprising both AbM- and Kabat-defined CDR-H1

Substitution V71R, identified as critical for the potent binding activity of SC104 humanised using the human acceptor 1U6A, was introduced into 1QLR-based SC104 variants containing either an AbM- or Kabat-defined CDR-H1 as detailed in SEQ ID Nos:26 and 27 respectively. For comparison, V71R was also introduced into the 1U6A-based SC104 variant SEQ ID NO:10 which comprises a Kabat-defined CDR-H1 to form SEQ ID NO:28. 1QLR-based light and heavy chain combinations SEQ ID NO:8 and SEQ ID NO:26 or SEQ ID NO:27 were co-expressed in CHO cells. 1U6A-based light and heavy chain combination SEQ ID NO:7 and SEQ ID NO:28 was also co-expressed in CHO cells. The resulting antibodies were purified by protein A affinity chromatography and tested for live-cell binding activity to the antigen-positive cell line C170 by flow cytometry. The substitution V71R significantly enhances the live-cell binding activity to the antigen-positive cell line C170 of 1QLR-based SC104 containing an AbM-defined CDR-H1, and to a lesser extent the corresponding Kabat-defined grafted antibody as measured by flow cytometry, FIG. 6A. In comparison, the substitution V71R significantly enhances the live-cell binding activity of both Kabat- and AbM-defined CDR-H11U6A-based SC 104 variants to the antigen-positive cell line C170 as measured by flow cytometry, FIG. 6B.

Identification of Amino Acid Substitutions that Enhance Binding Activity of Humanised SC104 Variants in the Region where AbM- and Kabat Definitions of CDR-H1 Differ An AbM-defined heavy chain CDR1 includes an additional five donor amino acid residues at the amino-terminal end of the CDR compared with its Kabat-grafted counterpart, Table 1. The consistent, enhanced potency of SC104 variants containing an AbM-defined CDR-H1 relative to their Kabat-grafted counterparts is surprising. Table 3 compares these five amino acids from donor (included in AbM CDR-H1 grafts), 1U6A and 1QLR acceptor sequences. Comparing the donor and 1U6A sequences, it appears that the non-conservative difference G27Y is most likely responsible for enhancing the potency of humanised variants containing an AbM-defined CDR-H1 relative to the chimera, since T30S is a conservative change. This substitution, G27Y, was incorporated into the Kabat grafted 1QLR-SC104 variant SEQ ID NO:27 (+R) to yield SEQ ID NO:29 (+R+Y). This heavy chain along with the 1QLR-based light chain SEQ ID NO:8 was co-expressed in CHO cells and the resulting antibody purified as described previously. For comparison, a 1QLR-humanised antibody incorporating a Kabat-defined CDR-H1 without R71 (SEQ ID NO:10) and a second variant incorporating an AbM-defined CDR-H1 with R71 (SEQ ID NO:26) were included in comparative live-cell binding activity to the antigen-positive cell line C170 by flow cytometry, FIG. 7. Unexpectedly, the resultant humanised antibody variant produced by light- and heavy chain combination SEQ ID NO:8 and SEQ ID NO:29 had no binding activity.

Example 3

SC104 Variants with Lower Predicted Immunogenicity

Murine SC104 variable region amino acid sequences were screened in silico for predicted T cell epitopes (Epibase®, Algonomics, Belgium). Two predicted major histocompatibility complex class II (MHC class II) binding peptides were identified. These are located in the heavy chain at the framework (FR) 2:CDR-H2 and CDR-H2:FR3 boundaries. These were of particular interest, since predictions for their removal involved substituting CDR amino acid residues which may alter antibody binding potency.

Heavy Chain $V_H$ Region Predicted MHC Class II-Binding Peptide Removal

Predictions suggested that the strength of the FR2:CDR-H2 MHC class II binding peptide in the murine $V_H$ region would be reduced on substituting the phenylalanine residue at position 4 of the CDR-H2 sequence HIHFSGRPTYNPSLSS with tryptophan (SEQ ID NO:30), or tyrosine (SEQ ID NO:31), or preferentially proline (SEQ ID NO:32). These heavy chains were co-expressed in CHO cells with light chain SEQ ID NO:4 and the resulting antibodies purified by protein A chromatography as described previously. Surprisingly, comparative flow cytometry-based binding assays with chimeric SC104 revealed that the substitutions F53W and F53Y had negligible effect on the potent binding activity observed by chimeric SC104, whilst the substitution F53P drastically reduced the binding potency of the resulting antibody, FIG. 8.

Further in silico immunogenicity predictions (predicted by the software ProPred, Singh, H. and Raghava, G. P. S. (2001) ProPred: Prediction of HLA-DR binding sites. Bioinformatics, 17(12), 1236-37. http://www.imtech.res.in/raghava/propred/) and/or SYFPETHI (Rammensee, Bachmann et al. 1999); http://www.syfpeithi.de/Scripts/MHCServer.dll/EpitopePrediction.htm) suggested that the strength of this predicted MHC class II binding peptide was diminished upon grafting of the SC 104 CDR-H2 into the human acceptor backbone 1U6A or 1 QLR.

The presence of the second predicted MHC class II binding peptide at the CDR-H2:FR3 boundary was predicted to be present in both the murine and humanised SC104 antibody sequences.

SC104 Variants with Lower Predicted Immunogenicity

Based on the acceptor frameworks of 1U6A- and 1QLR-based SC104 novel humanised variants were generated for which potential major histocompatibility complex class II binding sequences were removed. Briefly, the humanised light chain variable regions were only predicted to have tolerated (ie: germline) MHC class II binding sequences, whereas the heavy chain variable regions of 1QLR and 1U6A were predicted to posses one and two strong-binding major histocompatibility complex class II binding sequences respectively. A further weaker-binding putative MHC class II-binding sequence was also predicted immediately prior to CDR-H1 as defined by method of Kabat. A substitution strategy was developed with the aim removing these predicted MHC class II binding epitopes. A panel of 1QLR-based SC104 heavy chain variable region variants with predicted lower immunogenicity as listed in SEQ ID NO:33 through SEQ ID NO:38 was constructed. A panel of 1U6A-based SC104 heavy chain variable region variants with predicted lower immunogenicity as detailed in SEQ ID Nos:39 through 50 was also constructed. Co-expression of 1QLR-based light chain SEQ ID NO:8 with each one of the variants SEQ ID NO:33 through SEQ ID NO:38 in CHO cells was performed and the resulting antibodies purified as detailed previously. Similarly, co-expression of 1U6A-based light chain SEQ ID NO:7 with each one of the variants SEQ ID NO:39 through SEQ ID NO:50 in CHO cells was performed and the resulting antibodies purified as detailed previously.

Humanised SC104 antibody variants with lower predicted immunogenicity were compared for binding activity to human colon cancer cells that express the SC104 antigen (C170, Colo205) with chimeric SC104 in live-cell flow cytometry assays. Binding activity comparable to that of the chimeric antibody was observed in each case. The SC104 antibody binding was also cell type specific, as the lower predicted immunogenicity SC104 variants did not bind the SC104 antigen negative human colon cancer cells HCT116; examples for the potent and specific binding of lower predicted immunogenicity SC104 variants are shown in FIG. 9.

Identification of Critical Residues in the Heavy Chain Variable Region that Confer Optimal Binding Activity to SC104 Variants with Lower Predicted Immunogenicity The sequence $GY_{27}SI_{29}S$ spanning amino acid positions 26 through 30 in the framework region immediately prior to Kabat-defined CDR-H1 conferred high binding activity of SC104 variants with lower predicted immunogenicity when incorporated into acceptor framework 1U6A or 1QLR (FIG. 9). In contrast, the sequence $GY_{27}SF_{29}S$ resulted in surprisingly poor binding activity when incorporated in constructs based on the 1QLR acceptor framework (FIG. 7), indicating Y27 is not the sole residue involved in conferring high binding activity. The effect of different amino acid residues at position 29 on binding activity was subsequently investigated by varying the amino acid residue present at this position of the 1U6A-humanised heavy chain SEQ ID NO:50. Heavy chain variants were co-expressed in CHO cells with light chain SEQ ID NO:7, purified by protein A affinity chromatography and tested by flow cytometry as described previously. Exemplary binding data is shown in FIG. 10, whilst Table 4 summarizes the binding activities of all substitutions tested. Surprisingly, only residues I (SEQ ID NO:50), L (SEQ ID NO:62) or V (SEQ ID NO:70) at position 29 conferred optimal binding activity of humanised SC104 antibody variants with low predicted immunogenicity, whereas the majority of substitutions, including I29F (SEQ ID NO:58), resulted in poor binding activity to SC104 antigen positive human cancer cells C170.

The importance of R71 in framework 3 of variable heavy chain in yielding a humanised variant possessing optimal high binding activity has previously been demonstrated, FIG. 6. To further improve the binding activity of 1U6A-based SC104 variants with lower predicted immunogenicity the residue at position 71 was substituted to generate a panel of heavy chain variants. These variants were subsequently co-expressed in CHO cells with light chain SEQ ID NO:7, purified by protein A affinity chromatography and tested by flow cytometry as described previously. Exemplary binding data is shown in FIG. 11. Table 5 summarizes the binding activities of all substitutions tested. Unexpectedly, only the positively charged residues R and K (SEQ ID NOs: 50 and 81 respectively) at position 71 conferred the highest binding activity of humanised SC104 antibody variants to SC104 antigen positive human colon cancer cell line C170.

Modification of N—X—S Motif in CDR-H2

N-linked glycosylation is known to have implications for protein product heterogeneity and potentially impact on immunogenicity. Analysis of the murine variable regions for potential N-linked glycosylation sites was performed (see for example (Ye 2007) or the software prediction algorithm Net-NGlyc of http://www.cbs.dtu.dk/services/NetNGlyc/ by R. Gupta, E. Jung and S. Brunak). This analysis identified the N—X—S motif, NPS, within the CDR-H2 sequence. Typically, the N—X—S motif is indicative of a putative N-linked glycosylation site, however an exception to this rule is when X is a proline residue, as in this case (see for example (Gavel and von Heijne 1990). Nonetheless, an analysis was performed to see if this N residue in CDR-H2 was permissive of change with respect to retaining binding activity. The NPS sequence in the chimeric SC104 sequence was altered to DPS to yield SEQ ID NO:51. Co-expression of light chain SEQ ID NO:4 with the heavy chain SEQ ID NO:51 in CHO cells and subsequent purification of the resulting product (as described previously) was performed. The resulting antibody was compared in flow cytometry-based binding assays to the SC104 antigen-positive cell line C170. Removal of the N—X—S motif by N→D substitution within CDR-H2 had negligible impact on the binding potency of the resulting antibody upon comparison with chimeric SC104

Example 4

Flow Cytometry-Based Direct Killing Assays

Viable tumour cells ($2 \times 10^5$, as judged by trypan blue exclusion) were assayed with chimeric SC104, humanised SC104 antibody variants or human IgG$_1$ isotype (Sigma-Aldrich®) as described in Example 1. 1U6A-based humanised SC104 antibody variants composed of light- and heavy chain combinations SEQ ID NO:7/SEQ ID NO:25 and SEQ ID NO:7/SEQ ID NO:50 were selected for further studies in addition to 1QLR-based variants combinations of SEQ ID NO:8/SEQ ID NO:26 and SEQ ID NO:8/SEQ ID NO:38.

Novel Humanised SC104 Antibody Variants with Lower Predicted Immunogenicity have Potent Direct Killing Activity Against Human Colon Tumour Cells The humanised SC104 antibody variants with lower predicted immunogenicity showed potent direct killing activity of human colon cancer cells without the need for immune effector cells. FIG. 12 shows an example of direct killing by these humanised SC104 antibody variants, the chimeric SC104 antibody and the human isotype control using C170 tumour cells. When tested similar results were obtained using Co10205 tumour target cells (data not shown). Surprisingly, the 1U6A-derived SC104 antibody variants (SEQ ID NO:7/SEQ ID NO:25 and SEQ ID NO:7/SEQ ID NO:50) showed more potent direct killing activity compared with 1QLR-framework derived SC104 antibody variants (SEQ ID NO:8/SEQ ID NO:28 and SEQ ID NO:8/SEQ ID NO:38). This difference in direct killing activity was unexpected given the similar binding activity of the these SC104 antibody variants (FIG. 9)

Example 5

Antibody-Dependent Cell-Mediated Cytotoxicity (ADCC) Assay

Effector (peripheral blood mononuclear) cells were purified from Buffy Coat preparation of normal human donors (provided by Australian Red Cross Blood Services) using Lymphoprep™ according to the manufacturer's protocol (Axis-Shield PoC AS). Viable effector cells ($5 \times 10^6$/ml) were incubated overnight in RPMI 1640 (Gibco®) plus 10% FCS at 37° C. and 10% $CO_2$. Tumour target cells and effector cells were washed in PBS followed by media (RPMI1640 w/o phenol red, Gibco®, plus 0.5% FCS), resuspended in media and incubated with various concentration of antibody (chimeric SC104, humanised SC104 or human IgG$_1$ isotype, Sigma-Aldrich®, #15154) in triplicate in 96-well U well plates (Corning®) in a 200 µl assay consisting of the following final concentrations: target cells, $1 \times 10^5$ cells/ml; effector cells, $2.5 \times 10^6$ cells/ml; antibody range 10 to 0.001 ug/ml. For controls, target cells only were incubated in the absence (min target) or presence (max target) of 1% Triton®-X (Sigma-Aldrich®), and target and effector cells (background) were incubated in the absence of antibody. Plates were centrifuged for 2 min at 160×g and incubated in humified $CO_2$ atmosphere in 37° C. for 4 hours. Cell death was measured using a Lactate Dehydrogenase release assay. Briefly, plates were spun for 5 min at 250×g and 100 µl of cell supernatant was assayed for Lactate Dehydrogenase release using the Cytotoxicity Detection Kit (Roche) according to the manufacturer's guidelines. To minimise contaminating cell carry-over the supernatant was filtered through a 96-well 0.2 micron AcroPrep™ plate (Pall). LDH release was quantified by reading absorbance at 492 nm and percentage cytotoxicity was calculated using the following formula: 100×[sample−mean (background)]/mean (max target−min target); $EC_{50}$ values were calculated using non-linear regression analysis by GraphPad Prism® software.

Complement-Dependent Cytotoxicity (CDC) Assay

Viable tumour target cells were incubated in media (RPMI1640 w/o phenol red, Gibco®, plus 5% FCS), with human complement serum (Sigma-Aldrich® #S1764) and various concentrations of antibody (chimeric SC104, humanised SC104 or human IgG$_1$ isotype, Sigma-Aldrich®, #15154) in triplicate in 96-well flat well plates (Corning®) in a 150 µl assay consisting of the following final concentrations: target cells, $13.3 \times 10^4$ cells/ml; complement, 15%; antibody range 10 to 0.01 ug/ml. For controls, target cells only were incubated in the absence (target background) or presence (target & complement background) of complement, and complement (complement background) was incubated in media only. Plates were centrifuged for 2 min at 160×g and incubated in humified $CO_2$ atmosphere in 37° C. for 2-3 hours. Cell death was measured using the CellTiter 96® kit (Promega®) according to the manufacturer's guidelines including an additional incubation period of 3-4 hours. Death of target cells was quantified by reading absorbance at 492 nm and percentage cytotoxicity was calculated using the following formula: 100×[sample−mean (target & complement background)]/[mean (complement background)−mean (target & complement background)]; $EC_{50}$ values were calculated using non-linear regression analysis by GraphPad Prism® software.

Novel Humanised SC104 Antibody Variants with Lower Predicted Immunogenicity have Potent Cytotoxicity Against Human Colon Tumour Cells Cytotoxicity against colon tumour cells of humanised SC104 variants with lower predicted immunogenicity was tested in antibody-dependent cell-mediated cytotoxicity and complement-dependent-cytotoxicity assays. The humanised SC104 antibody variants and the chimeric SC104 antibody, but not the human isotype control, had potent antibody-dependent cell-mediated cytotoxicity activity against C170 tumour cells using peripheral blood mononuclear cells of a normal human donor (FIG. 13). Similar results were obtained using peripheral blood mononuclear cells from other human donors (data not shown). FIG. 14 shows that the same panel of humanised SC104 antibody variants and the chimeric SC104 antibody, but not the human isotype control, had potent complement-dependent-cytotoxicity activity against Colo205 tumour cells using human complement. In addition, all other humanised SC104 antibody variants with lower predicted immunogenicity had potent antibody-dependent cell-mediated cytotoxicity and complement-dependent cytotoxic activity against Colo205 tumour cells (data not shown). In line with the differential direct cell killing data, the 1U6A-derived SC104 antibody variants showed higher antibody-dependent cell-mediated cytotoxicity and complement-dependent-cytotoxicity activity compared with 1QLR-derived SC104 antibody variants. This hierarchy in immune-mediated cytotoxic activity was unexpected given the similar binding activity of the different SC104 antibody variants (Table 6).

Example 6

Immunohistochemistry Protocol

A multi-tumour human tissue microarray containing samples of each tumour type from 10-12 different donors was screened for binding to biotinylated humanised SC104 antibody variants using immunohistochemistry. Biotinylated human IgG$_1$ isotype was used for negative control staining. The tissue microarray sections were subjected to a series of different antigen retrieval strategies, including modification of temperature, pressure, and pH. In addition, a dilution series of the primary antibody was performed to obtain the best possible signal to noise ratio. Immunoreactivity by the antibody was graded by visual inspection in a four step scale based on staining intensity and percentage of positive cells.
Humanised SC104 Antibody Variant Binds to Various Human Cancer Types A number of different cancer types from different human patients were analysed for binding with a humanised SC104 antibody possessing lower predicted immunogenicity (SEQ ID NO:7/SEQ ID NO:50). The humanised SC104 antibody, but not the human isotype control, bound to human colon cancer tissues demonstrating the specificity of the binding conditions used (data not shown). Table 7 summarises that positive membrane staining was found in colon cancer (75%). Surprisingly, positive staining was found in pancreatic cancer (70%) and to a lower extent in ovarian cancers (25%) and lung cancers (16.7%). In contrast, no staining was observed with kidney cancers in the limited sample size analysed. These results indicate that the humanised SC104 antibody with low predicted immunogenicity is useful for tumour diagnosis in indications of colorectal, pancreatic, ovarian and lung malignancies. In addition, one can envisage that the humanised SC104 antibody with low predicted immunogenicity is useful for the therapeutic treatment of colorectal, pancreatic, ovarian and lung cancer in humans. Such anti-tumour efficacy in vivo could be evaluated in mouse tumour xenograft models.

Example 7

Effector Function Enhancement of SC104 Antibodies

Effector function of antibodies can be enhanced by increasing antibody-dependent cell-mediated cytotoxicity or complement-dependent-cytotoxicity or by the combination of antibody-dependent cell-mediated cytotoxicity and complement-dependent-cytotoxicity.
ADCC Enhancement SC104 antibody variants and chimeric SC104 were engineered for enhanced antibody-dependent cell-mediated cytotoxicity (ADCC) activity using standard modifications to the Fc region of the antibody. Standard methods include for example protein-engineering or glyco-engineering of the Fc region of the antibody.

As an example of protein-engineering, mutations in the constant heavy chain sequences were generated as described by Lazar et al., 2006 (Lazar, Dang et al. 2006). Specifically, S122D, S181A, I215E mutations were introduced into the Fc sequence SEQ ID NO:52, to form SEQ ID NO:53. A number of humanised antibodies along with the chimeric antibody possessing the enhanced Fc-region SEQ ID NO:52 were tested in ADCC assays following their expression in CHO cells and purification by protein A chromatography as described in Example 2. ADCC function was measured as described in Example 5.

As an example of glyco-engineering, CHO cells producing humanised SC104 antibody variants or chimeric SC104 antibody were incubated for 8 to 10 days with kifunensin (0.25 m/ml) according to Zhou et al. (Zhou, Shankara et al. 2008). Subsequently antibody was purified as described in Example 2, and ADCC function was measured as described in Example 5.

Another example of glyco-engineering used the Potelligent® method as described in Shinkawa T. et al., 2003 (J Biol Chem 278: 3466-73). The variable light and heavy chain regions of the humanised antibody variants were expressed as an IgG1 on a standard constant region backbone. The sequence of the constant heavy chain was GenBank P01857.1 and the sequence of the constant light chain was NCBI accession number P01834. ADCC function was measured as described in Example 5.
Effector Enhanced SC104 Antibody Variants and Chimeric SC104 Antibody have Increased Antibody-Dependent Cell-Mediated Cytotoxicity In a series of experiments protein-engineering or glyco-engineering was applied to increase antibody-dependent cell-mediated cytotoxicity of chimeric SC104 antibody and SC104 antibody variants with low predicted immunogenicity. Compared with the unmodified antibodies, the Fc-engineered (SEQ ID NO:53) or kifunensin-treated SC104 humanised antibody variants and chimeric SC104 antibody showed increased antibody-dependent cell-mediated cytotoxicity against Colo205 tumour cells. FIG. 15 shows an example of markedly increased killing of human colon cancer cell WiDr (ATCC accession number CCL-218) by kifunensin-treated humanised SC104 antibody with lower predicted immunogenicity (SEQ ID NO:7/SEQ ID NO:50). FIG. 16 shows an example for markedly increased killing of human colon cancer cell Colo201 (ATCC accession number CCL-224) by Potelligent®-treated humanised SC104 antibody with lower predicted immunogenicity (SEQ ID NO:7/SEQ ID NO:94, the sequence of the constant heavy chain and the sequence of the constant light chain were GenBank P01857.1 and NCBI accession number P01834, respectively).

Example 8

Prophylactic Mouse Xenograft HT29 Tumour Model

Female BALB/c nude mice were inoculated subcutaneously with $2\times10^6$ human colon cancer HT29 cells (ATCC accession number HTB-38). On the same day as tumour cell inoculation (day 0), mice were randomised based on body weight into two treatment groups (n=10 per group). Each group was treated intraperitoneally with either the vehicle control (PBS, 10 ml/kg) or humanised SC104 antibody (10 mg/kg). The vehicle control and humanised SC104 antibody were administered twice weekly for four weeks. Tumour volume was calculated three times weekly using the following formula: Volume $(mm^3)$=length×diameter$^2$×π/6.

During the course of the study some mice had to be culled due to excessive body weight loss resulting in reduced mouse numbers for vehicle control (n=6) and antibody (n=9) treatment groups. Upon termination of the study (day 27), tumours were excised post-mortem from all mice, cleaned of skin and weighed.

Therapeutic Mouse Xenograft Colo201 Tumour Model

Female athymic nude mice were inoculated subcutaneously with $5\times10^6$ human colon cancer Colo201 (ATCC accession number CCL-224). After the tumour volume reached ~110 mm$^3$ (day 0), mice were randomised into two treatment groups (n=10 per group). Each group was treated intraperitoneally with either the vehicle control (PBS, 10 ml/kg) or humanised Potelligent®-engineered (as described in Example 7) SC104 antibody (10 mg/kg). The vehicle control and humanised Potelligent®-engineered SC104 antibody were administered twice weekly over 38 days. Tumour volume was calculated two times weekly using the following formula: Volume $(mm^3)$=½ $(a^2 \times b)$ where 'a' is the smallest diameter and 'b' is the largest diameter.

Potent Anti-Tumour Efficacy of Humanised SC104 Antibody with Lower Predicted Immunogenicity In Vivo Treatment of tumour-bearing mice with humanised SC104 antibody with lower predicted immunogenicity (SEQ ID NO:7/SEQ ID NO:50) resulted in significant reduced tumour volume and tumour weight compared with vehicle control treatment in a prophylactic HT29 tumour model (FIG. 17). Moreover, in a therapeutic Colo201 treatment model, humanised Potelligent®-engineered SC104 antibody with lower predicted immunogenicity (SEQ ID NO:7/SEQ ID NO:94) showed significant anti-tumour activity (FIG. 18).

One can envisage that humanised SC104 antibody variants with low predicted immunogenicity are useful for the treatment of colorectal cancers in humans either as mono-therapy or in combination with other therapeutic anti-tumour agents, for example chemotherapy, small molecules or biologics.

TABLE 1

CDR sequences of SC104.

| Variable region | CDR number | CDR Sequence |
|---|---|---|
| $V_H$ | 1 | SGYSWH (Kabat) |
| | | GYSITSGYSWH (AbM) |
| $V_H$ | 2 | HIHFSGRPTYNPSLSS |
| $V_H$ | 3 | KGKGSDDGLNY |

TABLE 1 - continued

CDR sequences of SC104.

| Variable region | CDR number | CDR Sequence |
|---|---|---|
| $V_L$ | 1 | SASSSLSYIH |
| $V_L$ | 2 | DTSNLAS |
| $V_L$ | 3 | FQGSEYPLT |

TABLE 2

Few initial SC104 humanised antibody variants retained binding activity to SC104 antigen positive human colon cancer cell line C170

| SC104 antibody form | $V_L$ (SEQ ID NO)/$V_H$ (SEQ ID NO) | C170 |
|---|---|---|
| humanised | SEQ ID NO: 18/SEQ ID NO: 10 | <1 |
| humanised | SEQ ID NO: 18/SEQ ID NO: 17 | <1 |
| humanised | SEQ ID NO: 7/SEQ ID NO: 9 | <1 |
| humanised | SEQ ID NO: 16/SEQ ID NO: 9 | <1 |
| humanised | SEQ ID NO: 8/SEQ ID NO: 10 | <1 |
| humanised | SEQ ID NO: 8/SEQ ID NO: 17 | 11.0 |
| humanised | SEQ ID NO: 7/SEQ ID NO: 15 | 23.4 |
| humanised | SEQ ID NO: 16/SEQ ID NO: 15 | 29.4 |
| humanised | SEQ ID NO: 18/SEQ ID NO: 12 | 64.5 |
| humanised | SEQ ID NO: 16/SEQ ID NO: 11 | 73.9 |
| humanised | SEQ ID NO: 8/SEQ ID NO: 12 | 74.6 |
| humanised | SEQ ID NO: 7/SEQ ID NO: 11 | 81.9 |
| humanised | SEQ ID NO: 16/SEQ ID NO: 13 | 91.0 |
| humanised | SEQ ID NO: 7/SEQ ID NO: 13 | 96.1 |
| chimeric | SEQ ID NO: 4/SEQ ID NO: 2 | 100 | expressed as percentage binding relative to chimeric SC104 binding; when tested similar data were obtained in other experiments

TABLE 3

Sequence comparison of framework region immediately prior to Kabat-defined CDR-H1

| Source of amino acid sequence | Five amino acids prior to Kabat-defined CDR-H1 |
|---|---|
| Murine donor Sequence | GYSIT |
| 1U6A acceptor sequence | GGSIS |
| 1QLR acceptor sequence | GGSFS |

TABLE 4

Residues I, L, and V at position 29 in combination with residue Y at position 27 in 1U6A framework 1 of variable heavy chain confer highest binding activity of humanised SC104 antibody variants with lower predicted immunogenicity to SC104 antigen positive human colon cancer cell line C170

| SC104 antibody form | Residue substitution at position 29 | $V_L$ (SEQ ID NO)/$V_H$ (SEQ ID NO) | C170 |
|---|---|---|---|
| chimeric | I | SEQ ID NO: 4/SEQ ID NO: 2 | 100.0 |
| humanised | I | SEQ ID NO: 7/SEQ ID NO: 50 | 96.5 |
| humanised | L | SEQ ID NO: 7/SEQ ID NO: 62 | 79.4 |
| humanised | V | SEQ ID NO: 7/SEQ ID NO: 70 | 71.4 |
| humanised | T | SEQ ID NO: 7/SEQ ID NO: 69 | 20.3 |

TABLE 4-continued

Residues I, L, and V at position 29 in combination with residue Y at position 27 in 1U6A framework 1 of variable heavy chain confer highest binding activity of humanised SC104 antibody variants with lower predicted immunogenicity to SC104 antigen positive human colon cancer cell line C170

| SC104 antibody form | Residue substitution at position 29 | $V_L$ (SEQ ID NO)/$V_H$ (SEQ ID NO) | C170 |
|---|---|---|---|
| humanised | M | SEQ ID NO: 7/SEQ ID NO: 63 | 15.1 |
| humanised | N | SEQ ID NO: 7/SEQ ID NO: 64 | 8.4 |
| humanised | Y | SEQ ID NO: 7/SEQ ID NO: 72 | 3.3 |
| humanised | H | SEQ ID NO: 7/SEQ ID NO: 60 | 2.5 |
| humanised | R | SEQ ID NO: 7/SEQ ID NO: 67 | 1.7 |
| humanised | Q | SEQ ID NO: 7/SEQ ID NO: 66 | 1.4 |
| humanised | P | SEQ ID NO: 7/SEQ ID NO: 65 | 1.4 |
| humanised | W | SEQ ID NO: 7/SEQ ID NO: 71 | 1.4 |
| humanised | A | SEQ ID NO: 7/SEQ ID NO: 54 | <1 |
| humanised | S | SEQ ID NO: 7/SEQ ID NO: 68 | <1 |
| humanised | F | SEQ ID NO: 7/SEQ ID NO: 58 | <1 |
| humanised | C | SEQ ID NO: 7/SEQ ID NO: 55 | <1 |
| humanised | G | SEQ ID NO: 7/SEQ ID NO: 59 | <1 |
| humanised | D | SEQ ID NO: 7/SEQ ID NO: 56 | <1 |
| humanised | E | SEQ ID NO: 7/SEQ ID NO: 57 | <1 |
| humanised | K | SEQ ID NO: 7/SEQ ID NO: 61 | <1 |

Expressed as mean percentage activity relative to chimeric SC104 calculated from 2 experiments

TABLE 5

Positive charged residues R and K at position 71 in 1U6A framework 3 of variable heavy chain confer highest binding activity of humanised SC104 antibody variants with lower predicted immunogenicity to SC104 antigen positive human colon cancer cell line C170

| SC104 antibody form | Residue substitution at position 71 | $V_L$ (SEQ ID NO)/$V_H$ (SEQ ID NO) | C170 |
|---|---|---|---|
| chimeric | R | SEQ ID NO: 4/SEQ ID NO: 2 | 100.0 |
| humanised | R | SEQ ID NO: 7/SEQ ID NO: 50 | 95.7 |
| humanised | K | SEQ ID NO: 7/SEQ ID NO: 81 | 115.7 |
| humanised | H | SEQ ID NO: 7/SEQ ID NO: 79 | 83.1 |
| humanised | M | SEQ ID NO: 7/SEQ ID NO: 83 | 82.9 |
| humanised | F | SEQ ID NO: 7/SEQ ID NO: 77 | 79.6 |
| humanised | A | SEQ ID NO: 7/SEQ ID NO: 73 | 70.8 |
| humanised | P | SEQ ID NO: 7/SEQ ID NO: 85 | 58.4 |
| humanised | Y | SEQ ID NO: 7/SEQ ID NO: 91 | 60.7 |
| humanised | S | SEQ ID NO: 7/SEQ ID NO: 87 | 52.1 |
| humanised | Q | SEQ ID NO: 7/SEQ ID NO: 86 | 60.1 |
| humanised | C | SEQ ID NO: 7/SEQ ID NO: 74 | 47.3 |
| humanised | D | SEQ ID NO: 7/SEQ ID NO: 75 | 48.2 |
| humanised | G | SEQ ID NO: 7/SEQ ID NO: 78 | 54.1 |
| humanised | T | SEQ ID NO: 7/SEQ ID NO: 88 | 43.5 |
| humanised | I | SEQ ID NO: 7/SEQ ID NO: 80 | 23.5 |
| humanised | L | SEQ ID NO: 7/SEQ ID NO: 82 | 31.9 |
| humanised | N | SEQ ID NO: 7/SEQ ID NO: 84 | 25.6 |
| humanised | V | SEQ ID NO: 7/SEQ ID NO: 89 | 36.4 |
| humanised | W | SEQ ID NO: 7/SEQ ID NO: 90 | 25.3 |
| humanised | E | SEQ ID NO: 7/SEQ ID NO: 76 | 22.6 | expressed as mean percentage activity relative to chimeric SC104 calculated from 2-3 experiments

TABLE 6

Humanised SC104 antibody variants with low predicted immunogenicity demonstrate unexpected functional differences in direct killing activity, antibody-dependent cell-mediated-cytotoxicity (ADCC) and complement-dependent cytotoxicity (CDC) activities despite essentially identical binding activities against SC104 antigen positive human colon cancer cells

| SC104 antibody form | $V_L$ (SEQ ID NO)/ $V_H$ (SEQ ID NO) | Binding | | Direct killing | ADCC | | CDC |
|---|---|---|---|---|---|---|---|
| | | C170 | Colo205 | C170 | C170 | Colo205 | Colo205 |
| chimeric | SEQ ID NO: 4/ SEQ ID NO: 2 | 100 | 100 | 100 | 100 | 100 | 100 |
| humanised | SEQ ID NO: 7/SEQ ID NO: 25 | 101.4 | 104.8 | 98.9 | 154.2 | 120.3 | 54.1 |
| humanised | SEQ ID NO: 7/SEQ ID NO: 50 | 106.8 | 112.0 | 89.4 | 162.5 | 203.5 | 136.0 |
| humanised | SEQ ID NO: 8/SEQ ID NO: 26 | 99.0 | 95.8 | 48.7 | 32.3 | 84.4 | 9.9 |
| humanised | SEQ ID NO: 8/SEQ ID NO: 38 | 103.5 | 104.3 | 50.3 | 47.3 | nd | 20.1 | expressed as percentage activity relative to chimeric SC104; nd, not determined; when tested similar data were obtained in other experiments

TABLE 7

Humanised SC104 antibody variant with low predicted immunogenicity binds to various human tumour types

| Tumour type | Number analysed | Percentage of membranous immunostaining | | | |
|---|---|---|---|---|---|
| | | Negative | weak | moderate | strong |
| Colon | 12 | 25 | 41.7 | 16.7 | 16.7 |
| Pancreas | 10 | 30 | 10 | 30 | 30 |
| Ovary | 12 | 75 | 16.7 | 8.3 | 0 |
| Lung | 12 | 83.3 | 16.7 | 0 | 0 |
| Kidney | 12 | 100 | 0 | 0 | 0 |

BIBLIOGRAPHY

Benhar, I. (2007). "Design of synthetic antibody libraries." Expert Opin Biol Ther 7(5): 763-79.

Brekke, O. H., B. Bremnes, et al. (1993). "Human IgG3 can adopt the disulfide bond pattern characteristic for IgG1 without resembling it in complement mediated cell lysis." Mol Immunol 30(16): 1419-25.

Christensen, P. A., A. Danielczyk, et al. (2009). "Modifying antibody specificity by chain shuffling of V/V between antibodies with related specificities." Scand J Immunol 69(1): 1-10.

Dall'Acqua, W. F., K. E. Cook, et al. (2006). "Modulation of the effector functions of a human IgG1 through engineering of its hinge region." J Immunol 177(2): 1129-38.

Dall'Acqua, W. F., P. A. Kiener, et al. (2006). "Properties of human IgG1s engineered for enhanced binding to the neonatal Fc receptor (FcRn)." J Biol Chem 281(33): 23514-24.

Dall'Acqua, W. F., R. M. Woods, et al. (2002). "Increasing the affinity of a human IgG1 for the neonatal Fc receptor: biological consequences." J Immunol 169(9): 5171-80.

Dübel, S. (2007). Handbook of Therapeutic Antibodies, Wiley-VCH, Weinheim.

Durrant, L. G., S. J. Harding, et al. (2006). "A new anticancer glycolipid monoclonal antibody, SC104, which directly induces tumor cell apoptosis." Cancer Res 66(11): 5901-9.

Ferrara, C., P. Brunker, et al. (2006). "Modulation of therapeutic antibody effector functions by glycosylation engineering: influence of Golgi enzyme localization domain and co-expression of heterologous beta1,4-N-acetylglucosaminyltransferase III and Golgi alpha-mannosidase II." Biotechnol Bioeng 93(5): 851-61.

Fishburn, C. S. (2008). "The pharmacology of PEGylation: balancing PD with PK to generate novel therapeutics." J Pharm Sci 97(10): 4167-83.

Gavel, Y. and G. von Heijne (1990). "Sequence differences between glycosylated and non-glycosylated Asn-X-Thr/Ser acceptor sites: implications for protein engineering." Protein Eng 3(5): 433-42.

Greener, A., Callahan, M. and Jerpseth, B (1996). In Vitro Mutagenesis Protocols, Humana press, NJ.

Hinton, P. R., M. G. Johlfs, et al. (2004). "Engineered human IgG antibodies with longer serum half-lives in primates." J Biol Chem 279(8): 6213-6.

Hinton, P. R., J. M. Xiong, et al. (2006). "An engineered human IgG1 antibody with longer serum half-life." J Immunol 176(1): 346-56.

Idusogie, E. E., P. Y. Wong, et al. (2001). "Engineered antibodies with increased activity to recruit complement." J Immunol 166(4): 2571-5.

Jones, A. J., D. I. Papac, et al. (2007). "Selective clearance of glycoforms of a complex glycoprotein pharmaceutical caused by terminal N-acetylglucosamine is similar in humans and cynomolgus monkeys." Glycobiology 17(5): 529-40.

Kabat, E. A. W., T. T; Perry, H; Gottesman, K; Foeller, C (1991). Sequences of Proteins of Immunological Interest, NIH publication no. 91-3242, Bethesda, Md.

Kanda, Y., T. Yamada, et al. (2007). "Comparison of biological activity among nonfucosylated therapeutic IgG1 antibodies with three different N-linked Fc oligosaccharides: the high-mannose, hybrid, and complex types." Glycobiology 17(1): 104-18.

Kaneko, Y., F. Nimmerjahn, et al. (2006). "Anti-inflammatory activity of immunoglobulin G resulting from Fc sialylation." Science 313(5787): 670-3.

Kolkman, J. A. and W. P. Stemmer (2001). "Directed evolution of proteins by exon shuffling." Nat Biotechnol 19(5): 423-8.

Kopsidas, G., A. S. Roberts, et al. (2006). "In vitro improvement of a shark IgNAR antibody by Qbeta replicase mutation and ribosome display mimics in vivo affinity maturation." Immunol Left 107(2): 163-8.

Lazar, G. A., W. Dang, et al. (2006). "Engineered antibody Fc variants with enhanced effector function." Proc Natl Acad Sci USA 103(11): 4005-10.

Li, H., N. Sethuraman, et al. (2006). "Optimization of humanized IgGs in glycoengineered Pichia pastoris." Nat Biotechnol 24(2): 210-5.

Loo, D., N. Pryer, et al. (2007). "The glycotope-specific RAV12 monoclonal antibody induces oncosis in vitro and has antitumor activity against gastrointestinal adenocarcinoma tumor xenografts in vivo." Mol Cancer Ther 6(3): 856-65.

Michaelsen, T. E., A. Aase, et al. (1990). "Enhancement of complement activation and cytolysis of human IgG3 by deletion of hinge exons." Scand J Immunol 32(5): 517-28.

Natsume, A., M. In, et al. (2008). "Engineered antibodies of IgG1/IgG3 mixed isotype with enhanced cytotoxic activities." Cancer Res 68(10): 3863-72.

Norderhaug, L., O. H. Brekke, et al. (1991). "Chimeric mouse human IgG3 antibodies with an IgG4-like hinge region induce complement-mediated lysis more efficiently than IgG3 with normal hinge." Eur J Immunol 21(10): 2379-84.

Nozawa, S., D. Aoki, et al. (2004). "HMMC-1: a humanized monoclonal antibody with therapeutic potential against Mullerian duct-related carcinomas." Clin Cancer Res 10(20): 7071-8.

Peled, J. U., F. L. Kuang, et al. (2008). "The biochemistry of somatic hypermutation." Annu Rev Immunol 26: 481-511.

Petkova, S. B., S. Akilesh, et al. (2006). "Enhanced half-life of genetically engineered human IgG1 antibodies in a humanized FcRn mouse model: potential application in humorally mediated autoimmune disease." Int Immunol 18(12): 1759-69.

Queen, C., W. P. Schneider, et al. (1989). "A humanized antibody that binds to the interleukin 2 receptor." Proc Natl Acad Sci USA 86(24): 10029-33.

Rammensee, H., J. Bachmann, et al. (1999). "SYFPEITHI: database for MHC ligands and peptide motifs." Immunogenetics 50(3-4): 213-9.

Shields, R. L., A. K. Namenuk, et al. (2001). "High resolution mapping of the binding site on human IgG1 for Fc gamma R1, Fc gamma R11, Fc gamma RIII, and FcRn and design of IgG1 variants with improved binding to the Fc gamma R." *J Biol Chem* 276(9): 6591-604.

Shinkawa, T., K. Nakamura, et al. (2003). "The absence of fucose but not the presence of galactose or bisecting N-acetylglucosamine of human IgG 1 complex-type oligosaccharides shows the critical role of enhancing antibody-dependent cellular cytotoxicity." *J Biol Chem* 278 (5): 3466-73.

Stavenhagen, J. B., S. Gorlatov, et al. (2007). "Fc optimization of therapeutic antibodies enhances their ability to kill tumor cells in vitro and controls tumor expansion in vivo via low-affinity activating Fcgamma receptors." *Cancer Res* 67(18): 8882-90.

Tan, L. K., R. J. Shopes, et al. (1990). "Influence of the hinge region on complement activation, C1q binding, and segmental flexibility in chimeric human immunoglobulins." *Proc Natl Acad Sci USA* 87(1): 162-6.

Thie, H., B. Voedisch, et al. (2009). "Affinity maturation by phage display." *Methods Mol Biol* 525: 309-22, xv.

Ye, S. Q. (2007). *Bioinformatics: A Practical Approach*, Chapman & Hall/CRC

Zhou, Q., S. Shankara, et al. (2008). "Development of a simple and rapid method for producing non-fixosylated oligomannose containing antibodies with increased effector function." *Biotechnol Bioeng* 99(3): 652-65.

PATENT REFERENCES

WO 2005/108430
WO 2008/006554
U.S. Pat. No. 5,225,539
U.S. Pat. No. 6,423,511
U.S. Pat. No. 6,872,392
U.S. Pat. No. 6,180,370
U.S. Pat. No. 6,277,375
U.S. Pat. No. 6,821,505
U.S. Pat. No. 6,602,684
U.S. Pat. No. 6,180,370
U.S. Pat. No. 7,083,784
U.S. Pat. No. 7,217,797
U.S. Pat. No. 7,326,681
U.S. Pat. No. 7,388,081
US 20090142340
US 20090068175
US 20090092599

SUMMARY OF SEQUENCE LISTING

SEQ ID NO:1: Amino acid sequence of murine SC104 heavy chain variable region.
SEQ ID NO:2: Amino acid sequence of chimeric SC104 heavy chain with mouse variable region and human IgG1 backbone (human IgG1 heavy chain CH1, hinge, CH2 & CH3 domains).
SEQ ID NO:3: Amino acid sequence of murine SC104 light chain variable region.
SEQ ID NO:4: Amino acid sequence of chimeric SC104 light chain with mouse variable region and human light chain constant region.
SEQ ID NO:5: Heavy chain signal sequence.
SEQ ID NO:6: Light chain signal sequence.
SEQ ID NO:7: 1U6A-based SC104 light chain polypeptide sequence incorporating substitution A15P.
SEQ ID NO:8: 1QLR-based SC104 light chain.
SEQ ID NO:9: Kabat-grafted 1U6A-based SC104 heavy chain polypeptide sequence.
SEQ ID NO:10: Kabat-grafted 1QLR-based SC104 heavy chain polypeptide sequence.
SEQ ID NO:11: AbM-grafted CDR-H1, Kabat-defined CDR-H2 and CDR-H3 of 1U6A-based SC104 heavy chain polypeptide sequence.
SEQ ID NO:12: AbM-grafted CDR-H1, Kabat-defined CDR-H2 and CDR-H3 of 1QLR-based SC104 heavy chain polypeptide sequence.
SEQ ID NO:13: AbM-grafted CDR-H1, Kabat-defined CDR-H2 and CDR-H3 of 1U6A-based SC104 heavy chain polypeptide sequence incorporating six substitutions.
SEQ ID NO:14: AbM-grafted CDR-H1, Kabat-defined CDR-H2 and CDR-H3 of 1U6A-based SC104 heavy chain polypeptide sequence incorporating eight substitutions.
SEQ ID NO:15: Kabat-grafted 1U6A-based SC104 heavy chain polypeptide sequence incorporating six substitutions.
SEQ ID NO:16: 1U6A-based SC104 light chain polypeptide sequence incorporating three substitutions.
SEQ ID NO:17: Kabat-grafted 1QLR-based SC104 heavy chain polypeptide sequence incorporating four substitutions.
SEQ ID NO:18: 1QLR-based SC104 light chain polypeptide sequence incorporating two substitutions.
SEQ ID NO:19: AbM-grafted CDR-H1, Kabat-defined CDR-H2 and CDR-H3 of 1U6A-based SC104 heavy chain polypeptide sequence incorporating substitutions Q1E and Q46E.
SEQ ID NO:20: AbM-grafted CDR-H1, Kabat-defined CDR-H2 and CDR-H3 of 1U6A-based SC104 heavy chain polypeptide sequence incorporating substitutions Q1E and I48M.
SEQ ID NO:21: AbM-grafted CDR-H1, Kabat-defined CDR-H2 and CDR-H3 of 1U6A-based SC104 heavy chain polypeptide sequence incorporating substitutions Q1E and V67I.
SEQ ID NO:22: AbM-grafted CDR-H1, Kabat-defined CDR-H2 and CDR-H3 of 1U6A-based SC104 heavy chain polypeptide sequence incorporating substitutions Q1E and T68S.
SEQ ID NO:23: AbM-grafted CDR-H1, Kabat-defined CDR-H2 and CDR-H3 of 1U6A-based SC104 heavy chain polypeptide sequence incorporating substitutions Q1E and V71R.
SEQ ID NO:24: AbM-grafted CDR-H1, Kabat-defined CDR-H2 and CDR-H3 of 1U6A-based SC104 heavy chain polypeptide sequence incorporating substitutions Q1E and E72D.
SEQ ID NO:25: AbM-grafted CDR-H1, Kabat-defined CDR-H2 and CDR-H3 of 1U6A-based SC104 heavy chain polypeptide sequence incorporating substitution V71R.
SEQ ID NO:26: AbM-grafted CDR-H1, Kabat-defined CDR-H2 and CDR-H3 of 1QLR-based SC104 heavy chain polypeptide sequence incorporating substitution V71R.
SEQ ID NO:27: Kabat-grafted 1QLR-based SC104 heavy chain polypeptide sequence incorporating substitution V71R.
SEQ ID NO:28: Kabat-grafted 1U6A-based SC104 heavy chain polypeptide sequence incorporating substitution V71R.
SEQ ID NO:29: Kabat-grafted 1QLR-based SC104 heavy chain polypeptide sequence incorporating substitutions G27Y and V71R.
SEQ ID NO:30: Amino acid sequence of chimeric SC104 heavy chain with mouse variable region and human IgG1 backbone (human IgG1 heavy chain CH1, hinge, CH2 & CH3 domains) incorporating CDR-H2 substitution F53W.

SEQ ID NO:31: Amino acid sequence of chimeric SC 104 heavy chain with mouse variable region and human IgG1 backbone (human IgG1 heavy chain CH1, hinge, CH2 & CH3 domains) incorporating CDR-H2 substitution F53Y.

SEQ ID NO:32: Amino acid sequence of chimeric SC104 heavy chain with mouse variable region and human IgG 1 backbone (human IgG 1 heavy chain CH1, hinge, CH2 & CH3 domains) incorporating CDR-H2 substitution F53P.

SEQ ID NO:33: AbM-grafted CDR-H1, Kabat-defined CDR-H2 and CDR-H3 of 1QLR-based SC104 heavy chain polypeptide sequence incorporating substitutions S64K and V71R.

SEQ ID NO:34: AbM-grafted CDR-H1, Kabat-defined CDR-H2 and CDR-H3 of 1QLR-based SC104 heavy chain polypeptide sequence incorporating substitutions S64L and V71R.

SEQ ID NO:35: AbM-grafted CDR-H1, Kabat-defined CDR-H2 and CDR-H3 of 1QLR-based SC104 heavy chain polypeptide sequence incorporating substitutions S64H and V71R.

SEQ ID NO:36: AbM-grafted CDR-H1, Kabat-defined CDR-H2 and CDR-H3 of 1QLR-based SC104 heavy chain polypeptide sequence incorporating substitutions S64F and V71R.

SEQ ID NO:37: AbM-grafted CDR-H1, Kabat-defined CDR-H2 and CDR-H3 of 1QLR-based SC104 heavy chain polypeptide sequence incorporating substitutions S64R and V71R.

SEQ ID NO:38: Kabat-grafted 1QLR-based SC104 heavy chain polypeptide sequence incorporating substitutions G27Y, F29I, T30S, S64K and V71R.

SEQ ID NO:39: AbM-grafted CDR-H1, Kabat-defined CDR-H2 and CDR-H3 of 1U6A-based SC104 heavy chain polypeptide sequence incorporating substitutions S64K and V71R.

SEQ ID NO:40: AbM-grafted CDR-H1, Kabat-defined CDR-H2 and CDR-H3 of 1U6A-based SC104 heavy chain polypeptide sequence incorporating substitutions S64L and V71R.

SEQ ID NO:41: AbM-grafted CDR-H1, Kabat-defined CDR-H2 and CDR-H3 of 1U6A-based SC104 heavy chain polypeptide sequence incorporating substitutions S64H and V71R.

SEQ ID NO:42: AbM-grafted CDR-H1, Kabat-defined CDR-H2 and CDR-H3 of 1U6A-based SC104 heavy chain polypeptide sequence incorporating substitutions S64F and V71R.

SEQ ID NO:43: AbM-grafted CDR-H1, Kabat-defined CDR-H2 and CDR-H3 of 1U6A-based SC104 heavy chain polypeptide sequence incorporating substitutions S64R and V71R.

SEQ ID NO:44: AbM-grafted CDR-H1, Kabat-defined CDR-H2 and CDR-H3 of 1U6A-based SC 104 heavy chain polypeptide sequence incorporating substitutions S40P and V71R.

SEQ ID NO:45: AbM-grafted CDR-H1, Kabat-defined CDR-H2 and CDR-H3 of 1U6A-based SC104 heavy chain polypeptide sequence incorporating substitutions S40P, S64K and V71R.

SEQ ID NO:46: AbM-grafted CDR-H1, Kabat-defined CDR-H2 and CDR-H3 of 1U6A-based SC 104 heavy chain polypeptide sequence incorporating substitutions S40P, S64L and V71R.

SEQ ID NO:47: AbM-grafted CDR-H1, Kabat-defined CDR-H2 and CDR-H3 of 1U6A-based SC104 heavy chain polypeptide sequence incorporating substitutions S40P, S64H and V71R.

SEQ ID NO:48: AbM-grafted CDR-H1, Kabat-defined CDR-H2 and CDR-H3 of 1U6A-based SC104 heavy chain polypeptide sequence incorporating substitutions S40P, S64F and V71R.

SEQ ID NO:49: AbM-grafted CDR-H1, Kabat-defined CDR-H2 and CDR-H3 of 1U6A-based SC104 heavy chain polypeptide sequence incorporating substitutions S40P, S64R and V71R.

SEQ ID NO:50: Kabat-grafted 1U6A-based SC104 heavy chain polypeptide sequence incorporating substitutions G27Y, T30S, S40P, S64K and V71R.

SEQ ID NO:51: Amino acid sequence of chimeric SC104 heavy chain with mouse variable region and human IgG1 backbone (human IgG1 heavy chain CH1, hinge, CH2 & CH3 domains) incorporating substitution N60D.

SEQ ID NO:52: Heavy chain constant region incorporating hinge, CH1, CH2 and CH3 domains.

SEQ ID NO:53: Heavy chain constant region incorporating hinge, CH1, CH2 and CH3 domains, incorporating amino acid substitutions S122D, S181A, I215E.

SEQ ID NO:54: Kabat-grafted 1U6A-based SC104 heavy chain polypeptide sequence incorporating substitutions G27Y, I29A, T30S, S40P, S64K and V71R.

SEQ ID NO:55: Kabat-grafted 1U6A-based SC104 heavy chain polypeptide sequence incorporating substitutions G27Y, I29C, T30S, 540P, S64K and V71R.

SEQ ID NO:56: Kabat-grafted 1U6A-based SC104 heavy chain polypeptide sequence incorporating substitutions G27Y, I29D, T30S, S40P, S64K and V71R.

SEQ ID NO:57: Kabat-grafted 1U6A-based SC104 heavy chain polypeptide sequence incorporating substitutions G27Y, I29E, T30S, S40P, S64K and V71R.

SEQ ID NO:58: Kabat-grafted 1U6A-based SC104 heavy chain polypeptide sequence incorporating substitutions G27Y, I29F, T30S, S40P, S64K and V71R.

SEQ ID NO:59: Kabat-grafted 1U6A-based SC104 heavy chain polypeptide sequence incorporating substitutions G27Y, I29G, T30S, S40P, S64K and V71R.

SEQ ID NO:60: Kabat-grafted 1U6A-based SC104 heavy chain polypeptide sequence incorporating substitutions G27Y, I29H, T30S, S40P, S64K and V71R.

SEQ ID NO:61: Kabat-grafted 1U6A-based SC 104 heavy chain polypeptide sequence incorporating substitutions G27Y, I29K, T30S, S40P, S64K and V71R.

SEQ ID NO:62: Kabat-grafted 1U6A-based SC104 heavy chain polypeptide sequence incorporating substitutions G27Y, I29L, T30S, S40P, S64K and V71R.

SEQ ID NO:63: Kabat-grafted 1U6A-based SC104 heavy chain polypeptide sequence incorporating substitutions G27Y, I29M, T30S, S40P, S64K and V71R.

SEQ ID NO:64: Kabat-grafted 1U6A-based SC104 heavy chain polypeptide sequence incorporating substitutions G27Y, I29N, T30S, S40P, S64K and V71R.

SEQ ID NO:65: Kabat-grafted 1U6A-based SC104 heavy chain polypeptide sequence incorporating substitutions G27Y, I29P, T30S, S40P, S64K and V71R.

SEQ ID NO:66: Kabat-grafted 1U6A-based SC104 heavy chain polypeptide sequence incorporating substitutions G27Y, I29Q, T30S, S40P, S64K and V71R.

SEQ ID NO:67: Kabat-grafted 1U6A-based SC104 heavy chain polypeptide sequence incorporating substitutions G27Y, I29R, T30S, S40P, S64K and V71R.

SEQ ID NO:68: Kabat-grafted 1U6A-based SC104 heavy chain polypeptide sequence incorporating substitutions G27Y, I29S, T30S, 540P, S64K and V71R.

SEQ ID NO:69: Kabat-grafted 1U6A-based SC104 heavy chain polypeptide sequence incorporating substitutions G27Y, I29T, T30S, S40P, S64K and V71R.
SEQ ID NO:70: Kabat-grafted 1U6A-based SC104 heavy chain polypeptide sequence incorporating substitutions G27Y, I29V, T30S, S40P, S64K and V71R.
SEQ ID NO:71: Kabat-grafted 1U6A-based SC104 heavy chain polypeptide sequence incorporating substitutions G27Y, I29W, T30S, S40P, S64K and V71R.
SEQ ID NO:72: Kabat-grafted 1U6A-based SC104 heavy chain polypeptide sequence incorporating substitutions G27Y, I29Y, T30S, S40P, S64K and V71R.
SEQ ID NO:73: Kabat-grafted 1U6A-based SC104 heavy chain polypeptide sequence incorporating substitutions G27Y, T30S, S40P, S64K and V71A.
SEQ ID NO:74: Kabat-grafted 1U6A-based SC104 heavy chain polypeptide sequence incorporating substitutions G27Y, T30S, S40P, S64K and V71C.
SEQ ID NO:75: Kabat-grafted 1U6A-based SC104 heavy chain polypeptide sequence incorporating substitutions G27Y, T30S, S40P, S64K and V71D.
SEQ ID NO:76: Kabat-grafted 1U6A-based SC104 heavy chain polypeptide sequence incorporating substitutions G27Y, T30S, S40P, S64K and V71E.
SEQ ID NO:77: Kabat-grafted 1U6A-based SC104 heavy chain polypeptide sequence incorporating substitutions G27Y, T30S, S40P, S64K and V71F.
SEQ ID NO:78: Kabat-grafted 1U6A-based SC104 heavy chain polypeptide sequence incorporating substitutions G27Y, T30S, S40P, S64K and V71G.
SEQ ID NO:79: Kabat-grafted 1U6A-based SC104 heavy chain polypeptide sequence incorporating substitutions G27Y, T30S, S40P, S64K and V71H.
SEQ ID NO:80: Kabat-grafted 1U6A-based SC104 heavy chain polypeptide sequence incorporating substitutions G27Y, T30S, S40P, S64K and V71I.
SEQ ID NO:81: Kabat-grafted 1U6A-based SC104 heavy chain polypeptide sequence incorporating substitutions G27Y, T30S, S40P, S64K and V71K.
SEQ ID NO:82: Kabat-grafted 1U6A-based SC104 heavy chain polypeptide sequence incorporating substitutions G27Y, T30S, S40P, S64K and V71L.
SEQ ID NO:83: Kabat-grafted 1U6A-based SC104 heavy chain polypeptide sequence incorporating substitutions G27Y, T30S, S40P, S64K and V71M.
SEQ ID NO:84: Kabat-grafted 1U6A-based SC104 heavy chain polypeptide sequence incorporating substitutions G27Y, T30S, S40P, S64K and V71N.
SEQ ID NO:85: Kabat-grafted 1U6A-based SC104 heavy chain polypeptide sequence incorporating substitutions G27Y, T30S, S40P, S64K and V71P.
SEQ ID NO:86: Kabat-grafted 1U6A-based SC104 heavy chain polypeptide sequence incorporating substitutions G27Y, T30S, S40P, S64K and V71Q.
SEQ ID NO:87: Kabat-grafted 1U6A-based SC104 heavy chain polypeptide sequence incorporating substitutions G27Y, T30S, 540P, S64K and V71S.
SEQ ID NO:88: Kabat-grafted 1U6A-based SC104 heavy chain polypeptide sequence incorporating substitutions G27Y, T30S, 540P, S64K and V71T.
SEQ ID NO:89: Kabat-grafted 1U6A-based SC104 heavy chain polypeptide sequence incorporating substitutions G27Y, T30S, S40P, S64K and V71V.
SEQ ID NO:90: Kabat-grafted 1U6A-based SC104 heavy chain polypeptide sequence incorporating substitutions G27Y, T30S, S40P, S64K and V71 W.

SEQ ID NO:91: Kabat-grafted 1U6A-based SC104 heavy chain polypeptide sequence incorporating substitutions G27Y, T30S, S40P, S64K and V71Y.

SEQ ID NO:92: Heavy chain constant region incorporating hinge, CH1, CH2 and CH3 domains.

SEQ ID NO:93 Light chain constant domain

SEQ ID NO:94 Kabat-grafted 1U6A-based SC104 heavy chain polypeptide sequence incorporating substitutions G27Y, T30S, 540P, S64K and V71R

The invention claimed is:

1. A humanized antibody, comprising a VH binding domain having an amino acid sequence selected from the group consisting of the amino acid sequence of residues 1 to 120 of SEQ ID NO: 50, the amino acid sequence of residues 1 to 120 of SEQ ID NO: 38, an amino acid sequence having at least 95% identity with the amino acid sequence of residues 1 to 120 of SEQ ID NO: 50 provided that the residue at position 72 is Arg or Lys and that the VH CDR1 has the amino acid sequence of SEQ ID NO: 96, the VH CDR2 has the amino acid sequence of SEQ ID NO: 98, and the VH CDR3 has the amino acid sequence of SEQ ID NO: 100, and an amino acid sequence having at least 95% identity with the amino acid sequence of residues 1 to 120 of SEQ ID NO: 38 provided that the residue at position 72 is Arg or Lys and that the VH CDR1 has the amino acid sequence of SEQ ID NO: 96, the VH CDR2 has the amino acid sequence of SEQ ID NO: 98, and the VH CDR3 has the amino acid sequence of SEQ ID NO: 100, and a VL binding domain having an amino acid sequence selected from the group consisting of the amino acid sequence of residues 1 to 107 of SEQ ID NO: 7, the amino acid sequence of residues 1 to 107 of SEQ ID NO: 8, an amino acid sequence having at least 95% identity with the amino acid sequence of residues 1 to 107 of SEQ ID NO: 7 provided that the VL CDR1 has the amino acid sequence of SEQ ID NO: 188, the VL CDR2 has the amino acid sequence of SEQ ID NO: 190, and the VL CDR3 has the amino acid sequence of SEQ ID NO: 192, and an amino acid sequence having at least 95% identity with the amino acid sequence of residues 1 to 107 of SEQ ID NO: 8 provided that the VL CDR1 has the amino acid sequence of SEQ ID NO: 188, the VL CDR2 has the amino acid sequence of SEQ ID NO: 190, and the VL CDR3 has the amino acid sequence of SEQ ID NO: 192.

2. The humanized antibody of claim 1, in which the amino acid sequence of the VH binding domain comprises the amino acid sequence of residues 1 to 120 of SEQ ID NO: 50 or an amino acid sequence having at least 95% identity with the amino acid sequence of residues 1 to 120 of SEQ ID NO: 50 provided that the residue at position 72 is Arg or Lys and that the VH CDR1 has the amino acid sequence of SEQ ID NO: 96, the VH CDR2 has the amino acid sequence of SEQ ID NO: 98, and the VH CDR3 has the amino acid sequence of SEQ ID NO: 100.

3. The humanized antibody of claim 2, in which the amino acid sequence of the VH binding domain CDR2 comprises HIHFSGRPTYNPSLKS (SEQ ID NO: 136).

4. The humanized antibody of claim 2, in which the amino acid sequence of the VH binding domain comprises residues 1 to 120 of SEQ ID NO: 50.

5. The humanized antibody of claim 1, in which the amino acid sequence of the VH binding domain comprises the amino acid sequence of residues 1 to 120 of SEQ ID NO: 38 or an amino acid sequence having at least 95% identity with the amino acid sequence of residues 1 to 120 of SEQ ID NO: 38 provided that the residue at position 72 is Arg or Lys and that the VH CDR1 has the amino acid sequence of SEQ ID NO: 96, the VH CDR2 has the amino acid sequence of SEQ ID NO: 98, and the VH CDR3 has the amino acid sequence of SEQ ID NO: 100.

6. The humanized antibody of claim 5, in which the amino acid sequence of the binding domain VH CDR2 comprises HIHFSGRPTYNPSLKS (SEQ ID NO: 136).

7. The humanized antibody of claim 5, in which the amino acid sequence of the VH binding domain comprises residues 1 to 120 of SEQ ID NO: 38.

8. The humanized antibody of claim 2, in which the VH binding domain further comprises a constant domain.

9. The humanized antibody of claim 8, in which the constant domain has the amino acid sequence:

(SEQ ID NO: 52)
ASTKNPDVFPLAPSSKSTSGGTAALGCLVKDYFPEPVTVSWNSGALTSGVHTFPAVLQSSGLYSLSSV

VTVPSSSLGTQTYICNVNHKPSNTKVDKKVEPKSCDKTHTCPPCPAPELLGGPSVFLFPPKPKDTLMISRTPEV

TCVVVDVSHEDPEVKFNWYVDGVEVHNAKTKPREEQYNSTYRVVSVLTVLHQDWLNGKEYKCKVSNKALP

APIEKTISKAKGQPREPQVYTLPPSRDELTKNQVSLTCLVKGFYPSDIAVEWESNGQPENNYKTTPPVLDSDGS

FFLYSKLTVDKSRWQQGNVFSCSVMHEALHNHYTQKSLSLSPGK;
or (SEQ ID NO: 92)
ASTKGPSVFPLAPSSKSTSGGTAALGCLVKDYFPEPVTVSWNSGALTSGVHTFPAVLQSSGLYSLSSV

VTVPSSSLGTQTYICNVNHKPSNTKVDKKVEPKSCDKTHTCPPCPAPELLGGPSVFLFPPKPKDTLMISRTPEV

TCVVVDVSHEDPEVKFNWYVDGVEVHNAKTKPREEQYNSTYRVVSVLTVLHQDWLNGKEYKCKVSNKALP

APIEKTISKAKGQPREPQVYTLPPSRDELTKNQVSLTCLVKGFYPSDIAVEWESNGQPENNYKTTPPVLDSDGS

FFLYSKLTVDKSRWQQGNVFSCSVMHEALHNHYTQKSLSLSPGK;
or (SEQ ID NO: 53)
ASTKNPDVFPLAPSSKSTSGGTAALGCLVKDYFPEPVTVSWNSGALTSGVHTFPAVLQSSGLYSLSSV

VTVPSSSLGTQTYICNVNHKPSNTKVDKKVEPKSCDKTHTCPPCPAPELLGGPDVFLFPPKPKDTLMISRTPEV

TCVVVDVSHEDPEVKFNWYVDGVEVHNAKTKPREEQYNATYRVVSVLTVLHQDWLNGKEYKCKVSNKALP

APEEKTISKAKGQPREPQVYTLPPSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGK.

10. The humanized antibody of claim 5, in which the VH binding domain further comprises a constant domain.

11. The humanized antibody of claim 10, in which the constant domain has the amino acid sequence:

(SEQ ID NO: 52)
ASTKNPDVFPLAPSSKSTSGGTAALGCLVKDYFPEPVTVSWNSGALTSGVHTFPAVLQSSGLYSLSSV

VTVPSSSLGTQTYICNVNHKPSNTKVDKKVEPKSCDKTHTCPPCPAPELLGGPSVFLFPPKPKDTLMISRTPEV

TCVVVDVSHEDPEVKFNWYVDGVEVHNAKTKPREEQYNSTYRVVSVLTVLHQDWLNGKEYKCKVSNKALP

APIEKTISKAKGQPREPQVYTLPPSRDELTKNQVSLTCLVKGFYPSDIAVEWESNGQPENNYKTTPPVLDSDGS

FFLYSKLTVDKSRWQQGNVFSCSVMHEALHNHYTQKSLSLSPGK;
or (SEQ ID NO: 92)
ASTKGPSVFPLAPSSKSTSGGTAALGCLVKDYFPEPVTVSWNSGALTSGVHTFPAVLQSSGLYSLSSV

VTVPSSSLGTQTYICNVNHKPSNTKVDKKVEPKSCDKTHTCPPCPAPELLGGPSVFLFPPKPKDTLMISRTPEV

TCVVVDVSHEDPEVKFNWYVDGVEVHNAKTKPREEQYNSTYRVVSVLTVLHQDWLNGKEYKCKVSNKALP

APIEKTISKAKGQPREPQVYTLPPSRDELTKNQVSLTCLVKGFYPSDIAVEWESNGQPENNYKTTPPVLDSDGS

FFLYSKLTVDKSRWQQGNVFSCSVMHEALHNHYTQKSLSLSPGK;
or (SEQ ID NO: 53)
ASTKNPDVFPLAPSSKSTSGGTAALGCLVKDYFPEPVTVSWNSGALTSGVHTFPAVLQSSGLYSLSSV

VTVPSSSLGTQTYICNVNHKPSNTKVDKKVEPKSCDKTHTCPPCPAPELLGGPDVFLFPPKPKDTLMISRTPEV

TCVVVDVSHEDPEVKFNWYVDGVEVHNAKTKPREEQYNATYRVVSVLTVLHQDWLNGKEYKCKVSNKALP

APEEKTISKAKGQPREPQVYTLPPSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGK.

12. The humanized antibody of claim 2, in which the amino acid sequence of the VL binding domain comprises the amino acid sequence of residues 1 to 107 of SEQ ID NO: 7 or an amino acid sequence having at least 95% identity with the amino acid sequence of residues 1 to 107 of SEQ ID NO: 7 provided that the VL CDR1 has the amino acid sequence of SEQ ID NO: 188, the VL CDR2 has the amino acid sequence of SEQ ID NO: 190, and the VL CDR3 has the amino acid sequence of SEQ ID NO: 192.

13. The humanized antibody of claim 12, in which the amino acid sequence of the VL binding domain comprises residues 1 to 107 of SEQ ID NO: 7.

14. The humanized antibody of claim 5, in which the amino acid sequence of the VL binding domain comprises the amino acid sequence of residues 1 to 107 of SEQ ID NO: 8 or an amino acid sequence having at least 95% identity with the amino acid sequence of residues 1 to 107 of SEQ ID NO: 8 provided that the VL CDR1 has the amino acid sequence of SEQ ID NO: 188, the VL CDR2 has the amino acid sequence of SEQ ID NO: 190, and the VL CDR3 has the amino acid sequence of SEQ ID NO: 192.

15. The humanized antibody of claim 14, in which the amino acid sequence of the VL binding domain comprises residues 1 to 107 of SEQ ID NO: 8.

16. The humanized antibody of claim 12, in which the VL binding domain further comprises a constant domain.

17. The humanized antibody of claim 16, in which the constant domain has the amino acid sequence:

(SEQ ID NO: 93)
TVAAPSVFIFPPSDEQLKSGTASVVCLLNNFYPREAKVQWKVDNALQSGNSQESVTEQDSKDSTYSL

SSTLTLSKADYEKHKVYACEVTHQGLSSPVTKSFNRGEC.

18. The humanized antibody of claim 14, in which the VL binding domain further comprises a constant domain.

19. The humanized antibody of claim 18, in which the constant domain has the amino acid sequence:

```
                                                  (SEQ ID NO: 93)
TVAAPSVFIFPPSDEQLKSGTASVVCLLNNFYPREAKVQWKVDNALQSGNSQESVTEQDSKDSTYSL

SSTLTLSKADYEKHKVYACEVTHQGLSSPVTKSFNRGEC.
```

20. A humanized antibody, comprising a light chain comprising the amino acid sequence of SEQ ID NO: 7 and a heavy chain comprising the amino acid sequence of SEQ ID NO:50.

21. A humanized antibody, comprising a light chain comprising the amino acid sequence of SEQ ID NO: 8 and a heavy chain comprising the amino acid sequence of SEQ ID NO:38.

22. The humanized antibody of claim 1, in which the antibody has a reduced level of fucose.

23. The humanized antibody of claim 20, in which the antibody has a reduced level of fucose.

24. The humanized antibody of claim 21, in which the antibody has a reduced level of fucose.

25. A pharmaceutical preparation, comprising the humanized antibody of claim 1 and a pharmaceutically acceptable carrier.

26. A pharmaceutical preparation, comprising the humanized antibody of claim 20 and a pharmaceutically acceptable carrier.

27. A pharmaceutical preparation, comprising the humanized antibody of claim 21 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 8,901,279 B2 | Page 1 of 1 |
| APPLICATION NO. | : 13/898666 | |
| DATED | : December 2, 2014 | |
| INVENTOR(S) | : Adam W. Clarke et al. | |

It is certified that error appears in the above-identified patent and that said Letters Patent is hereby corrected as shown below:

On the Title page:

Item (60) of Related U.S. Application Data should read:

(60) Provisional application No. 61/160,682 filed on Mar. 16, 2009, provisional application No. 61/258,517, filed on Nov. 5, 2009.

In the Specification:

In Column 1, lines 7-15

The Cross Reference to Related Applications section should read:

This application is a continuation of U.S. Application No. 12/725,192, which was filed on Mar. 16, 2010 and issued as U.S. Patent No. 8,470,320 on June 25, 2013, is associated with and claims priority from to Australian patent application no. Patent Application No. 2009901129 filed on Mar. 16, 2009, and U.S. patent application Provisional Application No. 61/160,682 filed on Mar. 16, 2009, and U.S. patent application Provisional Application No. 61/258,517 filed on Nov. 5, 2009, the entire contents of each of these applications is incorporated herein by reference.

Signed and Sealed this
Tenth Day of March, 2015

Michelle K. Lee
*Deputy Director of the United States Patent and Trademark Office*

SEQUENCE LISTING

```
<160> NUMBER OF SEQ ID NOS: 225

<210> SEQ ID NO 1
<211> LENGTH: 120
<212> TYPE: PRT
<213> ORGANISM: Mus musculus

<400> SEQUENCE: 1

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Val Arg Gln Phe Pro Gly Asn Lys Met Glu Trp
        35                  40                  45

Met Gly His Ile His Phe Ser Gly Arg Pro Thr Tyr Asn Pro Ser Leu
    50                  55                  60

Ser Ser Arg Ile Ser Ile Thr Arg Asp Thr Ser Lys Asn Gln Phe Leu
65                  70                  75                  80

Leu Gln Leu Lys Phe Val Thr Thr Glu Asp Thr Ser Thr Tyr Phe Cys
                85                  90                  95

Ala Arg Lys Gly Lys Gly Ser Asp Asp Gly Leu Asn Tyr Trp Gly Gln
            100                 105                 110
```

```
Gly Ile Ser Val Thr Val Ser Ser
        115                 120
```

```
<210> SEQ ID NO 2
<211> LENGTH: 450
<212> TYPE: PRT
<213> ORGANISM: Artificial Sequence
<220> FEATURE:
<223> OTHER INFORMATION: Antibody

<400> SEQUENCE: 2

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Val Arg Gln Phe Pro Gly Asn Lys Met Glu Trp
        35                  40                  45

Met Gly His Ile His Phe Ser Gly Arg Pro Thr Tyr Asn Pro Ser Leu
    50                  55                  60

Ser Ser Arg Ile Ser Ile Thr Arg Asp Thr Ser Lys Asn Gln Phe Leu
65                  70                  75                  80

Leu Gln Leu Lys Phe Val Thr Thr Glu Asp Thr Ser Thr Tyr Phe Cys
                85                  90                  95

Ala Arg Lys Gly Lys Gly Ser Asp Asp Gly Leu Asn Tyr Trp Gly Gln
            100                 105                 110

Gly Ile Ser Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350
```

```
Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 3
<211> LENGTH: 107
<212> TYPE: PRT
<213> ORGANISM: Mus musculus

<400> SEQUENCE: 3

Glu Asn Val Leu Thr Gln Ser Pro Val Ile Met Ser Ala Ser Pro Gly
1               5                   10                  15

Glu Lys Val Thr Met Thr Cys Ser Ala Ser Ser Ser Leu Ser Tyr Ile
            20                  25                  30

His Trp Tyr Gln Gln Lys Ser Arg Thr Ser Pro Lys Leu Trp Ile Tyr
        35                  40                  45

Asp Thr Ser Asn Leu Ala Ser Gly Val Pro Gly Arg Phe Ser Gly Ser
    50                  55                  60

Gly Ser Gly Asn Ser Tyr Ser Leu Thr Ile Ser Ser Met Glu Ala Glu
65                  70                  75                  80

Asp Val Ala Thr Tyr Tyr Cys Phe Gln Gly Ser Glu Tyr Pro Leu Thr
                85                  90                  95

Phe Gly Gly Gly Thr Lys Leu Glu Met Thr Arg
            100                 105

<210> SEQ ID NO 4
<211> LENGTH: 213
<212> TYPE: PRT
<213> ORGANISM: Artificial Sequence
<220> FEATURE:
<223> OTHER INFORMATION: Antibody

<400> SEQUENCE: 4

Glu Asn Val Leu Thr Gln Ser Pro Val Ile Met Ser Ala Ser Pro Gly
1               5                   10                  15

Glu Lys Val Thr Met Thr Cys Ser Ala Ser Ser Ser Leu Ser Tyr Ile
            20                  25                  30

His Trp Tyr Gln Gln Lys Ser Arg Thr Ser Pro Lys Leu Trp Ile Tyr
        35                  40                  45

Asp Thr Ser Asn Leu Ala Ser Gly Val Pro Gly Arg Phe Ser Gly Ser
    50                  55                  60

Gly Ser Gly Asn Ser Tyr Ser Leu Thr Ile Ser Ser Met Glu Ala Glu
65                  70                  75                  80

Asp Val Ala Thr Tyr Tyr Cys Phe Gln Gly Ser Glu Tyr Pro Leu Thr
                85                  90                  95

Phe Gly Gly Gly Thr Lys Leu Glu Met Thr Arg Thr Val Ala Ala Pro
```

```
                    100                 105                 110
Ser Val Phe Ile Phe Pro Pro Ser Asp Glu Gln Leu Lys Ser Gly Thr
                115                 120                 125

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
                195                 200                 205

Asn Arg Gly Glu Cys
    210

<210> SEQ ID NO 5
<211> LENGTH: 19
<212> TYPE: PRT
<213> ORGANISM: Artificial Sequence
<220> FEATURE:
<223> OTHER INFORMATION: Antibody

<400> SEQUENCE: 5

Met Glu Trp Ser Trp Val Phe Leu Phe Phe Leu Ser Val Thr Thr Gly
1               5                   10                  15

Val His Ser

<210> SEQ ID NO 6
<211> LENGTH: 20
<212> TYPE: PRT
<213> ORGANISM: Artificial Sequence
<220> FEATURE:
<223> OTHER INFORMATION: Antibody

<400> SEQUENCE: 6

Met Ser Val Pro Thr Gln Val Leu Gly Leu Leu Leu Leu Trp Leu Thr
1               5                   10                  15

Asp Ala Arg Cys
            20

<210> SEQ ID NO 7
<211> LENGTH: 213
<212> TYPE: PRT
<213> ORGANISM: Artificial Sequence
<220> FEATURE:
<223> OTHER INFORMATION: Antibody

<400> SEQUENCE: 7

Glu Ile Val Leu Thr Gln Ser Pro Gly Thr Leu Ser Leu Ser Pro Gly
1               5                   10                  15

Glu Arg Ala Thr Leu Ser Cys Ser Ala Ser Ser Ser Leu Ser Tyr Ile
            20                  25                  30

His Trp Tyr Gln Gln Lys Pro Gly Gln Ala Pro Arg Leu Leu Ile Tyr
        35                  40                  45

Asp Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Val Glu Pro Glu
65                  70                  75                  80
```

```
Asp Phe Ala Val Tyr Tyr Cys Phe Gln Gly Ser Glu Tyr Pro Leu Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 8
<211> LENGTH: 213
<212> TYPE: PRT
<213> ORGANISM: Artificial Sequence
<220> FEATURE:
<223> OTHER INFORMATION: Antibody

<400> SEQUENCE: 8

```
Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Leu Ser Tyr Ile
            20                  25                  30

His Trp Tyr Gln Gln Lys Pro Gly Gln Ala Pro Arg Leu Leu Ile Tyr
        35                  40                  45

Asp Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Phe Gln Gly Ser Glu Tyr Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

```
<210> SEQ ID NO 9
<211> LENGTH: 450
<212> TYPE: PRT
<213> ORGANISM: Artificial Sequence
<220> FEATURE:
<223> OTHER INFORMATION: Antibody

<400> SEQUENCE: 9

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Tyr Ser Trp His Trp Ile Arg Gln Ser Pro Gly Lys Gly Leu Gln Trp
        35                  40                  45

Ile Gly His Ile His Phe Ser Gly Arg Pro Thr Tyr Asn Pro Ser Leu
    50                  55                  60

Ser Ser Arg Val Thr Ile Ser Val Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365
```

```
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
            435                 440                 445
Gly Lys
    450

<210> SEQ ID NO 10
<211> LENGTH: 450
<212> TYPE: PRT
<213> ORGANISM: Artificial Sequence
<220> FEATURE:
<223> OTHER INFORMATION: Antibody

<400> SEQUENCE: 10

Glu Val Gln Leu Gln Gln Trp Gly Ala Gly Leu Leu Lys Pro Ser Glu
1               5                   10                  15
Thr Leu Ser Leu Thr Cys Ala Val Tyr Gly Gly Ser Phe Ser Ser Gly
            20                  25                  30
Tyr Ser Trp His Trp Ile Arg Gln Pro Pro Gly Lys Gly Leu Glu Trp
        35                  40                  45
Ile Gly His Ile His Phe Ser Gly Arg Pro Thr Tyr Asn Pro Ser Leu
    50                  55                  60
Ser Ser Arg Val Thr Ile Ser Val Asp Thr Ser Lys Asn Gln Phe Ser
65                  70                  75                  80
Leu Lys Leu Ser Ser Val Thr Ala Ala Asp Thr Ala Val Tyr Tyr Cys
                85                  90                  95
Ala Arg Lys Gly Lys Gly Ser Asp Asp Gly Leu Asn Tyr Trp Gly Gln
                100                 105                 110
Gly Thr Leu Val Thr Val Ser Ser Ala Ser Thr Lys Asn Pro Asp Val
            115                 120                 125
Phe Pro Leu Ala Pro Ser Ser Lys Ser Thr Ser Gly Gly Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
```

-continued

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 11
<211> LENGTH: 450
<212> TYPE: PRT
<213> ORGANISM: Artificial Sequence
<220> FEATURE:
<223> OTHER INFORMATION: Antibody

<400> SEQUENCE: 11

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln Ser Pro Gly Lys Gly Leu Gln Trp
        35                  40                  45

Ile Gly His Ile His Phe Ser Gly Arg Pro Thr Tyr Asn Pro Ser Leu
    50                  55                  60

Ser Ser Arg Val Thr Ile Ser Val Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

```
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
            210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
            245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
            290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
            325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
Gly Lys
    450

<210> SEQ ID NO 12
<211> LENGTH: 450
<212> TYPE: PRT
<213> ORGANISM: Artificial Sequence
<220> FEATURE:
<223> OTHER INFORMATION: Antibody

<400> SEQUENCE: 12

Glu Val Gln Leu Gln Gln Trp Gly Ala Gly Leu Leu Lys Pro Ser Glu
1               5                   10                  15
Thr Leu Ser Leu Thr Cys Ala Val Tyr Gly Tyr Ser Ile Thr Ser Gly
            20                  25                  30
Tyr Ser Trp His Trp Ile Arg Gln Pro Pro Gly Lys Gly Leu Glu Trp
            35                  40                  45
Ile Gly His Ile His Phe Ser Gly Arg Pro Thr Tyr Asn Pro Ser Leu
            50                  55                  60
Ser Ser Arg Val Thr Ile Ser Val Asp Thr Ser Lys Asn Gln Phe Ser
65                  70                  75                  80
```

Leu Lys Leu Ser Ser Val Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 13
<211> LENGTH: 450
<212> TYPE: PRT
<213> ORGANISM: Artificial Sequence
<220> FEATURE:
<223> OTHER INFORMATION: Antibody

<400> SEQUENCE: 13

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln Ser Pro Gly Lys Gly Leu Glu Trp
            35                  40                  45

Met Gly His Ile His Phe Ser Gly Arg Pro Thr Tyr Asn Pro Ser Leu
    50                  55                  60

Ser Ser Arg Ile Ser Ile Ser Arg Asp Thr Ala Lys Asn Gln Phe Ser
65              70                  75                  80

Leu Lys Leu Thr Ser Met Thr Ala Ala Asp Thr Ala Val Tyr Tyr Cys
            85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
```

```
                    405                 410                 415
Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 14
<211> LENGTH: 450
<212> TYPE: PRT
<213> ORGANISM: Artificial Sequence
<220> FEATURE:
<223> OTHER INFORMATION: Antibody

<400> SEQUENCE: 14

Glu Val Gln Leu Gln Glu Ser Gly Pro Gly Leu Val Lys Pro Ser Glu
1               5                   10                  15

Thr Leu Ser Leu Thr Cys Thr Val Thr Gly Tyr Ser Ile Thr Ser Gly
            20                  25                  30

Tyr Ser Trp His Trp Ile Arg Gln Ser Pro Gly Lys Gly Leu Glu Trp
        35                  40                  45

Met Gly His Ile His Phe Ser Gly Arg Pro Thr Tyr Asn Pro Ser Leu
    50                  55                  60

Ser Ser Arg Ile Ser Ile Ser Arg Asp Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
```

```
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Asp Glu Leu Thr Lys Asn Gln Val Ser Leu
                355                 360                 365
Thr Cys Leu Val Lys Gly Phe Tyr Pro Ser Asp Ile Ala Val Glu Trp
                370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly Lys
    450

<210> SEQ ID NO 15
<211> LENGTH: 450
<212> TYPE: PRT
<213> ORGANISM: Artificial Sequence
<220> FEATURE:
<223> OTHER INFORMATION: Antibody

<400> SEQUENCE: 15

Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Gly
                20                  25                  30
Tyr Ser Trp His Trp Ile Arg Gln Ser Pro Gly Lys Gly Leu Glu Trp
                35                  40                  45
Met Gly His Ile His Phe Ser Gly Arg Pro Thr Tyr Asn Pro Ser Leu
50                  55                  60
Ser Ser Arg Ile Ser Ile Ser Arg Asp Thr Ala Lys Asn Gln Phe Ser
65                  70                  75                  80
Leu Lys Leu Thr Ser Met Thr Ala Ala Asp Thr Ala Val Tyr Tyr Cys
                85                  90                  95
Ala Arg Lys Gly Lys Gly Ser Asp Asp Gly Leu Asn Tyr Trp Gly Gln
                100                 105                 110
Gly Thr Leu Val Thr Val Ser Ser Ala Ser Thr Lys Asn Pro Asp Val
                115                 120                 125
Phe Pro Leu Ala Pro Ser Ser Lys Ser Thr Ser Gly Gly Thr Ala Ala
                130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Lys Val Glu Pro Lys Ser Cys Asp
```

```
                210               215               220
Lys Thr His Thr Cys Pro Pro Cys Pro Ala Pro Glu Leu Leu Gly Gly
225               230               235               240

Pro Ser Val Phe Leu Phe Pro Pro Lys Pro Lys Asp Thr Leu Met Ile
                245               250               255

Ser Arg Thr Pro Glu Val Thr Cys Val Val Val Asp Val Ser His Glu
            260               265               270

Asp Pro Glu Val Lys Phe Asn Trp Tyr Val Asp Gly Val Glu Val His
        275               280               285

Asn Ala Lys Thr Lys Pro Arg Glu Glu Gln Tyr Asn Ser Thr Tyr Arg
    290               295               300

Val Val Ser Val Leu Thr Val Leu His Gln Asp Trp Leu Asn Gly Lys
305               310               315               320

Glu Tyr Lys Cys Lys Val Ser Asn Lys Ala Leu Pro Ala Pro Ile Glu
                325               330               335

Lys Thr Ile Ser Lys Ala Lys Gly Gln Pro Arg Glu Pro Gln Val Tyr
            340               345               350

Thr Leu Pro Pro Ser Arg Asp Glu Leu Thr Lys Asn Gln Val Ser Leu
        355               360               365

Thr Cys Leu Val Lys Gly Phe Tyr Pro Ser Asp Ile Ala Val Glu Trp
    370               375               380

Glu Ser Asn Gly Gln Pro Glu Asn Asn Tyr Lys Thr Thr Pro Pro Val
385               390               395               400

Leu Asp Ser Asp Gly Ser Phe Phe Leu Tyr Ser Lys Leu Thr Val Asp
                405               410               415

Lys Ser Arg Trp Gln Gln Gly Asn Val Phe Ser Cys Ser Val Met His
            420               425               430

Glu Ala Leu His Asn His Tyr Thr Gln Lys Ser Leu Ser Leu Ser Pro
        435               440               445

Gly Lys
    450

<210> SEQ ID NO 16
<211> LENGTH: 213
<212> TYPE: PRT
<213> ORGANISM: Artificial Sequence
<220> FEATURE:
<223> OTHER INFORMATION: Antibody

<400> SEQUENCE: 16

Glu Asn Val Leu Thr Gln Ser Pro Gly Thr Leu Ser Leu Ser Pro Gly
1               5                   10                  15

Glu Arg Ala Thr Leu Ser Cys Ser Ala Ser Ser Ser Leu Ser Tyr Ile
            20                  25                  30

His Trp Tyr Gln Gln Lys Pro Gly Gln Ala Pro Arg Leu Leu Ile Tyr
        35                  40                  45

Asp Thr Ser Asn Leu Ala Ser Gly Ile Pro Asp Arg Phe Ser Gly Ser
    50                  55                  60

Gly Ser Gly Asn Asp Phe Thr Leu Thr Ile Ser Arg Val Glu Pro Glu
65                  70                  75                  80

Asp Phe Ala Val Tyr Tyr Cys Phe Gln Gly Ser Glu Tyr Pro Leu Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
```

```
                 115                 120                 125
Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                        165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
                195                 200                 205

Asn Arg Gly Glu Cys
        210

<210> SEQ ID NO 17
<211> LENGTH: 450
<212> TYPE: PRT
<213> ORGANISM: Artificial Sequence
<220> FEATURE:
<223> OTHER INFORMATION: Antibody

<400> SEQUENCE: 17

Glu Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Ser Gly
            20                  25                  30

Tyr Ser Trp His Trp Ile Arg Gln Pro Pro Gly Lys Gly Leu Glu Trp
        35                  40                  45

Met Gly His Ile His Phe Ser Gly Arg Pro Thr Tyr Asn Pro Ser Leu
    50                  55                  60

Ser Ser Arg Ile Ser Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
```

```
            260                 265                 270
Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 18
<211> LENGTH: 213
<212> TYPE: PRT
<213> ORGANISM: Artificial Sequence
<220> FEATURE:
<223> OTHER INFORMATION: Antibody

<400> SEQUENCE: 18

Glu Asn Val Leu Thr Gln Ser Pro Ala Thr Leu Ser Leu Ser Pro Gly
1               5                   10                  15

Glu Arg Ala Thr Leu Ser Cys Ser Ala Ser Ser Ser Leu Ser Tyr Ile
            20                  25                  30

His Trp Tyr Gln Gln Lys Pro Gly Gln Ala Pro Arg Leu Leu Ile Tyr
        35                  40                  45

Asp Thr Ser Asn Leu Ala Ser Gly Ile Pro Asp Arg Phe Ser Gly Ser
    50                  55                  60

Gly Ser Gly Asn Asp Phe Thr Leu Thr Ile Ser Arg Leu Glu Pro Glu
65                  70                  75                  80

Asp Phe Ala Val Tyr Tyr Cys Phe Gln Gly Ser Glu Tyr Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
```

```
                165                 170                 175
Thr Leu Thr Leu Ser Lys Ala Asp Tyr Glu Lys His Lys Val Tyr Ala
        180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 19
<211> LENGTH: 450
<212> TYPE: PRT
<213> ORGANISM: Artificial Sequence
<220> FEATURE:
<223> OTHER INFORMATION: Antibody

<400> SEQUENCE: 19

Glu Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln Ser Pro Gly Lys Gly Leu Glu Trp
        35                  40                  45

Ile Gly His Ile His Phe Ser Gly Arg Pro Thr Tyr Asn Pro Ser Leu
    50                  55                  60

Ser Ser Arg Val Thr Ile Ser Val Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
```

-continued

```
                305                 310                 315                 320
        Glu Tyr Lys Cys Lys Val Ser Asn Lys Ala Leu Pro Ala Pro Ile Glu
                        325                 330                 335

Lys Thr Ile Ser Lys Ala Lys Gly Gln Pro Arg Glu Pro Gln Val Tyr
                    340                 345                 350

Thr Leu Pro Pro Ser Arg Asp Glu Leu Thr Lys Asn Gln Val Ser Leu
                    355                 360                 365

Thr Cys Leu Val Lys Gly Phe Tyr Pro Ser Asp Ile Ala Val Glu Trp
                    370                 375                 380

Glu Ser Asn Gly Gln Pro Glu Asn Asn Tyr Lys Thr Thr Pro Pro Val
        385                 390                 395                 400

Leu Asp Ser Asp Gly Ser Phe Phe Leu Tyr Ser Lys Leu Thr Val Asp
                        405                 410                 415

Lys Ser Arg Trp Gln Gln Gly Asn Val Phe Ser Cys Ser Val Met His
                        420                 425                 430

Glu Ala Leu His Asn His Tyr Thr Gln Lys Ser Leu Ser Leu Ser Pro
                        435                 440                 445

Gly Lys
            450

<210> SEQ ID NO 20
<211> LENGTH: 450
<212> TYPE: PRT
<213> ORGANISM: Artificial Sequence
<220> FEATURE:
<223> OTHER INFORMATION: Antibody

<400> SEQUENCE: 20

Glu Val Gln Leu Gln Glu Ser Gly Pro Gly Leu Val Lys Pro Ser Glu
        1               5                   10                  15

Thr Leu Ser Leu Thr Cys Thr Val Ser Gly Tyr Ser Ile Thr Ser Gly
                    20                  25                  30

Tyr Ser Trp His Trp Ile Arg Gln Ser Pro Gly Lys Gly Leu Gln Trp
                    35                  40                  45

Met Gly His Ile His Phe Ser Gly Arg Pro Thr Tyr Asn Pro Ser Leu
                50                  55                  60

Ser Ser Arg Val Thr Ile Ser Val Glu Thr Ala Lys Asn Gln Phe Ser
        65                  70                  75                  80

Leu Lys Leu Thr Ser Met Thr Ala Ala Asp Thr Ala Val Tyr Tyr Cys
                        85                  90                  95

Ala Arg Lys Gly Lys Gly Ser Asp Asp Gly Leu Asn Tyr Trp Gly Gln
                    100                 105                 110

Gly Thr Leu Val Thr Val Ser Ser Ala Ser Thr Lys Asn Pro Asp Val
                    115                 120                 125

Phe Pro Leu Ala Pro Ser Ser Lys Ser Thr Ser Gly Gly Thr Ala Ala
                    130                 135                 140

Leu Gly Cys Leu Val Lys Asp Tyr Phe Pro Glu Pro Val Thr Val Ser
        145                 150                 155                 160

Trp Asn Ser Gly Ala Leu Thr Ser Gly Val His Thr Phe Pro Ala Val
                        165                 170                 175

Leu Gln Ser Ser Gly Leu Tyr Ser Leu Ser Ser Val Val Thr Val Pro
                        180                 185                 190

Ser Ser Ser Leu Gly Thr Gln Thr Tyr Ile Cys Asn Val Asn His Lys
                    195                 200                 205

Pro Ser Asn Thr Lys Val Asp Lys Lys Val Glu Pro Lys Ser Cys Asp
```

```
            210                 215                 220
Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 21
<211> LENGTH: 450
<212> TYPE: PRT
<213> ORGANISM: Artificial Sequence
<220> FEATURE:
<223> OTHER INFORMATION: Antibody

<400> SEQUENCE: 21

Glu Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln Ser Pro Gly Lys Gly Leu Gln Trp
        35                  40                  45

Ile Gly His Ile His Phe Ser Gly Arg Pro Thr Tyr Asn Pro Ser Leu
    50                  55                  60

Ser Ser Arg Ile Thr Ile Ser Val Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
```

```
            115                 120                 125
Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 22
<211> LENGTH: 450
<212> TYPE: PRT
<213> ORGANISM: Artificial Sequence
<220> FEATURE:
<223> OTHER INFORMATION: Antibody

<400> SEQUENCE: 22

Glu Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Gly
```

```
                    20                  25                  30
Tyr Ser Trp His Trp Ile Arg Gln Ser Pro Lys Gly Leu Gln Trp
                35                  40                  45
Ile Gly His Ile His Phe Ser Gly Arg Pro Thr Tyr Asn Pro Ser Leu
            50                  55                  60
Ser Ser Arg Val Ser Ile Ser Val Glu Thr Ala Lys Asn Gln Phe Ser
65                  70                  75                  80
Leu Lys Leu Thr Ser Met Thr Ala Ala Asp Thr Ala Val Tyr Tyr Cys
                85                  90                  95
Ala Arg Lys Gly Lys Gly Ser Asp Asp Gly Leu Asn Tyr Trp Gly Gln
            100                 105                 110
Gly Thr Leu Val Thr Val Ser Ala Ser Thr Lys Asn Pro Asp Val
            115                 120                 125
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
            210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
            290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
```

```
Gly Lys
    450

<210> SEQ ID NO 23
<211> LENGTH: 450
<212> TYPE: PRT
<213> ORGANISM: Artificial Sequence
<220> FEATURE:
<223> OTHER INFORMATION: Antibody

<400> SEQUENCE: 23

Glu Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln Ser Pro Gly Lys Gly Leu Gln Trp
        35                  40                  45

Ile Gly His Ile His Phe Ser Gly Arg Pro Thr Tyr Asn Pro Ser Leu
    50                  55                  60

Ser Ser Arg Val Thr Ile Ser Arg Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350
```

```
Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 24
<211> LENGTH: 450
<212> TYPE: PRT
<213> ORGANISM: Artificial Sequence
<220> FEATURE:
<223> OTHER INFORMATION: Antibody

<400> SEQUENCE: 24

Glu Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln Ser Pro Gly Lys Gly Leu Gln Trp
        35                  40                  45

Ile Gly His Ile His Phe Ser Gly Arg Pro Thr Tyr Asn Pro Ser Leu
    50                  55                  60

Ser Ser Arg Val Thr Ile Ser Val Asp Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 25
<211> LENGTH: 450
<212> TYPE: PRT
<213> ORGANISM: Artificial Sequence
<220> FEATURE:
<223> OTHER INFORMATION: Antibody

<400> SEQUENCE: 25

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln Ser Pro Gly Lys Gly Leu Gln Trp
        35                  40                  45

Ile Gly His Ile His Phe Ser Gly Arg Pro Thr Tyr Asn Pro Ser Leu
    50                  55                  60

Ser Ser Arg Val Thr Ile Ser Arg Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 26
<211> LENGTH: 450
<212> TYPE: PRT
<213> ORGANISM: Artificial Sequence
<220> FEATURE:
<223> OTHER INFORMATION: Antibody

<400> SEQUENCE: 26

Glu Val Gln Leu Gln Gln Trp Gly Ala Gly Leu Leu Lys Pro Ser Glu
1               5                   10                  15

Thr Leu Ser Leu Thr Cys Ala Val Tyr Gly Tyr Ser Ile Thr Ser Gly
            20                  25                  30

Tyr Ser Trp His Trp Ile Arg Gln Pro Pro Gly Lys Gly Leu Glu Trp
        35                  40                  45

Ile Gly His Ile His Phe Ser Gly Arg Pro Thr Tyr Asn Pro Ser Leu
    50                  55                  60

Ser Ser Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 27
<211> LENGTH: 450

<212> TYPE: PRT
<213> ORGANISM: Artificial Sequence
<220> FEATURE:
<223> OTHER INFORMATION: Antibody

<400> SEQUENCE: 27

```
Glu Val Gln Leu Gln Gln Trp Gly Ala Gly Leu Leu Lys Pro Ser Glu
1               5                   10                  15
Thr Leu Ser Leu Thr Cys Ala Val Tyr Gly Gly Ser Phe Ser Ser Gly
            20                  25                  30
Tyr Ser Trp His Trp Ile Arg Gln Pro Pro Gly Lys Gly Leu Glu Trp
        35                  40                  45
Ile Gly His Ile His Phe Ser Gly Arg Pro Thr Tyr Asn Pro Ser Leu
    50                  55                  60
Ser Ser Arg Val Thr Ile Ser Arg Asp Thr Ser Lys Asn Gln Phe Ser
65                  70                  75                  80
Leu Lys Leu Ser Ser Val Thr Ala Ala Asp Thr Ala Val Tyr Tyr Cys
                85                  90                  95
Ala Arg Lys Gly Lys Gly Ser Asp Asp Gly Leu Asn Tyr Trp Gly Gln
            100                 105                 110
Gly Thr Leu Val Thr Val Ser Ser Ala Ser Thr Lys Asn Pro Asp Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
```

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 28
<211> LENGTH: 450
<212> TYPE: PRT
<213> ORGANISM: Artificial Sequence
<220> FEATURE:
<223> OTHER INFORMATION: Antibody

<400> SEQUENCE: 28

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Tyr Ser Trp His Trp Ile Arg Gln Ser Pro Gly Lys Gly Leu Gln Trp
        35                  40                  45

Ile Gly His Ile His Phe Ser Gly Arg Pro Thr Tyr Asn Pro Ser Leu
    50                  55                  60

Ser Ser Arg Val Thr Ile Ser Arg Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285
```

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 29
<211> LENGTH: 450
<212> TYPE: PRT
<213> ORGANISM: Artificial Sequence
<220> FEATURE:
<223> OTHER INFORMATION: Antibody

<400> SEQUENCE: 29

Glu Val Gln Leu Gln Gln Trp Gly Ala Gly Leu Leu Lys Pro Ser Glu
1               5                   10                  15

Thr Leu Ser Leu Thr Cys Ala Val Tyr Gly Tyr Ser Phe Ser Ser Gly
            20                  25                  30

Tyr Ser Trp His Trp Ile Arg Gln Pro Pro Gly Lys Gly Leu Glu Trp
        35                  40                  45

Ile Gly His Ile His Phe Ser Gly Arg Pro Thr Tyr Asn Pro Ser Leu
    50                  55                  60

Ser Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

```
Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 30
<211> LENGTH: 450
<212> TYPE: PRT
<213> ORGANISM: Artificial Sequence
<220> FEATURE:
<223> OTHER INFORMATION: Antibody

<400> SEQUENCE: 30

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Val Arg Gln Phe Pro Gly Asn Lys Met Glu Trp
        35                  40                  45

Met Gly His Ile His Trp Ser Gly Arg Pro Thr Tyr Asn Pro Ser Leu
    50                  55                  60

Ser Ser Arg Ile Ser Ile Thr Arg Asp Thr Ser Lys Asn Gln Phe Leu
65                  70                  75                  80

Leu Gln Leu Lys Phe Val Thr Thr Glu Asp Thr Ser Thr Tyr Phe Cys
                85                  90                  95
```

Ala Arg Lys Gly Lys Gly Ser Asp Gly Leu Asn Tyr Trp Gly Gln
            100                 105                 110

Gly Ile Ser Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 31
<211> LENGTH: 450
<212> TYPE: PRT
<213> ORGANISM: Artificial Sequence
<220> FEATURE:
<223> OTHER INFORMATION: Antibody

<400> SEQUENCE: 31

-continued

```
Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Val Arg Gln Phe Pro Gly Asn Lys Met Glu Trp
        35                  40                  45

Met Gly His Ile His Tyr Ser Gly Arg Pro Thr Tyr Asn Pro Ser Leu
    50                  55                  60

Ser Ser Arg Ile Ser Ile Thr Arg Asp Thr Ser Lys Asn Gln Phe Leu
65                  70                  75                  80

Leu Gln Leu Lys Phe Val Thr Thr Glu Asp Thr Ser Thr Tyr Phe Cys
                85                  90                  95

Ala Arg Lys Gly Lys Gly Ser Asp Asp Gly Leu Asn Tyr Trp Gly Gln
            100                 105                 110

Gly Ile Ser Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
```

```
                420                 425                 430
Glu Ala Leu His Asn His Tyr Thr Gln Lys Ser Leu Ser Leu Ser Pro
            435                 440                 445
Gly Lys
    450

<210> SEQ ID NO 32
<211> LENGTH: 450
<212> TYPE: PRT
<213> ORGANISM: Artificial Sequence
<220> FEATURE:
<223> OTHER INFORMATION: Antibody

<400> SEQUENCE: 32

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Val Arg Gln Phe Pro Gly Asn Lys Met Glu Trp
        35                  40                  45

Met Gly His Ile His Pro Ser Gly Arg Pro Thr Tyr Asn Pro Ser Leu
    50                  55                  60

Ser Ser Arg Ile Ser Ile Thr Arg Asp Thr Ser Lys Asn Gln Phe Leu
65                  70                  75                  80

Leu Gln Leu Lys Phe Val Thr Thr Glu Asp Thr Ser Thr Tyr Phe Cys
                85                  90                  95

Ala Arg Lys Gly Lys Gly Ser Asp Asp Gly Leu Asn Tyr Trp Gly Gln
            100                 105                 110

Gly Ile Ser Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
```

```
                    325                 330                 335
Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 33
<211> LENGTH: 450
<212> TYPE: PRT
<213> ORGANISM: Artificial Sequence
<220> FEATURE:
<223> OTHER INFORMATION: Antibody

<400> SEQUENCE: 33

Glu Val Gln Leu Gln Gln Trp Gly Ala Gly Leu Leu Lys Pro Ser Glu
1               5                   10                  15

Thr Leu Ser Leu Thr Cys Ala Val Tyr Gly Tyr Ser Ile Thr Ser Gly
                20                  25                  30

Tyr Ser Trp His Trp Ile Arg Gln Pro Pro Gly Lys Gly Leu Glu Trp
            35                  40                  45

Ile Gly His Ile His Phe Ser Gly Arg Pro Thr Tyr Asn Pro Ser Leu
        50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
```

```
            225                 230                 235                 240
Pro Ser Val Phe Leu Phe Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 34
<211> LENGTH: 450
<212> TYPE: PRT
<213> ORGANISM: Artificial Sequence
<220> FEATURE:
<223> OTHER INFORMATION: Antibody

<400> SEQUENCE: 34

Glu Val Gln Leu Gln Gln Trp Gly Ala Gly Leu Leu Lys Pro Ser Glu
1               5                   10                  15

Thr Leu Ser Leu Thr Cys Ala Val Tyr Gly Tyr Ser Ile Thr Ser Gly
                20                  25                  30

Tyr Ser Trp His Trp Ile Arg Gln Pro Pro Gly Lys Gly Leu Glu Trp
                35                  40                  45

Ile Gly His Ile His Phe Ser Gly Arg Pro Thr Tyr Asn Pro Ser Leu
50                  55                  60

Leu Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
                100                 105                 110

Gly Thr Leu Val Thr Val Ser Ser Ala Ser Thr Lys Asn Pro Asp Val
                115                 120                 125

Phe Pro Leu Ala Pro Ser Ser Lys Ser Thr Ser Gly Gly Thr Ala Ala
```

```
                130                 135                 140
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
                210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
                290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
450

<210> SEQ ID NO 35
<211> LENGTH: 450
<212> TYPE: PRT
<213> ORGANISM: Artificial Sequence
<220> FEATURE:
<223> OTHER INFORMATION: Antibody

<400> SEQUENCE: 35

Glu Val Gln Leu Gln Gln Trp Gly Ala Gly Leu Leu Lys Pro Ser Glu
1               5                   10                  15

Thr Leu Ser Leu Thr Cys Ala Val Tyr Gly Tyr Ser Ile Thr Ser Gly
                20                  25                  30

Tyr Ser Trp His Trp Ile Arg Gln Pro Pro Gly Lys Gly Leu Glu Trp
```

```
                35                  40                  45
Ile Gly His Ile His Phe Ser Gly Arg Pro Thr Tyr Asn Pro Ser Leu
 50                  55                  60

His Ser Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Lys Gly Lys Gly Ser Asp Asp Gly Leu Asn Tyr Trp Gly Gln
                100                 105                 110

Gly Thr Leu Val Thr Val Ser Ser Ala Ser Thr Lys Asn Pro Asp Val
                115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
 450
```

<210> SEQ ID NO 36
<211> LENGTH: 450
<212> TYPE: PRT
<213> ORGANISM: Artificial Sequence
<220> FEATURE:
<223> OTHER INFORMATION: Antibody

<400> SEQUENCE: 36

```
Glu Val Gln Leu Gln Gln Trp Gly Ala Gly Leu Leu Lys Pro Ser Glu
1               5                   10                  15

Thr Leu Ser Leu Thr Cys Ala Val Tyr Gly Tyr Ser Ile Thr Ser Gly
            20                  25                  30

Tyr Ser Trp His Trp Ile Arg Gln Pro Pro Gly Lys Gly Leu Glu Trp
        35                  40                  45

Ile Gly His Ile His Phe Ser Gly Arg Pro Thr Tyr Asn Pro Ser Leu
    50                  55                  60

Phe Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365
```

```
Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
        435                 440                 445

Gly Lys
    450

<210> SEQ ID NO 37
<211> LENGTH: 450
<212> TYPE: PRT
<213> ORGANISM: Artificial Sequence
<220> FEATURE:
<223> OTHER INFORMATION: Antibody

<400> SEQUENCE: 37

Glu Val Gln Leu Gln Gln Trp Gly Ala Gly Leu Leu Lys Pro Ser Glu
1               5                   10                  15

Thr Leu Ser Leu Thr Cys Ala Val Tyr Gly Tyr Ser Ile Thr Ser Gly
            20                  25                  30

Tyr Ser Trp His Trp Ile Arg Gln Pro Pro Gly Lys Gly Leu Glu Trp
        35                  40                  45

Ile Gly His Ile His Phe Ser Gly Arg Pro Thr Tyr Asn Pro Ser Leu
    50                  55                  60

Arg Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

```
Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
    435                 440                 445

Gly Lys
    450

<210> SEQ ID NO 38
<211> LENGTH: 450
<212> TYPE: PRT
<213> ORGANISM: Artificial Sequence
<220> FEATURE:
<223> OTHER INFORMATION: Antibody

<400> SEQUENCE: 38

Glu Val Gln Leu Gln Gln Trp Gly Ala Gly Leu Leu Lys Pro Ser Glu
1               5                   10                  15

Thr Leu Ser Leu Thr Cys Ala Val Tyr Gly Tyr Ser Ile Ser Ser Gly
            20                  25                  30

Tyr Ser Trp His Trp Ile Arg Gln Pro Pro Gly Lys Gly Leu Glu Trp
        35                  40                  45

Ile Gly His Ile His Phe Ser Gly Arg Pro Thr Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 39
<211> LENGTH: 450
<212> TYPE: PRT
<213> ORGANISM: Artificial Sequence
<220> FEATURE:
<223> OTHER INFORMATION: Antibody

<400> SEQUENCE: 39

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Gly
                20                  25                  30

Tyr Ser Trp His Trp Ile Arg Gln Ser Pro Gly Lys Gly Leu Gln Trp
            35                  40                  45

Ile Gly His Ile His Phe Ser Gly Arg Pro Thr Tyr Asn Pro Ser Leu
    50                  55                  60

Lys Ser Arg Val Thr Ile Ser Arg Glu Thr Ala Lys Asn Gln Phe Ser
65                  70                  75                  80
```

```
Leu Lys Leu Thr Ser Met Thr Ala Ala Asp Thr Ala Val Tyr Tyr Cys
                 85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
450

<210> SEQ ID NO 40
<211> LENGTH: 450
<212> TYPE: PRT
<213> ORGANISM: Artificial Sequence
<220> FEATURE:
```

<223> OTHER INFORMATION: Antibody

<400> SEQUENCE: 40

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln Ser Pro Gly Lys Gly Leu Gln Trp
        35                  40                  45

Ile Gly His Ile His Phe Ser Gly Arg Pro Thr Tyr Asn Pro Ser Leu
    50                  55                  60

Leu Ser Arg Val Thr Ile Ser Arg Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

-continued

```
Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
        435                 440                 445

Gly Lys
    450

<210> SEQ ID NO 41
<211> LENGTH: 450
<212> TYPE: PRT
<213> ORGANISM: Artificial Sequence
<220> FEATURE:
<223> OTHER INFORMATION: Antibody

<400> SEQUENCE: 41

Gln Val Gln Leu Gln Glu Ser Gly Pro Gly Leu Val Lys Pro Ser Glu
1               5                  10                  15

Thr Leu Ser Leu Thr Cys Thr Val Ser Gly Tyr Ser Ile Thr Ser Gly
            20                  25                  30

Tyr Ser Trp His Trp Ile Arg Gln Ser Pro Gly Lys Gly Leu Gln Trp
        35                  40                  45

Ile Gly His Ile His Phe Ser Gly Arg Pro Thr Tyr Asn Pro Ser Leu
    50                  55                  60

His Ser Arg Val Thr Ile Ser Arg Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ala Ser Thr Lys Asn Pro Asp Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300
```

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 42
<211> LENGTH: 450
<212> TYPE: PRT
<213> ORGANISM: Artificial Sequence
<220> FEATURE:
<223> OTHER INFORMATION: Antibody

<400> SEQUENCE: 42

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln Ser Pro Gly Lys Gly Leu Gln Trp
        35                  40                  45

Ile Gly His Ile His Phe Ser Gly Arg Pro Thr Tyr Asn Pro Ser Leu
    50                  55                  60

Phe Ser Arg Val Thr Ile Ser Arg Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ala Ser Thr Lys Asn Pro Asp Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

```
Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 43
<211> LENGTH: 450
<212> TYPE: PRT
<213> ORGANISM: Artificial Sequence
<220> FEATURE:
<223> OTHER INFORMATION: Antibody

<400> SEQUENCE: 43

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln Ser Pro Gly Lys Gly Leu Gln Trp
        35                  40                  45

Ile Gly His Ile His Phe Ser Gly Arg Pro Thr Tyr Asn Pro Ser Leu
    50                  55                  60

Arg Ser Arg Val Thr Ile Ser Arg Glu Thr Ala Lys Asn Gln Phe Ser
65                  70                  75                  80

Leu Lys Leu Thr Ser Met Thr Ala Ala Asp Thr Ala Val Tyr Tyr Cys
            85                  90                  95

Ala Arg Lys Gly Lys Gly Ser Asp Asp Gly Leu Asn Tyr Trp Gly Gln
            100                 105                 110
```

```
Gly Thr Leu Val Thr Val Ser Ser Ala Ser Thr Lys Asn Pro Asp Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 44
<211> LENGTH: 450
<212> TYPE: PRT
<213> ORGANISM: Artificial Sequence
<220> FEATURE:
<223> OTHER INFORMATION: Antibody

<400> SEQUENCE: 44

Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Tyr Ser Ile Thr Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

Ser Ser Arg Val Thr Ile Ser Arg Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
```

```
                435                 440                 445

Gly Lys
    450

<210> SEQ ID NO 45
<211> LENGTH: 450
<212> TYPE: PRT
<213> ORGANISM: Artificial Sequence
<220> FEATURE:
<223> OTHER INFORMATION: Antibody

<400> SEQUENCE: 45

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

Lys Ser Arg Val Thr Ile Ser Arg Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
```

```
                   340              345              350
Thr Leu Pro Pro Ser Arg Asp Glu Leu Thr Lys Asn Gln Val Ser Leu
            355                  360              365

Thr Cys Leu Val Lys Gly Phe Tyr Pro Ser Asp Ile Ala Val Glu Trp
        370                  375              380

Glu Ser Asn Gly Gln Pro Glu Asn Asn Tyr Lys Thr Thr Pro Pro Val
385                  390              395              400

Leu Asp Ser Asp Gly Ser Phe Phe Leu Tyr Ser Lys Leu Thr Val Asp
                405              410              415

Lys Ser Arg Trp Gln Gln Gly Asn Val Phe Ser Cys Ser Val Met His
            420              425              430

Glu Ala Leu His Asn His Tyr Thr Gln Lys Ser Leu Ser Leu Ser Pro
            435              440              445

Gly Lys
    450

<210> SEQ ID NO 46
<211> LENGTH: 450
<212> TYPE: PRT
<213> ORGANISM: Artificial Sequence
<220> FEATURE:
<223> OTHER INFORMATION: Antibody

<400> SEQUENCE: 46

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

Leu Ser Arg Val Thr Ile Ser Arg Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
```

-continued

```
                245                 250                 255
Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 47
<211> LENGTH: 450
<212> TYPE: PRT
<213> ORGANISM: Artificial Sequence
<220> FEATURE:
<223> OTHER INFORMATION: Antibody

<400> SEQUENCE: 47

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

His Ser Arg Val Thr Ile Ser Arg Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
```

```
            145                 150                 155                 160
        Trp Asn Ser Gly Ala Leu Thr Ser Gly Val His Thr Phe Pro Ala Val
                        165                 170                 175
        Leu Gln Ser Ser Gly Leu Tyr Ser Leu Ser Val Val Thr Val Pro
                        180                 185                 190
        Ser Ser Ser Leu Gly Thr Gln Thr Tyr Ile Cys Asn Val Asn His Lys
                        195                 200                 205
        Pro Ser Asn Thr Lys Val Asp Lys Lys Val Glu Pro Lys Ser Cys Asp
                210                 215                 220
        Lys Thr His Thr Cys Pro Pro Cys Pro Ala Pro Glu Leu Leu Gly Gly
        225                 230                 235                 240
        Pro Ser Val Phe Leu Phe Pro Pro Lys Pro Lys Asp Thr Leu Met Ile
                        245                 250                 255
        Ser Arg Thr Pro Glu Val Thr Cys Val Val Val Asp Val Ser His Glu
                        260                 265                 270
        Asp Pro Glu Val Lys Phe Asn Trp Tyr Val Asp Gly Val Glu Val His
                        275                 280                 285
        Asn Ala Lys Thr Lys Pro Arg Glu Glu Gln Tyr Asn Ser Thr Tyr Arg
                290                 295                 300
        Val Val Ser Val Leu Thr Val Leu His Gln Asp Trp Leu Asn Gly Lys
        305                 310                 315                 320
        Glu Tyr Lys Cys Lys Val Ser Asn Lys Ala Leu Pro Ala Pro Ile Glu
                        325                 330                 335
        Lys Thr Ile Ser Lys Ala Lys Gly Gln Pro Arg Glu Pro Gln Val Tyr
                        340                 345                 350
        Thr Leu Pro Pro Ser Arg Asp Glu Leu Thr Lys Asn Gln Val Ser Leu
                        355                 360                 365
        Thr Cys Leu Val Lys Gly Phe Tyr Pro Ser Asp Ile Ala Val Glu Trp
                370                 375                 380
        Glu Ser Asn Gly Gln Pro Glu Asn Asn Tyr Lys Thr Thr Pro Pro Val
        385                 390                 395                 400
        Leu Asp Ser Asp Gly Ser Phe Phe Leu Tyr Ser Lys Leu Thr Val Asp
                        405                 410                 415
        Lys Ser Arg Trp Gln Gln Gly Asn Val Phe Ser Cys Ser Val Met His
                        420                 425                 430
        Glu Ala Leu His Asn His Tyr Thr Gln Lys Ser Leu Ser Leu Ser Pro
                        435                 440                 445
        Gly Lys
            450

<210> SEQ ID NO 48
<211> LENGTH: 450
<212> TYPE: PRT
<213> ORGANISM: Artificial Sequence
<220> FEATURE:
<223> OTHER INFORMATION: Antibody

<400> SEQUENCE: 48

Gln Val Gln Leu Gln Glu Ser Gly Pro Gly Leu Val Lys Pro Ser Glu
        1               5                   10                  15
        Thr Leu Ser Leu Thr Cys Thr Val Ser Gly Tyr Ser Ile Thr Ser Gly
                        20                  25                  30
        Tyr Ser Trp His Trp Ile Arg Gln Pro Pro Gly Lys Gly Leu Gln Trp
                        35                  40                  45
        Ile Gly His Ile His Phe Ser Gly Arg Pro Thr Tyr Asn Pro Ser Leu
```

-continued

```
                50                  55                  60
Phe Ser Arg Val Thr Ile Ser Arg Glu Thr Ala Lys Asn Gln Phe Ser
 65                  70                  75                  80

Leu Lys Leu Thr Ser Met Thr Ala Ala Asp Thr Ala Val Tyr Tyr Cys
                 85                  90                  95

Ala Arg Lys Gly Lys Gly Ser Asp Asp Gly Leu Asn Tyr Trp Gly Gln
                100                 105                 110

Gly Thr Leu Val Thr Val Ser Ser Ala Ser Thr Lys Asn Pro Asp Val
                115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
                290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
450

<210> SEQ ID NO 49
```

<211> LENGTH: 450
<212> TYPE: PRT
<213> ORGANISM: Artificial Sequence
<220> FEATURE:
<223> OTHER INFORMATION: Antibody

<400> SEQUENCE: 49

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

Arg Ser Arg Val Thr Ile Ser Arg Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
        435                 440                 445

Gly Lys
    450

<210> SEQ ID NO 50
<211> LENGTH: 450
<212> TYPE: PRT
<213> ORGANISM: Artificial Sequence
<220> FEATURE:
<223> OTHER INFORMATION: Antibody

<400> SEQUENCE: 50

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

Lys Ser Arg Val Thr Ile Ser Arg Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285
```

```
Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 51
<211> LENGTH: 450
<212> TYPE: PRT
<213> ORGANISM: Artificial Sequence
<220> FEATURE:
<223> OTHER INFORMATION: Antibody

<400> SEQUENCE: 51

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Val Arg Gln Phe Pro Gly Asn Lys Met Glu Trp
        35                  40                  45

Met Gly His Ile His Phe Ser Gly Arg Pro Thr Tyr Asp Pro Ser Leu
    50                  55                  60

Ser Ser Arg Ile Ser Ile Thr Arg Asp Thr Ser Lys Asn Gln Phe Leu
65                  70                  75                  80

Leu Gln Leu Lys Phe Val Thr Thr Glu Asp Thr Ser Thr Tyr Phe Cys
                85                  90                  95

Ala Arg Lys Gly Lys Gly Ser Asp Gly Leu Asn Tyr Trp Gly Gln
                100                 105                 110

Gly Ile Ser Val Thr Val Ser Ser Ala Ser Thr Lys Asn Pro Asp Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 52
<211> LENGTH: 330
<212> TYPE: PRT
<213> ORGANISM: Homo sapiens

<400> SEQUENCE: 52

Ala Ser Thr Lys Asn Pro Asp Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
```

```
            100                 105                 110
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 53
<211> LENGTH: 330
<212> TYPE: PRT
<213> ORGANISM: Homo sapiens

<400> SEQUENCE: 53

Ala Ser Thr Lys Asn Pro Asp Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
            115                 120                 125

Lys Pro Lys Asp Thr Leu Met Ile Ser Arg Thr Pro Glu Val Thr Cys
    130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ala Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 54
<211> LENGTH: 450
<212> TYPE: PRT
<213> ORGANISM: Artificial Sequence
<220> FEATURE:
<223> OTHER INFORMATION: Antibody

<400> SEQUENCE: 54

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ala Ser Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

Lys Ser Arg Val Thr Ile Ser Arg Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 55
<211> LENGTH: 450
<212> TYPE: PRT
<213> ORGANISM: Artificial Sequence
<220> FEATURE:
<223> OTHER INFORMATION: Antibody

<400> SEQUENCE: 55

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Cys Ser Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

Lys Ser Arg Val Thr Ile Ser Arg Glu Thr Ala Lys Asn Gln Phe Ser
65                  70                  75                  80
```

```
Leu Lys Leu Thr Ser Met Thr Ala Ala Asp Thr Ala Val Tyr Tyr Cys
                 85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 56
<211> LENGTH: 450
<212> TYPE: PRT
<213> ORGANISM: Artificial Sequence
<220> FEATURE:
<223> OTHER INFORMATION: Antibody
```

<400> SEQUENCE: 56

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Asp Ser Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

Lys Ser Arg Val Thr Ile Ser Arg Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp

```
                    405                 410                 415
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 57
<211> LENGTH: 450
<212> TYPE: PRT
<213> ORGANISM: Artificial Sequence
<220> FEATURE:
<223> OTHER INFORMATION: Antibody

<400> SEQUENCE: 57

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Glu Ser Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

Lys Ser Arg Val Thr Ile Ser Arg Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
```

```
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 58
<211> LENGTH: 450
<212> TYPE: PRT
<213> ORGANISM: Artificial Sequence
<220> FEATURE:
<223> OTHER INFORMATION: Antibody

<400> SEQUENCE: 58

Gln Val Gln Leu Gln Glu Ser Gly Pro Gly Leu Val Lys Pro Ser Glu
1               5                   10                  15
Thr Leu Ser Leu Thr Cys Thr Val Ser Gly Tyr Ser Phe Ser Ser Gly
                20                  25                  30
Tyr Ser Trp His Trp Ile Arg Gln Pro Pro Gly Lys Gly Leu Gln Trp
            35                  40                  45
Ile Gly His Ile His Phe Ser Gly Arg Pro Thr Tyr Asn Pro Ser Leu
    50                  55                  60
Lys Ser Arg Val Thr Ile Ser Arg Glu Thr Ala Lys Asn Gln Phe Ser
65                  70                  75                  80
Leu Lys Leu Thr Ser Met Thr Ala Ala Asp Thr Ala Val Tyr Tyr Cys
                85                  90                  95
Ala Arg Lys Gly Lys Gly Ser Asp Asp Gly Leu Asn Tyr Trp Gly Gln
            100                 105                 110
Gly Thr Leu Val Thr Val Ser Ala Ser Thr Lys Asn Pro Asp Val
            115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
```

```
            210                 215                 220
Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 59
<211> LENGTH: 450
<212> TYPE: PRT
<213> ORGANISM: Artificial Sequence
<220> FEATURE:
<223> OTHER INFORMATION: Antibody

<400> SEQUENCE: 59

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Gly Ser Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

Lys Ser Arg Val Thr Ile Ser Arg Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
```

```
                    115                 120                 125
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
        210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 60
<211> LENGTH: 450
<212> TYPE: PRT
<213> ORGANISM: Artificial Sequence
<220> FEATURE:
<223> OTHER INFORMATION: Antibody

<400> SEQUENCE: 60

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser His Ser Ser Gly
```

-continued

```
                20                  25                  30
Tyr Ser Trp His Trp Ile Arg Gln Pro Pro Gly Lys Gly Leu Gln Trp
             35                  40                  45
Ile Gly His Ile His Phe Ser Gly Arg Pro Thr Tyr Asn Pro Ser Leu
         50                  55                  60
Lys Ser Arg Val Thr Ile Ser Arg Glu Thr Ala Lys Asn Gln Phe Ser
 65                  70                  75                  80
Leu Lys Leu Thr Ser Met Thr Ala Ala Asp Thr Ala Val Tyr Tyr Cys
                 85                  90                  95
Ala Arg Lys Gly Lys Gly Ser Asp Asp Gly Leu Asn Tyr Trp Gly Gln
            100                 105                 110
Gly Thr Leu Val Thr Val Ser Ala Ser Thr Lys Asn Pro Asp Val
        115                 120                 125
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
            165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
            245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
            325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
        370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
```

Gly Lys
    450

<210> SEQ ID NO 61
<211> LENGTH: 450
<212> TYPE: PRT
<213> ORGANISM: Artificial Sequence
<220> FEATURE:
<223> OTHER INFORMATION: Antibody

<400> SEQUENCE: 61

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Lys Ser Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

Lys Ser Arg Val Thr Ile Ser Arg Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

```
Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 62
<211> LENGTH: 450
<212> TYPE: PRT
<213> ORGANISM: Artificial Sequence
<220> FEATURE:
<223> OTHER INFORMATION: Antibody

<400> SEQUENCE: 62

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Leu Ser Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

Lys Ser Arg Val Thr Ile Ser Arg Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 63
<211> LENGTH: 450
<212> TYPE: PRT
<213> ORGANISM: Artificial Sequence
<220> FEATURE:
<223> OTHER INFORMATION: Antibody

<400> SEQUENCE: 63

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Met Ser Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

Lys Ser Arg Val Thr Ile Ser Arg Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 64
<211> LENGTH: 450
<212> TYPE: PRT
<213> ORGANISM: Artificial Sequence
<220> FEATURE:
<223> OTHER INFORMATION: Antibody

<400> SEQUENCE: 64

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Asn Ser Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60
```

```
Lys Ser Arg Val Thr Ile Ser Arg Glu Thr Ala Lys Asn Gln Phe Ser
 65                  70                  75                  80

Leu Lys Leu Thr Ser Met Thr Ala Ala Asp Thr Ala Val Tyr Tyr Cys
                 85                  90                  95

Ala Arg Lys Gly Lys Gly Ser Asp Asp Gly Leu Asn Tyr Trp Gly Gln
            100                 105                 110

Gly Thr Leu Val Thr Val Ser Ala Ser Thr Lys Asn Pro Asp Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
450

<210> SEQ ID NO 65
<211> LENGTH: 450
```

```
<212> TYPE: PRT
<213> ORGANISM: Artificial Sequence
<220> FEATURE:
<223> OTHER INFORMATION: Antibody

<400> SEQUENCE: 65

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Pro Ser Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

Lys Ser Arg Val Thr Ile Ser Arg Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380
```

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 66
<211> LENGTH: 450
<212> TYPE: PRT
<213> ORGANISM: Artificial Sequence
<220> FEATURE:
<223> OTHER INFORMATION: Antibody

<400> SEQUENCE: 66

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Gln Ser Ser Gly
            20                  25                  30

Tyr Ser Trp His Trp Ile Arg Gln Pro Pro Gly Lys Gly Leu Gln Trp
            35                  40                  45

Ile Gly His Ile His Phe Ser Gly Arg Pro Thr Tyr Asn Pro Ser Leu
50                  55                  60

Lys Ser Arg Val Thr Ile Ser Arg Glu Thr Ala Lys Asn Gln Phe Ser
65                  70                  75                  80

Leu Lys Leu Thr Ser Met Thr Ala Ala Asp Thr Ala Val Tyr Tyr Cys
            85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

```
Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 67
<211> LENGTH: 450
<212> TYPE: PRT
<213> ORGANISM: Artificial Sequence
<220> FEATURE:
<223> OTHER INFORMATION: Antibody

<400> SEQUENCE: 67

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Arg Ser Ser Gly
                20                  25                  30

Tyr Ser Trp His Trp Ile Arg Gln Pro Pro Gly Lys Gly Leu Gln Trp
                35                  40                  45

Ile Gly His Ile His Phe Ser Gly Arg Pro Thr Tyr Asn Pro Ser Leu
    50                  55                  60

Lys Ser Arg Val Thr Ile Ser Arg Glu Thr Ala Lys Asn Gln Phe Ser
65                  70                  75                  80

Leu Lys Leu Thr Ser Met Thr Ala Asp Thr Ala Val Tyr Tyr Cys
                85                  90                  95

Ala Arg Lys Gly Lys Gly Ser Asp Asp Gly Leu Asn Tyr Trp Gly Gln
                100                 105                 110

Gly Thr Leu Val Thr Val Ser Ser Ala Ser Thr Lys Asn Pro Asp Val
                115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190
```

```
Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
                435                 440                 445

Gly Lys
    450

<210> SEQ ID NO 68
<211> LENGTH: 450
<212> TYPE: PRT
<213> ORGANISM: Artificial Sequence
<220> FEATURE:
<223> OTHER INFORMATION: Antibody

<400> SEQUENCE: 68

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ser Ser Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

Lys Ser Arg Val Thr Ile Ser Arg Glu Thr Ala Lys Asn Gln Phe Ser
65                  70                  75                  80

Leu Lys Leu Thr Ser Met Thr Ala Ala Asp Thr Ala Val Tyr Tyr Cys
            85                  90                  95
```

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 69
<211> LENGTH: 450
<212> TYPE: PRT
<213> ORGANISM: Artificial Sequence
<220> FEATURE:
<223> OTHER INFORMATION: Antibody

<400> SEQUENCE: 69

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Tyr Ser Thr Ser Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
 50                  55                  60

Lys Ser Arg Val Thr Ile Ser Arg Glu Thr Ala Lys Asn Gln Phe Ser
 65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
 210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
 290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
 370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
```

```
                    420                 425                 430
Glu Ala Leu His Asn His Tyr Thr Gln Lys Ser Leu Ser Leu Ser Pro
            435                 440                 445
Gly Lys
    450

<210> SEQ ID NO 70
<211> LENGTH: 450
<212> TYPE: PRT
<213> ORGANISM: Artificial Sequence
<220> FEATURE:
<223> OTHER INFORMATION: Antibody

<400> SEQUENCE: 70

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Val Ser Ser Gly
            20                  25                  30

Tyr Ser Trp His Trp Ile Arg Gln Pro Gly Lys Gly Leu Gln Trp
        35                  40                  45

Ile Gly His Ile His Phe Ser Gly Arg Pro Thr Tyr Asn Pro Ser Leu
    50                  55                  60

Lys Ser Arg Val Thr Ile Ser Arg Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
```

```
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
Gly Lys
    450

<210> SEQ ID NO 71
<211> LENGTH: 450
<212> TYPE: PRT
<213> ORGANISM: Artificial Sequence
<220> FEATURE:
<223> OTHER INFORMATION: Antibody

<400> SEQUENCE: 71

Gln Val Gln Leu Gln Glu Ser Gly Pro Gly Leu Val Lys Pro Ser Glu
1               5                   10                  15
Thr Leu Ser Leu Thr Cys Thr Val Ser Gly Tyr Ser Trp Ser Ser Gly
            20                  25                  30
Tyr Ser Trp His Trp Ile Arg Gln Pro Pro Gly Lys Gly Leu Gln Trp
            35                  40                  45
Ile Gly His Ile His Phe Ser Gly Arg Pro Thr Tyr Asn Pro Ser Leu
    50                  55                  60
Lys Ser Arg Val Thr Ile Ser Arg Glu Thr Ala Lys Asn Gln Phe Ser
65                  70                  75                  80
Leu Lys Leu Thr Ser Met Thr Ala Ala Asp Thr Ala Val Tyr Tyr Cys
            85                  90                  95
Ala Arg Lys Gly Lys Gly Ser Asp Asp Gly Leu Asn Tyr Trp Gly Gln
            100                 105                 110
Gly Thr Leu Val Thr Val Ser Ser Ala Ser Thr Lys Asn Pro Asp Val
            115                 120                 125
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
            165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
            210                 215                 220
Lys Thr His Thr Cys Pro Pro Cys Pro Ala Pro Glu Leu Leu Gly Gly
```

```
225                 230                 235                 240
Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
                290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 72
<211> LENGTH: 450
<212> TYPE: PRT
<213> ORGANISM: Artificial Sequence
<220> FEATURE:
<223> OTHER INFORMATION: Antibody

<400> SEQUENCE: 72

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Tyr Ser Ser Gly
                20                  25                  30

Tyr Ser Trp His Trp Ile Arg Gln Pro Pro Gly Lys Gly Leu Gln Trp
                35                  40                  45

Ile Gly His Ile His Phe Ser Gly Arg Pro Thr Tyr Asn Pro Ser Leu
50                  55                  60

Lys Ser Arg Val Thr Ile Ser Arg Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
                100                 105                 110

Gly Thr Leu Val Thr Val Ser Ser Ala Ser Thr Lys Asn Pro Asp Val
                115                 120                 125

Phe Pro Leu Ala Pro Ser Ser Lys Ser Thr Ser Gly Gly Thr Ala Ala
```

```
            130                 135                 140
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 73
<211> LENGTH: 450
<212> TYPE: PRT
<213> ORGANISM: Artificial Sequence
<220> FEATURE:
<223> OTHER INFORMATION: Antibody

<400> SEQUENCE: 73

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Gly
                20                  25                  30

Tyr Ser Trp His Trp Ile Arg Gln Pro Pro Gly Lys Gly Leu Gln Trp
```

```
                35                  40                  45
Ile Gly His Ile His Phe Ser Gly Arg Pro Thr Tyr Asn Pro Ser Leu
 50                  55                  60

Lys Ser Arg Val Thr Ile Ser Ala Glu Thr Ala Lys Asn Gln Phe Ser
 65                  70                  75                  80

Leu Lys Leu Thr Ser Met Thr Ala Ala Asp Thr Ala Val Tyr Tyr Cys
                 85                  90                  95

Ala Arg Lys Gly Lys Gly Ser Asp Asp Gly Leu Asn Tyr Trp Gly Gln
                100                 105                 110

Gly Thr Leu Val Thr Val Ser Ala Ser Thr Lys Asn Pro Asp Val
                115                 120                 125

Phe Pro Leu Ala Pro Ser Ser Lys Ser Thr Ser Gly Gly Thr Ala Ala
 130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
450
```

<210> SEQ ID NO 74
<211> LENGTH: 450
<212> TYPE: PRT
<213> ORGANISM: Artificial Sequence
<220> FEATURE:
<223> OTHER INFORMATION: Antibody

<400> SEQUENCE: 74

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

Lys Ser Arg Val Thr Ile Ser Cys Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365
```

```
Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
        435                 440                 445

Gly Lys
    450

<210> SEQ ID NO 75
<211> LENGTH: 450
<212> TYPE: PRT
<213> ORGANISM: Artificial Sequence
<220> FEATURE:
<223> OTHER INFORMATION: Antibody

<400> SEQUENCE: 75

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

Lys Ser Arg Val Thr Ile Ser Asp Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

-continued

```
Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 76
<211> LENGTH: 450
<212> TYPE: PRT
<213> ORGANISM: Artificial Sequence
<220> FEATURE:
<223> OTHER INFORMATION: Antibody

<400> SEQUENCE: 76

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

Lys Ser Arg Val Thr Ile Ser Glu Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

Leu Gln Ser Ser Gly Leu Tyr Ser Leu Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
                290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 77
<211> LENGTH: 450
<212> TYPE: PRT
<213> ORGANISM: Artificial Sequence
<220> FEATURE:
<223> OTHER INFORMATION: Antibody

<400> SEQUENCE: 77

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Gly
                20                  25                  30

Tyr Ser Trp His Trp Ile Arg Gln Pro Pro Gly Lys Gly Leu Gln Trp
                35                  40                  45

Ile Gly His Ile His Phe Ser Gly Arg Pro Thr Tyr Asn Pro Ser Leu
            50                  55                  60

Lys Ser Arg Val Thr Ile Ser Phe Glu Thr Ala Lys Asn Gln Phe Ser
65              70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 78
<211> LENGTH: 450
<212> TYPE: PRT
<213> ORGANISM: Artificial Sequence
<220> FEATURE:

<223> OTHER INFORMATION: Antibody

<400> SEQUENCE: 78

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

Lys Ser Arg Val Thr Ile Ser Gly Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

```
Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 79
<211> LENGTH: 450
<212> TYPE: PRT
<213> ORGANISM: Artificial Sequence
<220> FEATURE:
<223> OTHER INFORMATION: Antibody

<400> SEQUENCE: 79

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

Lys Ser Arg Val Thr Ile Ser His Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300
```

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 80
<211> LENGTH: 450
<212> TYPE: PRT
<213> ORGANISM: Artificial Sequence
<220> FEATURE:
<223> OTHER INFORMATION: Antibody

<400> SEQUENCE: 80

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Gly
            20                  25                  30

Tyr Ser Trp His Trp Ile Arg Gln Pro Pro Gly Lys Gly Leu Gln Trp
            35                  40                  45

Ile Gly His Ile His Phe Ser Gly Arg Pro Thr Tyr Asn Pro Ser Leu
50                  55                  60

Lys Ser Arg Val Thr Ile Ser Ile Glu Thr Ala Lys Asn Gln Phe Ser
65                  70                  75                  80

Leu Lys Leu Thr Ser Met Thr Ala Ala Asp Thr Ala Val Tyr Tyr Cys
            85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
            195                 200                 205
```

-continued

Pro Ser Asn Thr Lys Val Asp Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 81
<211> LENGTH: 450
<212> TYPE: PRT
<213> ORGANISM: Artificial Sequence
<220> FEATURE:
<223> OTHER INFORMATION: Antibody

<400> SEQUENCE: 81

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

Lys Ser Arg Val Thr Ile Ser Lys Glu Thr Ala Lys Asn Gln Phe Ser
65                  70                  75                  80

Leu Lys Leu Thr Ser Met Thr Ala Ala Asp Thr Ala Val Tyr Tyr Cys
            85                  90                  95

Ala Arg Lys Gly Lys Gly Ser Asp Asp Gly Leu Asn Tyr Trp Gly Gln
        100                 105                 110

```
Gly Thr Leu Val Thr Val Ser Ser Ala Ser Thr Lys Asn Pro Asp Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 82
<211> LENGTH: 450
<212> TYPE: PRT
<213> ORGANISM: Artificial Sequence
<220> FEATURE:
<223> OTHER INFORMATION: Antibody

<400> SEQUENCE: 82

Gln Val Gln Leu Gln Glu Ser Gly Pro Gly Leu Val Lys Pro Ser Glu
1               5                   10                  15
```

-continued

```
Thr Leu Ser Leu Thr Cys Thr Val Ser Gly Tyr Ser Ile Ser Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

Lys Ser Arg Val Thr Ile Ser Leu Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
```

```
            435                 440                 445

Gly Lys
    450

<210> SEQ ID NO 83
<211> LENGTH: 450
<212> TYPE: PRT
<213> ORGANISM: Artificial Sequence
<220> FEATURE:
<223> OTHER INFORMATION: Antibody

<400> SEQUENCE: 83

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

Lys Ser Arg Val Thr Ile Ser Met Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
```

```
                    340                 345                 350
Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 84
<211> LENGTH: 450
<212> TYPE: PRT
<213> ORGANISM: Artificial Sequence
<220> FEATURE:
<223> OTHER INFORMATION: Antibody

<400> SEQUENCE: 84

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

Lys Ser Arg Val Thr Ile Ser Asn Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
```

```
                  245                 250                 255
Ser Arg Thr Pro Glu Val Thr Cys Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 85
<211> LENGTH: 450
<212> TYPE: PRT
<213> ORGANISM: Artificial Sequence
<220> FEATURE:
<223> OTHER INFORMATION: Antibody

<400> SEQUENCE: 85

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Gly
                20                  25                  30

Tyr Ser Trp His Trp Ile Arg Gln Pro Pro Gly Lys Gly Leu Gln Trp
            35                  40                  45

Ile Gly His Ile His Phe Ser Gly Arg Pro Thr Tyr Asn Pro Ser Leu
    50                  55                  60

Lys Ser Arg Val Thr Ile Ser Pro Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
                100                 105                 110

Gly Thr Leu Val Thr Val Ser Ser Ala Ser Thr Lys Asn Pro Asp Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
```

```
            145                 150                 155                 160
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 86
<211> LENGTH: 450
<212> TYPE: PRT
<213> ORGANISM: Artificial Sequence
<220> FEATURE:
<223> OTHER INFORMATION: Antibody

<400> SEQUENCE: 86

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Gly
                20                  25                  30

Tyr Ser Trp His Trp Ile Arg Gln Pro Pro Gly Lys Gly Leu Gln Trp
                35                  40                  45

Ile Gly His Ile His Phe Ser Gly Arg Pro Thr Tyr Asn Pro Ser Leu
```

```
              50                  55                  60
Lys Ser Arg Val Thr Ile Ser Gln Glu Thr Ala Lys Asn Gln Phe Ser
 65                  70                  75                  80

Leu Lys Leu Thr Ser Met Thr Ala Ala Asp Thr Ala Val Tyr Tyr Cys
                 85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 87
```

<211> LENGTH: 450
<212> TYPE: PRT
<213> ORGANISM: Artificial Sequence
<220> FEATURE:
<223> OTHER INFORMATION: Antibody

<400> SEQUENCE: 87

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

Lys Ser Arg Val Thr Ile Ser Ser Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 88
<211> LENGTH: 450
<212> TYPE: PRT
<213> ORGANISM: Artificial Sequence
<220> FEATURE:
<223> OTHER INFORMATION: Antibody

<400> SEQUENCE: 88

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Gly
                20                  25                  30

Tyr Ser Trp His Trp Ile Arg Gln Pro Pro Gly Lys Gly Leu Gln Trp
                35                  40                  45

Ile Gly His Ile His Phe Ser Gly Arg Pro Thr Tyr Asn Pro Ser Leu
    50                  55                  60

Lys Ser Arg Val Thr Ile Ser Thr Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
                100                 105                 110

Gly Thr Leu Val Thr Val Ser Ser Ala Ser Thr Lys Asn Pro Asp Val
                115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
                210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285
```

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 89
<211> LENGTH: 450
<212> TYPE: PRT
<213> ORGANISM: Artificial Sequence
<220> FEATURE:
<223> OTHER INFORMATION: Antibody

<400> SEQUENCE: 89

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

Lys Ser Arg Val Thr Ile Ser Val Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

```
Ser Ser Ser Leu Gly Thr Gln Thr Tyr Ile Cys Asn Val Asn His Lys
        195                 200                 205

Pro Ser Asn Thr Lys Val Asp Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 90
<211> LENGTH: 450
<212> TYPE: PRT
<213> ORGANISM: Artificial Sequence
<220> FEATURE:
<223> OTHER INFORMATION: Antibody

<400> SEQUENCE: 90

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

Lys Ser Arg Val Thr Ile Ser Trp Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95
```

```
Ala Arg Lys Gly Lys Gly Ser Asp Asp Gly Leu Asn Tyr Trp Gly Gln
            100                 105                 110

Gly Thr Leu Val Thr Val Ser Ala Ser Thr Lys Asn Pro Asp Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 91
<211> LENGTH: 450
<212> TYPE: PRT
<213> ORGANISM: Artificial Sequence
<220> FEATURE:
<223> OTHER INFORMATION: Antibody

<400> SEQUENCE: 91
```

-continued

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

Lys Ser Arg Val Thr Ile Ser Tyr Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ala Ser Thr Lys Asn Pro Asp Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 92
<211> LENGTH: 330
<212> TYPE: PRT
<213> ORGANISM: Homo sapiens

<400> SEQUENCE: 92

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 93
<211> LENGTH: 106
<212> TYPE: PRT
<213> ORGANISM: Homo sapiens

<400> SEQUENCE: 93

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 94
<211> LENGTH: 450
<212> TYPE: PRT
<213> ORGANISM: Artificial Sequence
<220> FEATURE:
<223> OTHER INFORMATION: Antibody

<400> SEQUENCE: 94

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Gly
            20                  25                  30

Tyr Ser Trp His Trp Ile Arg Gln Pro Pro Gly Lys Gly Leu Gln Trp
        35                  40                  45

Ile Gly His Ile His Phe Ser Gly Arg Pro Thr Tyr Asn Pro Ser Leu
    50                  55                  60

Lys Ser Arg Val Thr Ile Ser Arg Glu Thr Ala Lys Asn Gln Phe Ser
65                  70                  75                  80

Leu Lys Leu Thr Ser Met Thr Ala Ala Asp Thr Ala Val Tyr Tyr Cys
                85                  90                  95

Ala Arg Lys Gly Lys Gly Ser Asp Asp Gly Leu Asn Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

```
Pro Ser Asn Thr Lys Val Asp Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
            245                 250                 255
Ser Arg Thr Pro Glu Val Thr Cys Val Val Val Asp Val Ser His Glu
        260                 265                 270
Asp Pro Glu Val Lys Phe Asn Trp Tyr Val Asp Gly Val Glu Val His
    275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
            325                 330                 335
Lys Thr Ile Ser Lys Ala Lys Gly Gln Pro Arg Glu Pro Gln Val Tyr
        340                 345                 350
Thr Leu Pro Pro Ser Arg Asp Glu Leu Thr Lys Asn Gln Val Ser Leu
    355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
        420                 425                 430
Glu Ala Leu His Asn His Tyr Thr Gln Lys Ser Leu Ser Leu Ser Pro
    435                 440                 445
Gly Lys
    450

<210> SEQ ID NO 95
<211> LENGTH: 30
<212> TYPE: PRT
<213> ORGANISM: Artificial Sequence
<220> FEATURE:
<223> OTHER INFORMATION: Antibody
<220> FEATURE:
<221> NAME/KEY: VARIANT
<222> LOCATION: (1)..(1)
<223> OTHER INFORMATION: Xaa is Gln or Glu
<220> FEATURE:
<221> NAME/KEY: VARIANT
<222> LOCATION: (25)..(25)
<223> OTHER INFORMATION: Xaa is Ser or Thr
<220> FEATURE:
<221> NAME/KEY: VARIANT
<222> LOCATION: (29)..(29)
<223> OTHER INFORMATION: Xaa is Ile, Leu or Val
<220> FEATURE:
<221> NAME/KEY: VARIANT
<222> LOCATION: (30)..(30)
<223> OTHER INFORMATION: Xaa is Ser or Thr

<400> SEQUENCE: 95

Xaa Val Gln Leu Gln Glu Ser Gly Pro Gly Leu Val Lys Pro Ser Glu
1               5                   10                  15
Thr Leu Ser Leu Thr Cys Thr Val Xaa Gly Tyr Ser Xaa Xaa
            20                  25                  30
```

<210> SEQ ID NO 96
<211> LENGTH: 6
<212> TYPE: PRT
<213> ORGANISM: Artificial Sequence
<220> FEATURE:
<223> OTHER INFORMATION: Antibody

<400> SEQUENCE: 96

Ser Gly Tyr Ser Trp His
1               5

<210> SEQ ID NO 97
<211> LENGTH: 14
<212> TYPE: PRT
<213> ORGANISM: Artificial Sequence
<220> FEATURE:
<223> OTHER INFORMATION: Antibody
<220> FEATURE:
<221> NAME/KEY: VARIANT
<222> LOCATION: (5)..(5)
<223> OTHER INFORMATION: Xaa is Ser or Pro
<220> FEATURE:
<221> NAME/KEY: VARIANT
<222> LOCATION: (11)..(11)
<223> OTHER INFORMATION: Xaa is Gln or Glu
<220> FEATURE:
<221> NAME/KEY: VARIANT
<222> LOCATION: (13)..(13)
<223> OTHER INFORMATION: Xaa is Met or Ile

<400> SEQUENCE: 97

Trp Ile Arg Gln Xaa Pro Gly Lys Gly Leu Xaa Trp Xaa Gly
1               5                   10

<210> SEQ ID NO 98
<211> LENGTH: 16
<212> TYPE: PRT
<213> ORGANISM: Artificial Sequence
<220> FEATURE:
<223> OTHER INFORMATION: Antibody
<220> FEATURE:
<221> NAME/KEY: VARIANT
<222> LOCATION: (4)..(4)
<223> OTHER INFORMATION: Xaa is Phe, Tyr or Trp
<220> FEATURE:
<221> NAME/KEY: VARIANT
<222> LOCATION: (11)..(11)
<223> OTHER INFORMATION: Xaa is Asn or Asp
<220> FEATURE:
<221> NAME/KEY: VARIANT
<222> LOCATION: (15)..(15)
<223> OTHER INFORMATION: Xaa is Lys, Leu, His, Phe, Arg or Ser

<400> SEQUENCE: 98

His Ile His Xaa Ser Gly Arg Pro Thr Tyr Xaa Pro Ser Leu Xaa Ser
1               5                   10                  15

<210> SEQ ID NO 99
<211> LENGTH: 32
<212> TYPE: PRT
<213> ORGANISM: Artificial Sequence
<220> FEATURE:
<223> OTHER INFORMATION: Antibody
<220> FEATURE:
<221> NAME/KEY: VARIANT
<222> LOCATION: (2)..(2)
<223> OTHER INFORMATION: Xaa is Val or Ile
<220> FEATURE:
<221> NAME/KEY: VARIANT
<222> LOCATION: (3)..(3)
<223> OTHER INFORMATION: Xaa is Thr or Ser

```
<220> FEATURE:
<221> NAME/KEY: VARIANT
<222> LOCATION: (6)..(6)
<223> OTHER INFORMATION: Xaa is Arg or Lys
<220> FEATURE:
<221> NAME/KEY: VARIANT
<222> LOCATION: (7)..(7)
<223> OTHER INFORMATION: Xaa is Glu or Asp

<400> SEQUENCE: 99

Arg Xaa Xaa Ile Ser Xaa Xaa Thr Ala Lys Asn Gln Phe Ser Leu Lys
 1               5                  10                  15

Leu Thr Ser Met Thr Ala Ala Asp Thr Ala Val Tyr Tyr Cys Ala Arg
             20                  25                  30

<210> SEQ ID NO 100
<211> LENGTH: 11
<212> TYPE: PRT
<213> ORGANISM: Artificial Sequence
<220> FEATURE:
<223> OTHER INFORMATION: Antibody

<400> SEQUENCE: 100

Lys Gly Lys Gly Ser Asp Asp Gly Leu Asn Tyr
 1               5                  10

<210> SEQ ID NO 101
<211> LENGTH: 11
<212> TYPE: PRT
<213> ORGANISM: Artificial Sequence
<220> FEATURE:
<223> OTHER INFORMATION: Antibody

<400> SEQUENCE: 101

Trp Gly Gln Gly Thr Leu Val Thr Val Ser Ser
 1               5                  10

<210> SEQ ID NO 102
<211> LENGTH: 87
<212> TYPE: PRT
<213> ORGANISM: Artificial Sequence
<220> FEATURE:
<223> OTHER INFORMATION: Antibody
<220> FEATURE:
<221> NAME/KEY: VARIANT
<222> LOCATION: (29)..(29)
<223> OTHER INFORMATION: Xaa is Ile, Leu or Val
<220> FEATURE:
<221> NAME/KEY: VARIANT
<222> LOCATION: (50)..(50)
<223> OTHER INFORMATION: Xaa is Arg or Lys

<400> SEQUENCE: 102

Gln Val Gln Leu Gln Glu Ser Gly Pro Gly Leu Val Lys Pro Ser Glu
 1               5                  10                  15

Thr Leu Ser Leu Thr Cys Thr Val Ser Gly Tyr Ser Xaa Ser Trp Ile
             20                  25                  30

Arg Gln Pro Pro Gly Lys Gly Leu Gln Trp Ile Gly Arg Val Thr Ile
         35                  40                  45

Ser Xaa Glu Thr Ala Lys Asn Gln Phe Ser Leu Lys Leu Thr Ser Met
     50                  55                  60

Thr Ala Ala Asp Thr Ala Val Tyr Tyr Cys Ala Arg Trp Gly Gln Gly
 65                  70                  75                  80

Thr Leu Val Thr Val Ser Ser
                 85
```

<210> SEQ ID NO 103
<211> LENGTH: 30
<212> TYPE: PRT
<213> ORGANISM: Artificial Sequence
<220> FEATURE:
<223> OTHER INFORMATION: Antibody

<400> SEQUENCE: 103

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser
            20                  25                  30

<210> SEQ ID NO 104
<211> LENGTH: 30
<212> TYPE: PRT
<213> ORGANISM: Artificial Sequence
<220> FEATURE:
<223> OTHER INFORMATION: Antibody

<400> SEQUENCE: 104

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr
            20                  25                  30

<210> SEQ ID NO 105
<211> LENGTH: 30
<212> TYPE: PRT
<213> ORGANISM: Artificial Sequence
<220> FEATURE:
<223> OTHER INFORMATION: Antibody

<400> SEQUENCE: 105

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Leu Ser
            20                  25                  30

<210> SEQ ID NO 106
<211> LENGTH: 30
<212> TYPE: PRT
<213> ORGANISM: Artificial Sequence
<220> FEATURE:
<223> OTHER INFORMATION: Antibody

<400> SEQUENCE: 106

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Leu Thr
            20                  25                  30

<210> SEQ ID NO 107
<211> LENGTH: 30
<212> TYPE: PRT
<213> ORGANISM: Artificial Sequence
<220> FEATURE:
<223> OTHER INFORMATION: Antibody

<400> SEQUENCE: 107

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Val Ser
            20                  25                  30

<210> SEQ ID NO 108
<211> LENGTH: 30
<212> TYPE: PRT
<213> ORGANISM: Artificial Sequence
<220> FEATURE:
<223> OTHER INFORMATION: Antibody

<400> SEQUENCE: 108

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Val Thr
            20                  25                  30

<210> SEQ ID NO 109
<211> LENGTH: 30
<212> TYPE: PRT
<213> ORGANISM: Artificial Sequence
<220> FEATURE:
<223> OTHER INFORMATION: Antibody

<400> SEQUENCE: 109

Gln Val Gln Leu Gln Glu Ser Gly Pro Gly Leu Val Lys Pro Ser Glu
1               5                   10                  15

Thr Leu Ser Leu Thr Cys Thr Val Thr Gly Tyr Ser Ile Ser
            20                  25                  30

<210> SEQ ID NO 110
<211> LENGTH: 30
<212> TYPE: PRT
<213> ORGANISM: Artificial Sequence
<220> FEATURE:
<223> OTHER INFORMATION: Antibody

<400> SEQUENCE: 110

Gln Val Gln Leu Gln Glu Ser Gly Pro Gly Leu Val Lys Pro Ser Glu
1               5                   10                  15

Thr Leu Ser Leu Thr Cys Thr Val Thr Gly Tyr Ser Ile Thr
            20                  25                  30

<210> SEQ ID NO 111
<211> LENGTH: 30
<212> TYPE: PRT
<213> ORGANISM: Artificial Sequence
<220> FEATURE:
<223> OTHER INFORMATION: Antibody

<400> SEQUENCE: 111

Gln Val Gln Leu Gln Glu Ser Gly Pro Gly Leu Val Lys Pro Ser Glu
1               5                   10                  15

Thr Leu Ser Leu Thr Cys Thr Val Thr Gly Tyr Ser Leu Ser
            20                  25                  30

<210> SEQ ID NO 112
<211> LENGTH: 30
<212> TYPE: PRT
<213> ORGANISM: Artificial Sequence
<220> FEATURE:
<223> OTHER INFORMATION: Antibody

<400> SEQUENCE: 112

Gln Val Gln Leu Gln Glu Ser Gly Pro Gly Leu Val Lys Pro Ser Glu
1               5                   10                  15

Thr Leu Ser Leu Thr Cys Thr Val Thr Gly Tyr Ser Leu Thr

<210> SEQ ID NO 113
<211> LENGTH: 30
<212> TYPE: PRT
<213> ORGANISM: Artificial Sequence
<220> FEATURE:
<223> OTHER INFORMATION: Antibody

<400> SEQUENCE: 113

```
Gln Val Gln Leu Gln Glu Ser Gly Pro Gly Leu Val Lys Pro Ser Glu
1               5                   10                  15

Thr Leu Ser Leu Thr Cys Thr Val Thr Gly Tyr Ser Val Ser
            20                  25                  30
```

<210> SEQ ID NO 114
<211> LENGTH: 30
<212> TYPE: PRT
<213> ORGANISM: Artificial Sequence
<220> FEATURE:
<223> OTHER INFORMATION: Antibody

<400> SEQUENCE: 114

```
Gln Val Gln Leu Gln Glu Ser Gly Pro Gly Leu Val Lys Pro Ser Glu
1               5                   10                  15

Thr Leu Ser Leu Thr Cys Thr Val Thr Gly Tyr Ser Val Thr
            20                  25                  30
```

<210> SEQ ID NO 115
<211> LENGTH: 30
<212> TYPE: PRT
<213> ORGANISM: Artificial Sequence
<220> FEATURE:
<223> OTHER INFORMATION: Antibody

<400> SEQUENCE: 115

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser
            20                  25                  30
```

<210> SEQ ID NO 116
<211> LENGTH: 30
<212> TYPE: PRT
<213> ORGANISM: Artificial Sequence
<220> FEATURE:
<223> OTHER INFORMATION: Antibody

<400> SEQUENCE: 116

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr
            20                  25                  30
```

<210> SEQ ID NO 117
<211> LENGTH: 30
<212> TYPE: PRT
<213> ORGANISM: Artificial Sequence
<220> FEATURE:
<223> OTHER INFORMATION: Antibody

<400> SEQUENCE: 117

```
Glu Val Gln Leu Gln Glu Ser Gly Pro Gly Leu Val Lys Pro Ser Glu
1               5                   10                  15
```

```
Thr Leu Ser Leu Thr Cys Thr Val Ser Gly Tyr Ser Leu Ser
            20                  25                  30
```

<210> SEQ ID NO 118
<211> LENGTH: 30
<212> TYPE: PRT
<213> ORGANISM: Artificial Sequence
<220> FEATURE:
<223> OTHER INFORMATION: Antibody

<400> SEQUENCE: 118

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Leu Thr
            20                  25                  30
```

<210> SEQ ID NO 119
<211> LENGTH: 30
<212> TYPE: PRT
<213> ORGANISM: Artificial Sequence
<220> FEATURE:
<223> OTHER INFORMATION: Antibody

<400> SEQUENCE: 119

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Val Ser
            20                  25                  30
```

<210> SEQ ID NO 120
<211> LENGTH: 30
<212> TYPE: PRT
<213> ORGANISM: Artificial Sequence
<220> FEATURE:
<223> OTHER INFORMATION: Antibody

<400> SEQUENCE: 120

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Val Thr
            20                  25                  30
```

<210> SEQ ID NO 121
<211> LENGTH: 30
<212> TYPE: PRT
<213> ORGANISM: Artificial Sequence
<220> FEATURE:
<223> OTHER INFORMATION: Antibody

<400> SEQUENCE: 121

```
Glu Val Gln Leu Gln Glu Ser Gly Pro Gly Leu Val Lys Pro Ser Glu
1               5                   10                  15

Thr Leu Ser Leu Thr Cys Thr Val Thr Gly Tyr Ser Ile Ser
            20                  25                  30
```

<210> SEQ ID NO 122
<211> LENGTH: 30
<212> TYPE: PRT
<213> ORGANISM: Artificial Sequence
<220> FEATURE:
<223> OTHER INFORMATION: Antibody

<400> SEQUENCE: 122

```
Glu Val Gln Leu Gln Glu Ser Gly Pro Gly Leu Val Lys Pro Ser Glu
1               5                   10                  15
```

Thr Leu Ser Leu Thr Cys Thr Val Thr Gly Tyr Ser Ile Thr
            20                  25                  30

<210> SEQ ID NO 123
<211> LENGTH: 30
<212> TYPE: PRT
<213> ORGANISM: Artificial Sequence
<220> FEATURE:
<223> OTHER INFORMATION: Antibody

<400> SEQUENCE: 123

Glu Val Gln Leu Gln Glu Ser Gly Pro Gly Leu Val Lys Pro Ser Glu
1               5                   10                  15

Thr Leu Ser Leu Thr Cys Thr Val Thr Gly Tyr Ser Leu Ser
            20                  25                  30

<210> SEQ ID NO 124
<211> LENGTH: 30
<212> TYPE: PRT
<213> ORGANISM: Artificial Sequence
<220> FEATURE:
<223> OTHER INFORMATION: Antibody

<400> SEQUENCE: 124

Glu Val Gln Leu Gln Glu Ser Gly Pro Gly Leu Val Lys Pro Ser Glu
1               5                   10                  15

Thr Leu Ser Leu Thr Cys Thr Val Thr Gly Tyr Ser Leu Thr
            20                  25                  30

<210> SEQ ID NO 125
<211> LENGTH: 31
<212> TYPE: PRT
<213> ORGANISM: Artificial Sequence
<220> FEATURE:
<223> OTHER INFORMATION: Antibody

<400> SEQUENCE: 125

Glu Val Gln Leu Gln Glu Ser Gly Pro Gly Leu Val Lys Pro Ser Glu
1               5                   10                  15

Thr Leu Ser Leu Thr Cys Thr Val Ser Thr Gly Tyr Ser Val Ser
            20                  25                  30

<210> SEQ ID NO 126
<211> LENGTH: 30
<212> TYPE: PRT
<213> ORGANISM: Artificial Sequence
<220> FEATURE:
<223> OTHER INFORMATION: Antibody

<400> SEQUENCE: 126

Glu Val Gln Leu Gln Glu Ser Gly Pro Gly Leu Val Lys Pro Ser Glu
1               5                   10                  15

Thr Leu Ser Leu Thr Cys Thr Val Thr Gly Tyr Ser Val Thr
            20                  25                  30

<210> SEQ ID NO 127
<211> LENGTH: 14
<212> TYPE: PRT
<213> ORGANISM: Artificial Sequence
<220> FEATURE:
<223> OTHER INFORMATION: Antibody

<400> SEQUENCE: 127

Trp Ile Arg Gln Ser Pro Gly Lys Gly Leu Gln Trp Ile Gly

```
1               5                   10
```

<210> SEQ ID NO 128
<211> LENGTH: 14
<212> TYPE: PRT
<213> ORGANISM: Artificial Sequence
<220> FEATURE:
<223> OTHER INFORMATION: Antibody

<400> SEQUENCE: 128

```
Trp Ile Arg Gln Ser Pro Gly Lys Gly Leu Gln Trp Met Gly
1               5                   10
```

<210> SEQ ID NO 129
<211> LENGTH: 14
<212> TYPE: PRT
<213> ORGANISM: Artificial Sequence
<220> FEATURE:
<223> OTHER INFORMATION: Antibody

<400> SEQUENCE: 129

```
Trp Ile Arg Gln Ser Pro Gly Lys Gly Leu Glu Trp Ile Gly
1               5                   10
```

<210> SEQ ID NO 130
<211> LENGTH: 14
<212> TYPE: PRT
<213> ORGANISM: Artificial Sequence
<220> FEATURE:
<223> OTHER INFORMATION: Antibody

<400> SEQUENCE: 130

```
Trp Ile Arg Gln Ser Pro Gly Lys Gly Leu Glu Trp Met Gly
1               5                   10
```

<210> SEQ ID NO 131
<211> LENGTH: 14
<212> TYPE: PRT
<213> ORGANISM: Artificial Sequence
<220> FEATURE:
<223> OTHER INFORMATION: Antibody

<400> SEQUENCE: 131

```
Trp Ile Arg Gln Pro Pro Gly Lys Gly Leu Gln Trp Ile Gly
1               5                   10
```

<210> SEQ ID NO 132
<211> LENGTH: 14
<212> TYPE: PRT
<213> ORGANISM: Artificial Sequence
<220> FEATURE:
<223> OTHER INFORMATION: Antibody

<400> SEQUENCE: 132

```
Trp Ile Arg Gln Pro Pro Gly Lys Gly Leu Gln Trp Met Gly
1               5                   10
```

<210> SEQ ID NO 133
<211> LENGTH: 14
<212> TYPE: PRT
<213> ORGANISM: Artificial Sequence
<220> FEATURE:
<223> OTHER INFORMATION: Antibody

<400> SEQUENCE: 133

```
Trp Ile Arg Gln Pro Pro Gly Lys Gly Leu Glu Trp Ile Gly
1               5                   10
```

-continued

```
<210> SEQ ID NO 134
<211> LENGTH: 14
<212> TYPE: PRT
<213> ORGANISM: Artificial Sequence
<220> FEATURE:
<223> OTHER INFORMATION: Antibody

<400> SEQUENCE: 134

Trp Ile Arg Gln Pro Pro Gly Lys Gly Leu Glu Trp Met Gly
1               5                   10

<210> SEQ ID NO 135
<211> LENGTH: 16
<212> TYPE: PRT
<213> ORGANISM: Artificial Sequence
<220> FEATURE:
<223> OTHER INFORMATION: Antibody

<400> SEQUENCE: 135

His Ile His Phe Ser Gly Arg Pro Thr Tyr Asn Pro Ser Leu Ser Ser
1               5                   10                  15

<210> SEQ ID NO 136
<211> LENGTH: 16
<212> TYPE: PRT
<213> ORGANISM: Artificial Sequence
<220> FEATURE:
<223> OTHER INFORMATION: Antibody

<400> SEQUENCE: 136

His Ile His Phe Ser Gly Arg Pro Thr Tyr Asn Pro Ser Leu Lys Ser
1               5                   10                  15

<210> SEQ ID NO 137
<211> LENGTH: 16
<212> TYPE: PRT
<213> ORGANISM: Artificial Sequence
<220> FEATURE:
<223> OTHER INFORMATION: Antibody

<400> SEQUENCE: 137

His Ile His Phe Ser Gly Arg Pro Thr Tyr Asn Pro Ser Leu Leu Ser
1               5                   10                  15

<210> SEQ ID NO 138
<211> LENGTH: 16
<212> TYPE: PRT
<213> ORGANISM: Artificial Sequence
<220> FEATURE:
<223> OTHER INFORMATION: Antibody

<400> SEQUENCE: 138

His Ile His Phe Ser Gly Arg Pro Thr Tyr Asn Pro Ser Leu His Ser
1               5                   10                  15

<210> SEQ ID NO 139
<211> LENGTH: 16
<212> TYPE: PRT
<213> ORGANISM: Artificial Sequence
<220> FEATURE:
<223> OTHER INFORMATION: Antibody

<400> SEQUENCE: 139

His Ile His Phe Ser Gly Arg Pro Thr Tyr Asn Pro Ser Leu Phe Ser
1               5                   10                  15
```

<210> SEQ ID NO 140
<211> LENGTH: 16
<212> TYPE: PRT
<213> ORGANISM: Artificial Sequence
<220> FEATURE:
<223> OTHER INFORMATION: Antibody

<400> SEQUENCE: 140

His Ile His Phe Ser Gly Arg Pro Thr Tyr Asn Pro Ser Leu Arg Ser
1               5                   10                  15

<210> SEQ ID NO 141
<211> LENGTH: 16
<212> TYPE: PRT
<213> ORGANISM: Artificial Sequence
<220> FEATURE:
<223> OTHER INFORMATION: Antibody

<400> SEQUENCE: 141

His Ile His Trp Ser Gly Arg Pro Thr Tyr Asn Pro Ser Leu Ser Ser
1               5                   10                  15

<210> SEQ ID NO 142
<211> LENGTH: 16
<212> TYPE: PRT
<213> ORGANISM: Artificial Sequence
<220> FEATURE:
<223> OTHER INFORMATION: Antibody

<400> SEQUENCE: 142

His Ile His Trp Ser Gly Arg Pro Thr Tyr Asn Pro Ser Leu Lys Ser
1               5                   10                  15

<210> SEQ ID NO 143
<211> LENGTH: 16
<212> TYPE: PRT
<213> ORGANISM: Artificial Sequence
<220> FEATURE:
<223> OTHER INFORMATION: Antibody

<400> SEQUENCE: 143

His Ile His Trp Ser Gly Arg Pro Thr Tyr Asn Pro Ser Leu Leu Ser
1               5                   10                  15

<210> SEQ ID NO 144
<211> LENGTH: 16
<212> TYPE: PRT
<213> ORGANISM: Artificial Sequence
<220> FEATURE:
<223> OTHER INFORMATION: Antibody

<400> SEQUENCE: 144

His Ile His Trp Ser Gly Arg Pro Thr Tyr Asn Pro Ser Leu His Ser
1               5                   10                  15

<210> SEQ ID NO 145
<211> LENGTH: 16
<212> TYPE: PRT
<213> ORGANISM: Artificial Sequence
<220> FEATURE:
<223> OTHER INFORMATION: Antibody

<400> SEQUENCE: 145

His Ile His Trp Ser Gly Arg Pro Thr Tyr Asn Pro Ser Leu Phe Ser
1               5                   10                  15

```
<210> SEQ ID NO 146
<211> LENGTH: 16
<212> TYPE: PRT
<213> ORGANISM: Artificial Sequence
<220> FEATURE:
<223> OTHER INFORMATION: Antibody

<400> SEQUENCE: 146

His Ile His Trp Ser Gly Arg Pro Thr Tyr Asn Pro Ser Leu Arg Ser
1               5                   10                  15

<210> SEQ ID NO 147
<211> LENGTH: 16
<212> TYPE: PRT
<213> ORGANISM: Artificial Sequence
<220> FEATURE:
<223> OTHER INFORMATION: Antibody

<400> SEQUENCE: 147

His Ile His Tyr Ser Gly Arg Pro Thr Tyr Asn Pro Ser Leu Ser Ser
1               5                   10                  15

<210> SEQ ID NO 148
<211> LENGTH: 16
<212> TYPE: PRT
<213> ORGANISM: Artificial Sequence
<220> FEATURE:
<223> OTHER INFORMATION: Antibody

<400> SEQUENCE: 148

His Ile His Tyr Ser Gly Arg Pro Thr Tyr Asn Pro Ser Leu Lys Ser
1               5                   10                  15

<210> SEQ ID NO 149
<211> LENGTH: 16
<212> TYPE: PRT
<213> ORGANISM: Artificial Sequence
<220> FEATURE:
<223> OTHER INFORMATION: Antibody

<400> SEQUENCE: 149

His Ile His Tyr Ser Gly Arg Pro Thr Tyr Asn Pro Ser Leu Leu Ser
1               5                   10                  15

<210> SEQ ID NO 150
<211> LENGTH: 16
<212> TYPE: PRT
<213> ORGANISM: Artificial Sequence
<220> FEATURE:
<223> OTHER INFORMATION: Antibody

<400> SEQUENCE: 150

His Ile His Tyr Ser Gly Arg Pro Thr Tyr Asn Pro Ser Leu His Ser
1               5                   10                  15

<210> SEQ ID NO 151
<211> LENGTH: 16
<212> TYPE: PRT
<213> ORGANISM: Artificial Sequence
<220> FEATURE:
<223> OTHER INFORMATION: Antibody

<400> SEQUENCE: 151

His Ile His Tyr Ser Gly Arg Pro Thr Tyr Asn Pro Ser Leu Phe Ser
1               5                   10                  15

<210> SEQ ID NO 152
```

```
<211> LENGTH: 16
<212> TYPE: PRT
<213> ORGANISM: Artificial Sequence
<220> FEATURE:
<223> OTHER INFORMATION: Antibody

<400> SEQUENCE: 152

His Ile His Tyr Ser Gly Arg Pro Thr Tyr Asn Pro Ser Leu Arg Ser
1               5                   10                  15

<210> SEQ ID NO 153
<211> LENGTH: 16
<212> TYPE: PRT
<213> ORGANISM: Artificial Sequence
<220> FEATURE:
<223> OTHER INFORMATION: Antibody

<400> SEQUENCE: 153

His Ile His Phe Ser Gly Arg Pro Thr Tyr Asp Pro Ser Leu Ser Ser
1               5                   10                  15

<210> SEQ ID NO 154
<211> LENGTH: 16
<212> TYPE: PRT
<213> ORGANISM: Artificial Sequence
<220> FEATURE:
<223> OTHER INFORMATION: Antibody

<400> SEQUENCE: 154

His Ile His Phe Ser Gly Arg Pro Thr Tyr Asp Pro Ser Leu Lys Ser
1               5                   10                  15

<210> SEQ ID NO 155
<211> LENGTH: 16
<212> TYPE: PRT
<213> ORGANISM: Artificial Sequence
<220> FEATURE:
<223> OTHER INFORMATION: Antibody

<400> SEQUENCE: 155

His Ile His Phe Ser Gly Arg Pro Thr Tyr Asp Pro Ser Leu Leu Ser
1               5                   10                  15

<210> SEQ ID NO 156
<211> LENGTH: 16
<212> TYPE: PRT
<213> ORGANISM: Artificial Sequence
<220> FEATURE:
<223> OTHER INFORMATION: Antibody

<400> SEQUENCE: 156

His Ile His Phe Ser Gly Arg Pro Thr Tyr Asp Pro Ser Leu His Ser
1               5                   10                  15

<210> SEQ ID NO 157
<211> LENGTH: 16
<212> TYPE: PRT
<213> ORGANISM: Artificial Sequence
<220> FEATURE:
<223> OTHER INFORMATION: Antibody

<400> SEQUENCE: 157

His Ile His Phe Ser Gly Arg Pro Thr Tyr Asp Pro Ser Leu Phe Ser
1               5                   10                  15

<210> SEQ ID NO 158
<211> LENGTH: 16
```

-continued

```
<212> TYPE: PRT
<213> ORGANISM: Artificial Sequence
<220> FEATURE:
<223> OTHER INFORMATION: Antibody

<400> SEQUENCE: 158

His Ile His Phe Ser Gly Arg Pro Thr Tyr Asp Pro Ser Leu Arg Ser
1               5                   10                  15

<210> SEQ ID NO 159
<211> LENGTH: 16
<212> TYPE: PRT
<213> ORGANISM: Artificial Sequence
<220> FEATURE:
<223> OTHER INFORMATION: Antibody

<400> SEQUENCE: 159

His Ile His Trp Ser Gly Arg Pro Thr Tyr Asp Pro Ser Leu Ser Ser
1               5                   10                  15

<210> SEQ ID NO 160
<211> LENGTH: 16
<212> TYPE: PRT
<213> ORGANISM: Artificial Sequence
<220> FEATURE:
<223> OTHER INFORMATION: Antibody

<400> SEQUENCE: 160

His Ile His Trp Ser Gly Arg Pro Thr Tyr Asp Pro Ser Leu Lys Ser
1               5                   10                  15

<210> SEQ ID NO 161
<211> LENGTH: 16
<212> TYPE: PRT
<213> ORGANISM: Artificial Sequence
<220> FEATURE:
<223> OTHER INFORMATION: Antibody

<400> SEQUENCE: 161

His Ile His Trp Ser Gly Arg Pro Thr Tyr Asp Pro Ser Leu Leu Ser
1               5                   10                  15

<210> SEQ ID NO 162
<211> LENGTH: 16
<212> TYPE: PRT
<213> ORGANISM: Artificial Sequence
<220> FEATURE:
<223> OTHER INFORMATION: Antibody

<400> SEQUENCE: 162

His Ile His Trp Ser Gly Arg Pro Thr Tyr Asp Pro Ser Leu His Ser
1               5                   10                  15

<210> SEQ ID NO 163
<211> LENGTH: 16
<212> TYPE: PRT
<213> ORGANISM: Artificial Sequence
<220> FEATURE:
<223> OTHER INFORMATION: Antibody

<400> SEQUENCE: 163

His Ile His Trp Ser Gly Arg Pro Thr Tyr Asp Pro Ser Leu Phe Ser
1               5                   10                  15

<210> SEQ ID NO 164
<211> LENGTH: 16
<212> TYPE: PRT
```

```
<213> ORGANISM: Artificial Sequence
<220> FEATURE:
<223> OTHER INFORMATION: Antibody

<400> SEQUENCE: 164

His Ile His Trp Ser Gly Arg Pro Thr Tyr Asp Pro Ser Leu Arg Ser
1               5                   10                  15

<210> SEQ ID NO 165
<211> LENGTH: 16
<212> TYPE: PRT
<213> ORGANISM: Artificial Sequence
<220> FEATURE:
<223> OTHER INFORMATION: Antibody

<400> SEQUENCE: 165

His Ile His Tyr Ser Gly Arg Pro Thr Tyr Asp Pro Ser Leu Ser Ser
1               5                   10                  15

<210> SEQ ID NO 166
<211> LENGTH: 16
<212> TYPE: PRT
<213> ORGANISM: Artificial Sequence
<220> FEATURE:
<223> OTHER INFORMATION: Antibody

<400> SEQUENCE: 166

His Ile His Tyr Ser Gly Arg Pro Thr Tyr Asp Pro Ser Leu Lys Ser
1               5                   10                  15

<210> SEQ ID NO 167
<211> LENGTH: 16
<212> TYPE: PRT
<213> ORGANISM: Artificial Sequence
<220> FEATURE:
<223> OTHER INFORMATION: Antibody

<400> SEQUENCE: 167

His Ile His Tyr Ser Gly Arg Pro Thr Tyr Asp Pro Ser Leu Leu Ser
1               5                   10                  15

<210> SEQ ID NO 168
<211> LENGTH: 16
<212> TYPE: PRT
<213> ORGANISM: Artificial Sequence
<220> FEATURE:
<223> OTHER INFORMATION: Antibody

<400> SEQUENCE: 168

His Ile His Tyr Ser Gly Arg Pro Thr Tyr Asp Pro Ser Leu His Ser
1               5                   10                  15

<210> SEQ ID NO 169
<211> LENGTH: 16
<212> TYPE: PRT
<213> ORGANISM: Artificial Sequence
<220> FEATURE:
<223> OTHER INFORMATION: Antibody

<400> SEQUENCE: 169

His Ile His Tyr Ser Gly Arg Pro Thr Tyr Asp Pro Ser Leu Phe Ser
1               5                   10                  15

<210> SEQ ID NO 170
<211> LENGTH: 16
<212> TYPE: PRT
<213> ORGANISM: Artificial Sequence
```

<220> FEATURE:
<223> OTHER INFORMATION: Antibody

<400> SEQUENCE: 170

His Ile His Tyr Ser Gly Arg Pro Thr Tyr Asp Pro Ser Leu Arg Ser
1               5                   10                  15

<210> SEQ ID NO 171
<211> LENGTH: 32
<212> TYPE: PRT
<213> ORGANISM: Artificial Sequence
<220> FEATURE:
<223> OTHER INFORMATION: Antibody

<400> SEQUENCE: 171

Arg Val Thr Ile Ser Arg Glu Thr Ala Lys Asn Gln Phe Ser Leu Lys
1               5                   10                  15

Leu Thr Ser Met Thr Ala Ala Asp Thr Ala Val Tyr Tyr Cys Ala Arg
            20                  25                  30

<210> SEQ ID NO 172
<211> LENGTH: 32
<212> TYPE: PRT
<213> ORGANISM: Artificial Sequence
<220> FEATURE:
<223> OTHER INFORMATION: Antibody

<400> SEQUENCE: 172

Arg Val Thr Ile Ser Arg Asp Thr Ala Lys Asn Gln Phe Ser Leu Lys
1               5                   10                  15

Leu Thr Ser Met Thr Ala Ala Asp Thr Ala Val Tyr Tyr Cys Ala Arg
            20                  25                  30

<210> SEQ ID NO 173
<211> LENGTH: 32
<212> TYPE: PRT
<213> ORGANISM: Artificial Sequence
<220> FEATURE:
<223> OTHER INFORMATION: Antibody

<400> SEQUENCE: 173

Arg Val Thr Ile Ser Lys Glu Thr Ala Lys Asn Gln Phe Ser Leu Lys
1               5                   10                  15

Leu Thr Ser Met Thr Ala Ala Asp Thr Ala Val Tyr Tyr Cys Ala Arg
            20                  25                  30

<210> SEQ ID NO 174
<211> LENGTH: 32
<212> TYPE: PRT
<213> ORGANISM: Artificial Sequence
<220> FEATURE:
<223> OTHER INFORMATION: Antibody

<400> SEQUENCE: 174

Arg Val Thr Ile Ser Lys Asp Thr Ala Lys Asn Gln Phe Ser Leu Lys
1               5                   10                  15

Leu Thr Ser Met Thr Ala Ala Asp Thr Ala Val Tyr Tyr Cys Ala Arg
            20                  25                  30

<210> SEQ ID NO 175
<211> LENGTH: 32
<212> TYPE: PRT
<213> ORGANISM: Artificial Sequence
<220> FEATURE:
<223> OTHER INFORMATION: Antibody

<400> SEQUENCE: 175

Arg Val Ser Ile Ser Arg Glu Thr Ala Lys Asn Gln Phe Ser Leu Lys
1               5                   10                  15

Leu Thr Ser Met Thr Ala Ala Asp Thr Ala Val Tyr Tyr Cys Ala Arg
            20                  25                  30

<210> SEQ ID NO 176
<211> LENGTH: 32
<212> TYPE: PRT
<213> ORGANISM: Artificial Sequence
<220> FEATURE:
<223> OTHER INFORMATION: Antibody

<400> SEQUENCE: 176

Arg Val Ser Ile Ser Arg Asp Thr Ala Lys Asn Gln Phe Ser Leu Lys
1               5                   10                  15

Leu Thr Ser Met Thr Ala Ala Asp Thr Ala Val Tyr Tyr Cys Ala Arg
            20                  25                  30

<210> SEQ ID NO 177
<211> LENGTH: 32
<212> TYPE: PRT
<213> ORGANISM: Artificial Sequence
<220> FEATURE:
<223> OTHER INFORMATION: Antibody

<400> SEQUENCE: 177

Arg Val Ser Ile Ser Lys Glu Thr Ala Lys Asn Gln Phe Ser Leu Lys
1               5                   10                  15

Leu Thr Ser Met Thr Ala Ala Asp Thr Ala Val Tyr Tyr Cys Ala Arg
            20                  25                  30

<210> SEQ ID NO 178
<211> LENGTH: 32
<212> TYPE: PRT
<213> ORGANISM: Artificial Sequence
<220> FEATURE:
<223> OTHER INFORMATION: Antibody

<400> SEQUENCE: 178

Arg Val Ser Ile Ser Lys Asp Thr Ala Lys Asn Gln Phe Ser Leu Lys
1               5                   10                  15

Leu Thr Ser Met Thr Ala Ala Asp Thr Ala Val Tyr Tyr Cys Ala Arg
            20                  25                  30

<210> SEQ ID NO 179
<211> LENGTH: 32
<212> TYPE: PRT
<213> ORGANISM: Artificial Sequence
<220> FEATURE:
<223> OTHER INFORMATION: Antibody

<400> SEQUENCE: 179

Arg Ile Thr Ile Ser Arg Glu Thr Ala Lys Asn Gln Phe Ser Leu Lys
1               5                   10                  15

Leu Thr Ser Met Thr Ala Ala Asp Thr Ala Val Tyr Tyr Cys Ala Arg
            20                  25                  30

<210> SEQ ID NO 180
<211> LENGTH: 32
<212> TYPE: PRT
<213> ORGANISM: Artificial Sequence
<220> FEATURE:

<223> OTHER INFORMATION: Antibody

<400> SEQUENCE: 180

Arg Ile Thr Ile Ser Arg Asp Thr Ala Lys Asn Gln Phe Ser Leu Lys
1               5                   10                  15
Leu Thr Ser Met Thr Ala Ala Asp Thr Ala Val Tyr Tyr Cys Ala Arg
            20                  25                  30

<210> SEQ ID NO 181
<211> LENGTH: 32
<212> TYPE: PRT
<213> ORGANISM: Artificial Sequence
<220> FEATURE:
<223> OTHER INFORMATION: Antibody

<400> SEQUENCE: 181

Arg Ile Thr Ile Ser Lys Glu Thr Ala Lys Asn Gln Phe Ser Leu Lys
1               5                   10                  15
Leu Thr Ser Met Thr Ala Ala Asp Thr Ala Val Tyr Tyr Cys Ala Arg
            20                  25                  30

<210> SEQ ID NO 182
<211> LENGTH: 32
<212> TYPE: PRT
<213> ORGANISM: Artificial Sequence
<220> FEATURE:
<223> OTHER INFORMATION: Antibody

<400> SEQUENCE: 182

Arg Ile Thr Ile Ser Lys Asp Thr Ala Lys Asn Gln Phe Ser Leu Lys
1               5                   10                  15
Leu Thr Ser Met Thr Ala Ala Asp Thr Ala Val Tyr Tyr Cys Ala Arg
            20                  25                  30

<210> SEQ ID NO 183
<211> LENGTH: 32
<212> TYPE: PRT
<213> ORGANISM: Artificial Sequence
<220> FEATURE:
<223> OTHER INFORMATION: Antibody

<400> SEQUENCE: 183

Arg Ile Ser Ile Ser Arg Glu Thr Ala Lys Asn Gln Phe Ser Leu Lys
1               5                   10                  15
Leu Thr Ser Met Thr Ala Ala Asp Thr Ala Val Tyr Tyr Cys Ala Arg
            20                  25                  30

<210> SEQ ID NO 184
<211> LENGTH: 32
<212> TYPE: PRT
<213> ORGANISM: Artificial Sequence
<220> FEATURE:
<223> OTHER INFORMATION: Antibody

<400> SEQUENCE: 184

Arg Ile Ser Ile Ser Arg Asp Thr Ala Lys Asn Gln Phe Ser Leu Lys
1               5                   10                  15
Leu Thr Ser Met Thr Ala Ala Asp Thr Ala Val Tyr Tyr Cys Ala Arg
            20                  25                  30

<210> SEQ ID NO 185
<211> LENGTH: 32
<212> TYPE: PRT
<213> ORGANISM: Artificial Sequence
<220> FEATURE:
<223> OTHER INFORMATION: Antibody

<400> SEQUENCE: 185

Arg Ile Ser Ile Ser Lys Glu Thr Ala Lys Asn Gln Phe Ser Leu Lys
1               5                   10                  15

Leu Thr Ser Met Thr Ala Ala Asp Thr Ala Val Tyr Tyr Cys Ala Arg
            20                  25                  30

<210> SEQ ID NO 186
<211> LENGTH: 32
<212> TYPE: PRT
<213> ORGANISM: Artificial Sequence
<220> FEATURE:
<223> OTHER INFORMATION: Antibody

<400> SEQUENCE: 186

Arg Ile Ser Ile Ser Lys Asp Thr Ala Lys Asn Gln Phe Ser Leu Lys
1               5                   10                  15

Leu Thr Ser Met Thr Ala Ala Asp Thr Ala Val Tyr Tyr Cys Ala Arg
            20                  25                  30

<210> SEQ ID NO 187
<211> LENGTH: 23
<212> TYPE: PRT
<213> ORGANISM: Artificial Sequence
<220> FEATURE:
<223> OTHER INFORMATION: Antibody
<220> FEATURE:
<221> NAME/KEY: VARIANT
<222> LOCATION: (2)..(2)
<223> OTHER INFORMATION: Xaa is Ile or Asn
<220> FEATURE:
<221> NAME/KEY: VARIANT
<222> LOCATION: (15)..(15)
<223> OTHER INFORMATION: Xaa is Ala or Pro

<400> SEQUENCE: 187

Glu Xaa Val Leu Thr Gln Ser Pro Gly Thr Leu Ser Leu Ser Xaa Gly
1               5                   10                  15

Glu Arg Ala Thr Leu Ser Cys
            20

<210> SEQ ID NO 188
<211> LENGTH: 10
<212> TYPE: PRT
<213> ORGANISM: Artificial Sequence
<220> FEATURE:
<223> OTHER INFORMATION: Antibody

<400> SEQUENCE: 188

Ser Ala Ser Ser Ser Leu Ser Tyr Ile His
1               5                   10

<210> SEQ ID NO 189
<211> LENGTH: 15
<212> TYPE: PRT
<213> ORGANISM: Artificial Sequence
<220> FEATURE:
<223> OTHER INFORMATION: Antibody

<400> SEQUENCE: 189

Trp Tyr Gln Gln Lys Pro Gly Gln Ala Pro Arg Leu Leu Ile Tyr
1               5                   10                  15

<210> SEQ ID NO 190

```
<211> LENGTH: 7
<212> TYPE: PRT
<213> ORGANISM: Artificial Sequence
<220> FEATURE:
<223> OTHER INFORMATION: Antibody

<400> SEQUENCE: 190

Asp Thr Ser Asn Leu Ala Ser
1               5

<210> SEQ ID NO 191
<211> LENGTH: 32
<212> TYPE: PRT
<213> ORGANISM: Artificial Sequence
<220> FEATURE:
<223> OTHER INFORMATION: Antibody
<220> FEATURE:
<221> NAME/KEY: VARIANT
<222> LOCATION: (13)..(13)
<223> OTHER INFORMATION: Xaa is Thr or Asn

<400> SEQUENCE: 191

Gly Ile Pro Asp Arg Phe Ser Gly Ser Gly Ser Gly Xaa Asp Phe Thr
1               5                   10                  15
Leu Thr Ile Ser Arg Val Glu Pro Glu Asp Phe Ala Val Tyr Tyr Cys
            20                  25                  30

<210> SEQ ID NO 192
<211> LENGTH: 9
<212> TYPE: PRT
<213> ORGANISM: Artificial Sequence
<220> FEATURE:
<223> OTHER INFORMATION: Antibody

<400> SEQUENCE: 192

Phe Gln Gly Ser Glu Tyr Pro Leu Thr
1               5

<210> SEQ ID NO 193
<211> LENGTH: 11
<212> TYPE: PRT
<213> ORGANISM: Artificial Sequence
<220> FEATURE:
<223> OTHER INFORMATION: Antibody

<400> SEQUENCE: 193

Phe Gly Gln Gly Thr Lys Leu Glu Ile Lys Arg
1               5                   10

<210> SEQ ID NO 194
<211> LENGTH: 81
<212> TYPE: PRT
<213> ORGANISM: Artificial Sequence
<220> FEATURE:
<223> OTHER INFORMATION: Antibody

<400> SEQUENCE: 194

Glu Ile Val Leu Thr Gln Ser Pro Gly Thr Leu Ser Leu Ser Pro Gly
1               5                   10                  15
Glu Arg Ala Thr Leu Ser Cys Trp Tyr Gln Gln Lys Pro Gly Gln Ala
            20                  25                  30
Pro Arg Leu Leu Ile Tyr Gly Ile Pro Asp Arg Phe Ser Gly Ser Gly
        35                  40                  45
Ser Gly Thr Asp Phe Thr Leu Thr Ile Ser Arg Val Glu Pro Glu Asp
    50                  55                  60
```

Phe Ala Val Tyr Tyr Cys Phe Gly Gln Gly Thr Lys Leu Glu Ile Lys
65                  70                  75                  80

Arg

<210> SEQ ID NO 195
<211> LENGTH: 23
<212> TYPE: PRT
<213> ORGANISM: Artificial Sequence
<220> FEATURE:
<223> OTHER INFORMATION: Antibody

<400> SEQUENCE: 195

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 196
<211> LENGTH: 23
<212> TYPE: PRT
<213> ORGANISM: Artificial Sequence
<220> FEATURE:
<223> OTHER INFORMATION: Antibody

<400> SEQUENCE: 196

Glu Ile Val Leu Thr Gln Ser Pro Gly Thr Leu Ser Leu Ser Ala Gly
1               5                   10                  15

Glu Arg Ala Thr Leu Ser Cys
            20

<210> SEQ ID NO 197
<211> LENGTH: 23
<212> TYPE: PRT
<213> ORGANISM: Artificial Sequence
<220> FEATURE:
<223> OTHER INFORMATION: Antibody

<400> SEQUENCE: 197

Glu Asn Val Leu Thr Gln Ser Pro Gly Thr Leu Ser Leu Ser Pro Gly
1               5                   10                  15

Glu Arg Ala Thr Leu Ser Cys
            20

<210> SEQ ID NO 198
<211> LENGTH: 23
<212> TYPE: PRT
<213> ORGANISM: Artificial Sequence
<220> FEATURE:
<223> OTHER INFORMATION: Antibody

<400> SEQUENCE: 198

Glu Asn Val Leu Thr Gln Ser Pro Gly Thr Leu Ser Leu Ser Ala Gly
1               5                   10                  15

Glu Arg Ala Thr Leu Ser Cys
            20

<210> SEQ ID NO 199
<211> LENGTH: 32
<212> TYPE: PRT
<213> ORGANISM: Artificial Sequence
<220> FEATURE:
<223> OTHER INFORMATION: Antibody

<400> SEQUENCE: 199

```
Gly Ile Pro Asp Arg Phe Ser Gly Ser Gly Ser Gly Thr Asp Phe Thr
1               5                   10                  15

Leu Thr Ile Ser Arg Val Glu Pro Glu Asp Phe Ala Val Tyr Tyr Cys
            20                  25                  30
```

<210> SEQ ID NO 200
<211> LENGTH: 32
<212> TYPE: PRT
<213> ORGANISM: Artificial Sequence
<220> FEATURE:
<223> OTHER INFORMATION: Antibody

<400> SEQUENCE: 200

```
Gly Ile Pro Asp Arg Phe Ser Gly Ser Gly Ser Gly Asn Asp Phe Thr
1               5                   10                  15

Leu Thr Ile Ser Arg Val Glu Pro Glu Asp Phe Ala Val Tyr Tyr Cys
            20                  25                  30
```

<210> SEQ ID NO 201
<211> LENGTH: 30
<212> TYPE: PRT
<213> ORGANISM: Artificial Sequence
<220> FEATURE:
<223> OTHER INFORMATION: Antibody
<220> FEATURE:
<221> NAME/KEY: VARIANT
<222> LOCATION: (29)..(29)
<223> OTHER INFORMATION: Xaa is Ile, Leu or Val
<220> FEATURE:
<221> NAME/KEY: VARIANT
<222> LOCATION: (30)..(30)
<223> OTHER INFORMATION: Xaa is Ser or Thr

<400> SEQUENCE: 201

```
Glu Val Gln Leu Gln Gln Trp Gly Ala Gly Leu Leu Lys Pro Ser Glu
1               5                   10                  15

Thr Leu Ser Leu Thr Cys Ala Val Tyr Gly Tyr Ser Xaa Xaa
            20                  25                  30
```

<210> SEQ ID NO 202
<211> LENGTH: 14
<212> TYPE: PRT
<213> ORGANISM: Artificial Sequence
<220> FEATURE:
<223> OTHER INFORMATION: Antibody
<220> FEATURE:
<221> NAME/KEY: VARIANT
<222> LOCATION: (13)..(13)
<223> OTHER INFORMATION: Xaa is Met or Ile

<400> SEQUENCE: 202

```
Trp Ile Arg Gln Pro Pro Gly Lys Gly Leu Glu Trp Xaa Gly
1               5                   10
```

<210> SEQ ID NO 203
<211> LENGTH: 32
<212> TYPE: PRT
<213> ORGANISM: Artificial Sequence
<220> FEATURE:
<223> OTHER INFORMATION: Antibody
<220> FEATURE:
<221> NAME/KEY: VARIANT
<222> LOCATION: (2)..(2)
<223> OTHER INFORMATION: Xaa is Val or Ile
<220> FEATURE:
<221> NAME/KEY: VARIANT
<222> LOCATION: (3)..(3)
<223> OTHER INFORMATION: Xaa is Ser or Thr
<220> FEATURE:

```
<221> NAME/KEY: VARIANT
<222> LOCATION: (6)..(6)
<223> OTHER INFORMATION: Xaa is Arg or Lys

<400> SEQUENCE: 203

Arg Xaa Xaa Ile Ser Xaa Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 204
<211> LENGTH: 87
<212> TYPE: PRT
<213> ORGANISM: Artificial Sequence
<220> FEATURE:
<223> OTHER INFORMATION: Antibody
<220> FEATURE:
<221> NAME/KEY: VARIANT
<222> LOCATION: (29)..(29)
<223> OTHER INFORMATION: Xaa is Ile, Leu or Val
<220> FEATURE:
<221> NAME/KEY: VARIANT
<222> LOCATION: (50)..(50)
<223> OTHER INFORMATION: Xaa is Arg or Lys

<400> SEQUENCE: 204

Glu Val Gln Leu Gln Gln Trp Gly Ala Gly Leu Leu Lys Pro Ser Glu
1               5                   10                  15

Thr Leu Ser Leu Thr Cys Ala Val Tyr Gly Tyr Ser Xaa Ser Trp Ile
            20                  25                  30

Arg Gln Pro Pro Gly Lys Gly Leu Glu Trp Ile Gly Arg Val Thr Ile
        35                  40                  45

Ser Xaa Asp Thr Ser Lys Asn Gln Phe Ser Leu Lys Leu Ser Ser Val
    50                  55                  60

Thr Ala Ala Asp Thr Ala Val Tyr Tyr Cys Ala Arg Trp Gly Gln Gly
65                  70                  75                  80

Thr Leu Val Thr Val Ser Ser
                85

<210> SEQ ID NO 205
<211> LENGTH: 30
<212> TYPE: PRT
<213> ORGANISM: Artificial Sequence
<220> FEATURE:
<223> OTHER INFORMATION: Antibody

<400> SEQUENCE: 205

Glu Val Gln Leu Gln Gln Trp Gly Ala Gly Leu Leu Lys Pro Ser Glu
1               5                   10                  15

Thr Leu Ser Leu Thr Cys Ala Val Tyr Gly Tyr Ser Ile Ser
            20                  25                  30

<210> SEQ ID NO 206
<211> LENGTH: 30
<212> TYPE: PRT
<213> ORGANISM: Artificial Sequence
<220> FEATURE:
<223> OTHER INFORMATION: Antibody

<400> SEQUENCE: 206

Glu Val Gln Leu Gln Gln Trp Gly Ala Gly Leu Leu Lys Pro Ser Glu
1               5                   10                  15

Thr Leu Ser Leu Thr Cys Ala Val Tyr Gly Tyr Ser Ile Thr
            20                  25                  30
```

<210> SEQ ID NO 207
<211> LENGTH: 30
<212> TYPE: PRT
<213> ORGANISM: Artificial Sequence
<220> FEATURE:
<223> OTHER INFORMATION: Antibody

<400> SEQUENCE: 207

Glu Val Gln Leu Gln Gln Trp Gly Ala Gly Leu Leu Lys Pro Ser Glu
1               5                   10                  15
Thr Leu Ser Leu Thr Cys Ala Val Tyr Gly Tyr Ser Leu Ser
            20                  25                  30

<210> SEQ ID NO 208
<211> LENGTH: 30
<212> TYPE: PRT
<213> ORGANISM: Artificial Sequence
<220> FEATURE:
<223> OTHER INFORMATION: Antibody

<400> SEQUENCE: 208

Glu Val Gln Leu Gln Gln Trp Gly Ala Gly Leu Leu Lys Pro Ser Glu
1               5                   10                  15
Thr Leu Ser Leu Thr Cys Ala Val Tyr Gly Tyr Ser Leu Thr
            20                  25                  30

<210> SEQ ID NO 209
<211> LENGTH: 30
<212> TYPE: PRT
<213> ORGANISM: Artificial Sequence
<220> FEATURE:
<223> OTHER INFORMATION: Antibody

<400> SEQUENCE: 209

Glu Val Gln Leu Gln Gln Trp Gly Ala Gly Leu Leu Lys Pro Ser Glu
1               5                   10                  15
Thr Leu Ser Leu Thr Cys Ala Val Tyr Gly Tyr Ser Val Ser
            20                  25                  30

<210> SEQ ID NO 210
<211> LENGTH: 30
<212> TYPE: PRT
<213> ORGANISM: Artificial Sequence
<220> FEATURE:
<223> OTHER INFORMATION: Antibody

<400> SEQUENCE: 210

Glu Val Gln Leu Gln Gln Trp Gly Ala Gly Leu Leu Lys Pro Ser Glu
1               5                   10                  15
Thr Leu Ser Leu Thr Cys Ala Val Tyr Gly Tyr Ser Val Thr
            20                  25                  30

<210> SEQ ID NO 211
<211> LENGTH: 23
<212> TYPE: PRT
<213> ORGANISM: Artificial Sequence
<220> FEATURE:
<223> OTHER INFORMATION: Antibody
<220> FEATURE:
<221> NAME/KEY: VARIANT
<222> LOCATION: (2)..(2)
<223> OTHER INFORMATION: Xaa is Ile or Asn

<400> SEQUENCE: 211

-continued

```
Glu Xaa Val Leu Thr Gln Ser Pro Ala Thr Leu Ser Leu Ser Pro Gly
1               5                   10                  15

Glu Arg Ala Thr Leu Ser Cys
            20

<210> SEQ ID NO 212
<211> LENGTH: 32
<212> TYPE: PRT
<213> ORGANISM: Artificial Sequence
<220> FEATURE:
<223> OTHER INFORMATION: Antibody
<220> FEATURE:
<221> NAME/KEY: VARIANT
<222> LOCATION: (13)..(13)
<223> OTHER INFORMATION: Xaa is Thr or Asn

<400> SEQUENCE: 212

Gly Ile Pro Asp Arg Phe Ser Gly Ser Gly Ser Gly Xaa Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 213
<211> LENGTH: 81
<212> TYPE: PRT
<213> ORGANISM: Artificial Sequence
<220> FEATURE:
<223> OTHER INFORMATION: Antibody

<400> SEQUENCE: 213

Glu Ile Val Leu Thr Gln Ser Pro Ala Thr Leu Ser Leu Ser Pro Gly
1               5                   10                  15

Glu Arg Ala Thr Leu Ser Cys Trp Tyr Gln Gln Lys Pro Gly Gln Ala
            20                  25                  30

Pro Arg Leu Leu Ile Tyr Gly Ile Pro Asp Arg Phe Ser Gly Ser Gly
        35                  40                  45

Ser Gly Thr Asp Phe Thr Leu Thr Ile Ser Arg Leu Glu Pro Glu Asp
    50                  55                  60

Phe Ala Val Tyr Tyr Cys Phe Gly Gly Gly Thr Lys Val Glu Ile Lys
65                  70                  75                  80

Arg

<210> SEQ ID NO 214
<211> LENGTH: 23
<212> TYPE: PRT
<213> ORGANISM: Artificial Sequence
<220> FEATURE:
<223> OTHER INFORMATION: Antibody

<400> SEQUENCE: 214

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 215
<211> LENGTH: 23
<212> TYPE: PRT
<213> ORGANISM: Artificial Sequence
<220> FEATURE:
<223> OTHER INFORMATION: Antibody

<400> SEQUENCE: 215
```

-continued

```
Glu Asn Val Leu Thr Gln Ser Pro Ala Thr Leu Ser Leu Ser Pro Gly
1               5                   10                  15

Glu Arg Ala Thr Leu Ser Cys
            20
```

<210> SEQ ID NO 216
<211> LENGTH: 32
<212> TYPE: PRT
<213> ORGANISM: Artificial Sequence
<220> FEATURE:
<223> OTHER INFORMATION: Antibody

<400> SEQUENCE: 216

```
Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30
```

<210> SEQ ID NO 217
<211> LENGTH: 32
<212> TYPE: PRT
<213> ORGANISM: Artificial Sequence
<220> FEATURE:
<223> OTHER INFORMATION: Antibody

<400> SEQUENCE: 217

```
Gly Ile Pro Asp Arg Phe Ser Gly Ser Gly Ser Gly Asn Asp Phe Thr
1               5                   10                  15

Leu Thr Ile Ser Arg Leu Glu Pro Glu Asp Phe Ala Val Tyr Tyr Cys
            20                  25                  30
```

<210> SEQ ID NO 218
<211> LENGTH: 32
<212> TYPE: PRT
<213> ORGANISM: Artificial Sequence
<220> FEATURE:
<223> OTHER INFORMATION: Antibody

<400> SEQUENCE: 218

```
Arg Val Thr Ile Ser Arg Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30
```

<210> SEQ ID NO 219
<211> LENGTH: 32
<212> TYPE: PRT
<213> ORGANISM: Artificial Sequence
<220> FEATURE:
<223> OTHER INFORMATION: Antibody

<400> SEQUENCE: 219

```
Arg Val Thr Ile Ser Lys Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30
```

<210> SEQ ID NO 220
<211> LENGTH: 32
<212> TYPE: PRT
<213> ORGANISM: Artificial Sequence
<220> FEATURE:
<223> OTHER INFORMATION: Antibody

<400> SEQUENCE: 220

Arg Val Ser Ile Ser Arg Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 221
<211> LENGTH: 32
<212> TYPE: PRT
<213> ORGANISM: Artificial Sequence
<220> FEATURE:
<223> OTHER INFORMATION: Antibody

<400> SEQUENCE: 221

Arg Val Ser Ile Ser Lys Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 222
<211> LENGTH: 32
<212> TYPE: PRT
<213> ORGANISM: Artificial Sequence
<220> FEATURE:
<223> OTHER INFORMATION: Antibody

<400> SEQUENCE: 222

Arg Ile Thr Ile Ser Arg Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 223
<211> LENGTH: 32
<212> TYPE: PRT
<213> ORGANISM: Artificial Sequence
<220> FEATURE:
<223> OTHER INFORMATION: Antibody

<400> SEQUENCE: 223

Arg Ile Thr Ile Ser Lys Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 224
<211> LENGTH: 32
<212> TYPE: PRT
<213> ORGANISM: Artificial Sequence
<220> FEATURE:
<223> OTHER INFORMATION: Antibody

<400> SEQUENCE: 224

Arg Ile Ser Ile Ser Arg Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 225
<211> LENGTH: 32
<212> TYPE: PRT
<213> ORGANISM: Artificial Sequence
<220> FEATURE:
<223> OTHER INFORMATION: Antibody

```
<400> SEQUENCE: 225

Arg Ile Ser Ile Ser Lys Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30
```